United States Patent [19]

Laundon et al.

[11] 4,113,591
[45] Sep. 12, 1978

[54] PREPARATION OF CEPHALOSPORIN COMPOUNDS

[75] Inventors: Brian Laundon, Northolt; Brian Richard Cowley, Greenford; David Cedric Humber, London, all of England

[73] Assignee: Glaxo Laboratories Limited, Greenford, England

[21] Appl. No.: 749,300

[22] Filed: Dec. 10, 1976

Related U.S. Application Data

[60] Continuation of Ser. No. 593,273, Jul. 7, 1975, abandoned, which is a continuation of Ser. No. 455,073, Mar. 27, 1974, abandoned, which is a continuation of Ser. No. 306,308, Nov. 14, 1972, abandoned, which is a division of Ser. No. 66,128, Aug. 21, 1970, abandoned.

[30] Foreign Application Priority Data

Aug. 26, 1969 [GB] United Kingdom ............... 42502/69
Mar. 26, 1970 [GB] United Kingdom ............... 14980/70
Jan. 23, 1970 [GB] United Kingdom ............... 3463/70
Jul. 10, 1970 [GB] United Kingdom ............... 33698/70

[51] Int. Cl.$^2$ ............................................. B01J 1/10
[52] U.S. Cl. ....................... 204/158 HA; 204/158 HE
[58] Field of Search ..................... 204/158 HA, 158 H

[56] References Cited

U.S. PATENT DOCUMENTS

| 3,544,581 | 12/1970 | Essery ........................ 204/158 HA |
| 3,652,546 | 3/1972 | Cheney et al. ............... 204/158 HA |

*Primary Examiner*—Howard S. Williams
*Attorney, Agent, or Firm*—Bacon & Thomas

[57] ABSTRACT

The invention relates to a novel method for the preparation of a 7$\beta$-acylamido-3-bromomethylceph-3-em-4-carboxylic acid-1-oxide compound by brominating a 7$\beta$-acylamido-3-methylceph-3-em-4-carboxylic acid-1-oxide compound.

4 Claims, No Drawings

PREPARATION OF CEPHALOSPORIN COMPOUNDS

This is a continuation of application Ser. No. 593,273, filed July 7, 1975, now abandoned, which is in turn a continuation of application Ser. No. 455,073, filed Mar. 27, 1974, now abandoned, which is in turn a continuation of application Ser. No. 306,308, filed Nov. 14, 1972, now abandoned, which is in turn a division of application Ser. No. 66,128, filed Aug. 21, 1970, now abandoned.

This invention is concerned with a process for the transformation of cephalosporin compounds.

The compounds referred to in this specification are generally named with reference to cepham (see J.A.C.S. 1962, 84, 3400 and J. Chem. Soc., 1965, 5031). The term 'cephem' refers to the basic cepham structure with one double bond.

In U.S. Pat. Specification No. 3,275,626 there is described a general method for preparing antibiotic substances, including cephalosporins, which comprises heating a so-called penicillin sulphoxide under acid conditions to a temperature of from about 100° to about 175° C. By means of this process esters of 6β-acylamidopenicillanic acid 1-oxides can be converted into analogous esters of 7β-acylamido-3-methylceph-3-em-4-carboxylic acids. By suitable choice of reaction conditions the cephalosporin analogues can be obtained in high yields. Although some of these cephalosporin analogues may have potent antibacterial properties it is desirable to be able to transform the resulting cephalosporin analogues, which contain a 3-methyl group, into related compounds containing a substituted 3-methyl group. Cephalosporin compounds containing 3-methyl groups may also be obtained by fully synthetic methods and it would also enable one to transfer these in like manner.

Attempts which we have made to halogenate esters of 7β-acylamido-3-methylceph-3-em-4-carboxylic acids have met with little success. We have, however, found that bromination of compounds of the general formula:

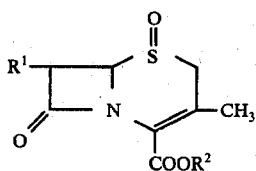

(I)

(where $R^1$ is a protected amino group and $R^2$ is hydrogen or a carboxyl blocking group e.g. the residue of an ester-forming alcohol or phenol $R^2OH$) yields compounds of general formula:

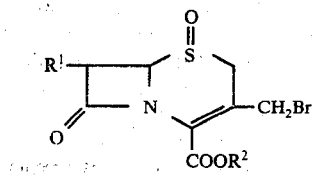

(II)

The 1-oxide group in formulae I and II and in subsequent formulae preferably has the β-configuration.

$R^1$ is conveniently an acylamido group, especially that of a penicillin obtained by a fermentation process e.g. phenylacetamido or phenoxyacetamido since compounds of formula I may be readily derived from penicillins as explained above. The group $R^1$ may advantageously be a formamido group; this group is substantially stable under the bromination conditions and can be readily cleaved subsequently to enable another acyl group to be introduced.

The acylamido group may not be the desired group in the end product but this can be obviated by subsequent transformations described below. It is not necessary that the initial acylamido group should be completely inert since it may be cleaved by these subsequent transformations.

CARBOXYL BLOCKING GROUPS

We prefer to use the cephalosporin compounds as an ester with an alcohol or phenol which may readily be split off, e.g. by hydrolysis or reduction, at a later stage of the reaction sequence. Esters are in general more soluble than the free acids in solvents for bromination reactions and the bromination proceeds more readily. If desired, the cephalosporin compound (I) may be employed as the free 4—COOH compound or salt thereof.

Alcohol and phenol residues which may readily be split off include those containing electron-attracting substituents for example sulpho groups and esterified carboxyl groups; these groups may be subsequently split off by alkaline reagents. Benzyl and o-benzyloxyphenoxy ester groups may be removed by hydrogenolysis. A preferred method of removal involves cleavage by acid and groups which may be removed by acid include adamantyl, t-butyl, benzyl residues such as anisyl and the residues of alkanols containing electron donors in the α-position such as acyloxy, alkoxy, benzoyloxy, substituted benzoyloxy, halogen, alkylthio, phenyl, alkoxy-phenyl or aromatic heterocyclic. It should be appreciated that some of these groups may be subject to concomitant bromination.

Alcohol residues which may be readily split off subsequently by reduction are those of a 2,2,2-trihalogenoethanol, e.g. 2,2,2-trichloroethanol, p-nitrobenzyl alcohol or 4-pyridylmethanol. 2,2,2-Trihalogenoethyl groups may conveniently be removed by zinc/acetic acid, zinc/formic acid, zinc/lower alcohol or zinc/pyridine or by chromous reagents; p-nitrobenzyl groups may conveniently be removed by hydrogenolysis.

Where the esterifying group is subsequently removed by an acid catalysed reaction, this may be effected by using formic acid or trifluoroacetic acid (e.g. in conjunction with anisole) or alternatively by using hydrochloric acid (e.g. in admixture with acetic acid).

We particularly prefer to use those compounds having a 2,2,2-trichloroethoxycarbonyl or a t-butoxycarbonyl group as the ester group in the bromination process according to the invention.

Other ester groups which can readily be converted to carboxy groups include silyloxycarbonyl groups.

Although silyloxycarbonyl groups may be formed by reacting the carboxyl group with a silanol in some cases it may be more convenient to react the carboxyl group with a derivative of a silanol e.g. the corresponding chloride or amine. Thus silyloxycarbonyl derivatives are formed with tetravalent silicon moieties, and the silylating agent conveniently is a halosilane or a silazane of the formula $R^4_3SiX$; $R^4_2SiX_2$; $R^4_3Si.NR^4_2$; $R^4_3Si.NH.SiR^4_3$; $R^4_3Si.NH.COR^4$; $R^4_3Si.NH.CO.NH.SiR^4_3$; $R^4NH.CO.NR^4.SiR^4_3$; or $R^4C(OSiR^4_3):NSiR^4_3$ where X is a halogen and the various groups R⁴, which can be the same or different, represents hydrogen atoms or alkyl, e.g. methyl, ethyl, n-propyl, iso-propyl; aryl, e.g. phenyl; or aralkyl e.g. benzyl groups. Some of these compounds may not be particularly stable under the reaction conditions where R⁴ is H for all R⁴ groups. It is generally preferred that the R⁴ groups should be hydrocarbon groups and preferably the hydrocarbon group should be methyl or phenyl as, for example, in hexamethyldisilazane, $(Me_3Si)_2NH$. Examples of suitable silylating agents are trimethyl chlorosilane, hexamethyldisilazane, triethyl chlorosilane, methyl trichlorosilane, dimethyl dichlorosilane, triethyl bromosilane, tri-n-propyl chlorosilane, bromomethyl dimethyl chlorosilane, tri-n-butyl chlorosilane, methyl diethyl chlorosilane, dimethyl ethyl chlorosilane, phenyl dimethyl bromosilane, benzyl methyl ethyl chlorosilane, phenyl ethyl methyl chlorosilane, triphenyl chlorosilane, tri-o-tolyl chlorosilane, tri-p-dimethylaminophenyl chlorosilane, N-ethyl triethylsilylamine, hexaethyldisilazane, triphenyl silylamine, tri-n-propyl silylamine, tetraethyl dimethyl disilazane, tetramethyl diethyl disilazane, tetramethyl diphenyl disilazane, hexaphenyldisilazane and hexa-p-tolyl disilazane.

When preparing compounds of the formula I having silyloxycarbonyl groups on a commercial scale it may be advantageous to employ silyl chlorides such as, for example, $Me_3SiCl$, or $Me_2SiCl_2$ in conjunction with a base such as, for example, diethylamine, triethylamine, dimethylaniline, quinoline, lutidine or pyridine.

An advantage accruing from the use of compounds of the formula I wherein the ester is a silyloxycarbonyl group in the process according to the invention is that the esterifying group is removed under mild conditions and hence tends to be removed during one of the isolation or subsequent reaction stages.

The siloxycarbonyl group is easily converted to a carboxy group by exposing the derivative to an excess of a compound(s) containing active hydrogen, e.g. water, acidified or basified water, alcohols and phenols.

PREPARATION OF 1-OXIDE STARTING MATERIALS

Compounds of formula I may be prepared by oxidation of a compound of the general formula:

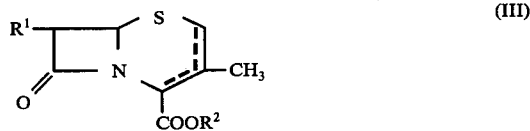

(III)

where $R^1$ and $R^2$ have the above defined meanings and the dotted line between the 2-, 3- and 4-position indicates that the compound may be a $\Delta^2$ or $\Delta^3$ compound or a mixture thereof. The oxidation may be carried out as described by Cocker et al (J. Chem. Soc. 1965, 5015). The cephalosporin compound (III) is mixed with the oxidising agent in an amount such that approximately one atom of active oxygen is present per atom of dihydrothiazine sulphur. The oxidising agent should preferably be one that results in preferential formation of the 1β-oxide or a mixture of 1α- and 1β- oxides wherein the 1β-oxide predominates. Suitable oxidising agents include metaperiodic acid, peracetic acid, permonophthalic acid and m-chloroperbenzoic acid. Care should be taken to avoid using an excess of oxidising agent which would result in the formation of the 1,1-dioxide.

Compounds of the formula (I) may also be prepared by the oxidation of a ceph-2-em compound to form a ceph-3-em 1-oxide as described in Dutch published Patent Application No. 6910830.

The 1-oxide is preferably formed at a temperature below +10° C to minimise sulphone formation.

The 1-oxide may be formed in solution in an organic solvent and then brominated in the resulting solution after purification. Suitable solvents are described below under BROMINATION in particular the chlorinated hydrocarbons.

The 1-oxide may be formed from a compound of formula (III) where $R^2=H$ and the resulting acid 1-oxide esterified. Alternatively, a preferred ester of formula (III) may be used, for the oxidation step.

BROMINATION

The bromination of the compounds of the general formula I may be effected by any convenient system capable of generating bromine atoms such as bromine itself, or a bromine transfer agent e.g. an N-bromoamide or an N-bromoimide. The N-amide or N-bromoimide may include a cyclic system, the amide or imide linkage forming part of the cyclic system; examples of such N-bromoamides include caprolactam and examples of such N-bromoimides include the 1,3-dibromo-5,5-diloweralkyl hydantoins e.g. 1,3-dibromo-5,5-dimethylhydantoin; 1,3-dibromo-5-ethyl-5-methylhydantoin; 1,3-dibromo-5-isopropyl-5-methylhydantoin, N-bromosuccinimide, N-bromophthalimide etc. Other useful N-bromoamides include N-bromo lower alkanoamides e.g. N-bromoacetamide. Another useful brominating agent is 1,3,5-tribromo-1,2,4-triazole. By reason of their availability, particularly preferred brominating agents include N-bromosuccinimide and 5,5-dimethyl-1,3-dibromohydantoin.

The various brominating agents require initiation in order to generate bromine atoms and suitable initiating systems include free-radical initiators such as azo compounds e.g. azobisisobutyronitrile, peroxides e.g. benzoyl peroxide, irradiation by ultra violet or visible light sources e.g. mercury arcs or tungsten lamps, or by γ-rays emitted by Co⁶⁰ sources.

The brominating agent may be added as such or in suspension or solution in a suitable solvent i.e. a solvent which solubilizes the starting material and which is substantially inert under the conditions of the reaction e.g. a hydrocarbon such as benzene or a halogenated hydrocarbon particularly a chlorinated hydrocarbon e.g. chloroform, methylene chloride, 1,2-dichloroethane etc. The brominating agent is added to a solution or suspension of the cephalosporin compound (I) in a suitable solvent e.g. a halogenated hydrocarbon such as methylene chloride, chloroform, 1,2-dichloroethane or chlorobenzene or a hydrocarbon such as benzene. The bromination may be effected at temperatures ranging from −80° to +150° C e.g. from −20° to +150° C, preferably from −40° to +85° C advantageously from −20° to +85° C. The course of the bromination may be followed by measurement of the consumption of brominating agent and by thin-layer chromatography. The course of the reaction may also be followed by monitoring the ultra violet absorption spectrum or optical rotation.

The bromination is preferably carried out using N-bromosuccinimide or a dibromohydantoin as the brominating agent initiated by ultra violet irradiation at a low temperature e.g. from −20° to +10° C.

The addition of small amounts e.g. up to 5% by volume of water or an aqueous solution or suspension of a weak base such as an alkali metal or alkaline earth metal salt of a weak acid e.g. sodium bicarbonate, sodium carbonate, sodium acetate or calcium carbonate has been found to assist the bromination reaction. In this way the times of initiation and reaction may be reduced and/or the yield of 3-bromomethyl compound may be increased. The aqueous solution or suspension of the weak base is preferably at a pH of 7 to 11.

The bromination may be effected under an inert atmosphere.

The bromination reaction according to the invention lends itself to continuous flow techniques.

The 3-bromomethyl compounds obtained may be converted to other 3-halomethyl compounds viz 3-chloro or 3-iodomethyl compounds, e.g. by reaction with a suitable alkali metal halide, for the conversion of bromomethyl compounds into other halomethyl compounds. Such reactions may occur during operations involving sources of other halide ions.

After completion of the reaction, the 3-bromomethyl compound may then be isolated. An advantageous procedure is to wash the resulting reaction mixture with water to remove by-product imide or amide resulting from the brominating agent which is then isolated, for example by concentration of the solution followed by crystallization of the product or by chromatography. The aqueous solution containing the imide or amide may then be treated with bromine after the addition of alkali to regenerate the brominating agent.

Compounds of general formula:

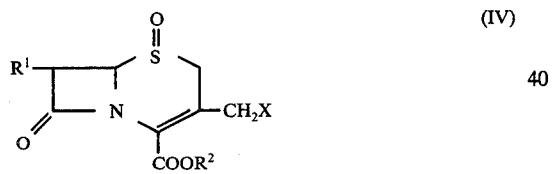

where $R^1$ and $R^2$ have the above defined meanings, and X is bromine, chlorine or iodine are new compounds and are a feature of the invention. Important compounds of formula (IV) include 2,2,2-trichloroethyl 3-bromomethyl-7β-phenylacetamidoceph-3-em-4-carboxylate, 1β-oxide; 2,2,2-trichloroethyl 3-bromomethyl-7β-formamido-ceph-3-em-4-carboxylate, 1β-oxide; t-butyl 3-bromomethyl-7β-formamidoceph-3-em-4-carboxylate, 1β-oxide; 2,2,2-trichloroethyl 3-bromomethyl-7β-phenoxyacetamidoceph-3-em-4-carboxylate, 1β-oxide; 2,2,2trichloroethyl 3-bromomethyl-7β-[D - 2 - (2,2,2-trichloroethoxycarbonylamino) 2-phenylacetamido]ceph-3-em-4-carboxylate, 1β-oxide; p-methoxybenzyl 3-bromomethyl-7β-phenylacetamidoceph-3-em-4-carboxylate, 1β-oxide; t-butyl 3-bromomethyl-7β-phenylacetamidoceph-3-em-4-carboxylate, 1β-oxide; 2,2,2-trichloroethyl 3-bromomethyl-7β-(2,2,2-trichloroethoxycarbonylamino)ceph-3-em-4-carboxylate, 1β-oxide; t-butyl-3-bromomethyl-7β-phenoxyacetamidoceph-3-em-4-carboxylate, 1β-oxide and 2,2,2-trichloroethyl 3-bromomethyl-7β-(DL-2-bromo-2-phenylacetamido)-ceph-3-em-4-carboxylate, 1β-oxide.

In addition to bromination in the 3-methyl group, other bromination reactions may take place. One may thus form as by-products compounds of formula:

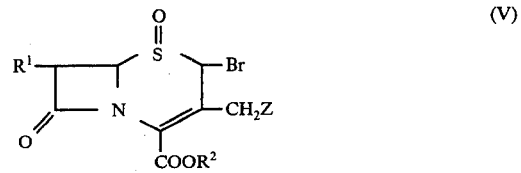

(wherein $R^1$ and $R^2$ have the above defined meanings and Z is hydrogen or bromine). Compounds of formula V where Z=H may be reduced e.g. with Zn/acid to re-form the compound of formula I which may then be re-brominated to yield the desired compound of formula II. Bromination may also occur in the group $R^1$ e.g. in the case where $R^1$ = phenylacetamido to yield 2-bromo-2-phenylacetamido-3-bromomethyl compounds.

ACYL GROUPS

The group $R^1$ in the above formulae may represent a wide variety of acylamido groups which may contain 1–20 carbon atoms. Specific acyl groups are illustrated in the accompanying list which is not intended to be exhaustive:

(i) $R^uC_nH_{2n}CO-$ where $R^u$ is aryl (carbocyclic or heterocyclic), cycloalkyl, substituted aryl, substituted cycloalkyl, cyclohexadienyl, or a non-aromatic or mesoionic group, and n is an integer from 1–4. Examples of this group include phenylacetyl; substituted phenylacetyl e.g. fluorophenylacetyl, nitrophenylacetyl, aminophenylacetyl, acetoxyphenylacetyl, methoxyphenylacetyl, methylphenylacetyl, or hydroxyphenylacetyl; N,N-bis (2-chloroethyl) aminophenylporpionyl; thien-2- and -3-ylacetyl; 4-isoxazolyl and substituted 4-isoxazolylacetyl; pyridylacetyl; tetrazolylacetyl or a sydnoneacetyl group. The substituted 4-isoxazolyl group may be a 3-aryl-5-methyl isoxazol-4-yl group, the aryl group being e.g. phenyl or halophenyl e.g. chloro- or bromo- phenyl. An acyl group of this type is 3-o-chlorophenyl-5-methyl isoxazol-4acetyl.

(ii) $C_nH_{2n+1}CO-$ where n is an integer from 1–7. The alkyl group may be straight or branched and, if desired, may be interrupted by an oxygen or sulphur atom or substituted by e.g. a cyano group, a carboxy group, an alkoxycarbonyl group, a hydroxy group or a carboxycarbonyl group (—CO.-COOH). Examples of such groups include cyanoacetyl, hexanoyl, heptanoyl, octanoyl and butylthioacetyl.

(iii) $C_nH_{2n-1}CO-$ where n is an integer from 2–7. The alkenyl group may be straight or branched and, if desired, may be interrupted by an oxygen or a sulphur atom. An example of such a group is allylthioacetyl.

(iv)

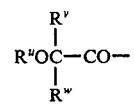

where $R^u$ has the meaning defined under (i) and in addition may be benzyl, and $R^v$ and $R^w$ which may be the same or different each represent hydrogen, phenyl, benzyl, phenethyl or lower alkyl. Examples of such groups include phenoxyacetyl, 2-phenoxy-2-phenylacetyl, phenoxypropionyl, 2-phenoxybutyryl benzyloxycarbonyl, 2-phenoxypropionyl, 2-phenoxybutyryl, methylthiophenoxyacetyl.

(v)

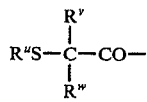

where $R^u$ has the meaning defined under (i) and, in addition, may be benzyl and $R^v$ and $R^w$ have the meanings defined under (iv). Examples of such groups include S-phenylthioacetyl, S-chlorophenylthioacetyl, S-fluorophenylthioacetyl, pyridylthioacetyl, and S-benzylthioacetyl.

(vi) $R^u Z(CH_2)_m CO-$ where $R^u$ has the meaning defined under (i) and, in addition, may be benzyl, Z is an oxygen or sulphur atom and m is an integer from 2-5. An example of such a group is S-benzylthiopropionyl.

(vii) $R^u CO-$ where $R^u$ has the meaning defined under (i). Examples of such groups include benzoyl, substituted benzoyl (e.g. aminobenzoyl), 4-isoxazolyl- and substituted 4-isoxazolylcarbonyl, cyclopentanecarbonyl, sydnonecarbonyl, naphthoyl and substituted naphthoyl (e.g. 2-ethoxynaphthoyl) quinoxalinylcarbonyl and substituted quinoxalinylcarbonyl (e.g. 3-carboxy-2-quinoxalinylcarbonyl). Other possible substituents for benzoyl include alkyl, alkoxy, phenyl, carboxy, alkylamido, cycloalkylamido, allylamido, phenyl(lower)alkyl amido, morpholinocarbonyl, pyrrolidinocarbonyl, piperidinocarbonyl, tetrahydropyridino, furfurylamido or N-alkyl-N-anilino, or derivatives thereof, and such substitutents may be in the 2- or 2- and 6-positions. Examples of such substituted benzoyl groups are 2,6-dimethoxybenzoyl, 2-methylamidobenzoyl and 2-carboxybenzoyl. Where the group $R^u$ represents a substituted 4-isoxazolyl group, the substituents may be as set out above under (i). Examples of such 4-isoxazolyl groups are 3-phenyl-5-methyl-isoxazol-4yl carbonyl, 3o-chlorophenyl-5-methyl-isoxazol-4-yl carbonyl and 3-(2,6-dichlorophenyl)-5-methyl-isoxazol-4-yl carbonyl.

(viii)

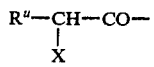

where $R^u$ has the meaning defined under (i) and X is amino, substituted amino (e.g. acylamido or a group obtained by reacting the α-aminoacylamido group of the 7-side chain with an aldehyde or ketone e.g. acetone, methylethylketone or ethyl acetoacetate), hydroxy, carboxy, esterified carboxy, triazolyl, tetrazolyl, cyano, halogeno, acyloxy (e.g. formyloxy or lower alkanoyloxy) or etherified hydroxy group. Examples of such acyl groups are α-aminophenylacetyl, and α-carboxyphenyl-acetyl.

(ix)

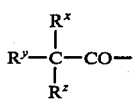

where $R^x$, $R^y$ and $R^z$ which may be the same or different may each represent lower alkyl, phenyl or substituted phenyl or $R^x$ represents hydrogen. An example of such an acyl group is triphenylcarbonyl (x)

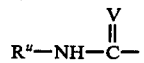

where $R^u$ has the meaning defined under (i) and in addition may be hydrogen, lower alkyl or halogen substituted lower alkyl, and Y represents oxygen or sulphur. An example of such a group is $Cl(CH_2)_2 NHCO$.

(xi)

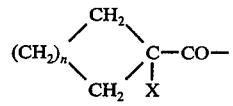

where X has the meaning defined under (viii) above and n is an integer of from 1 to 4. An example of such an acyl group is 1-aminocyclohexanecarbonyl.

(xii) Amino acyl, for example $R^w CH(NH_2).(CH_2)_n CO-$ where n is an integer from 1–10, or $NH_2 \cdot C_n H_{2n} Ar(CH_2)_m CO$, where m is zero or an integer from 1–10, and n is 0, 1 or 2, $R^w$ is a hydrogen atom or an alkyl, aralkyl or carboxy group or a group as defined under $R^u$ above, and Ar is an arylene group, e.g. p-phenylene or 1,4-naphthylene. Examples of such groups are disclosed in British Patent Specification No. 1,054,806. A group of this type is the p-aminophenylacetyl group. Other acyl groups of this type include those, e.g. δ-aminodipoyl, derived from naturally occurring amino acids and derivatives thereof e.g. N-benzoyl γ-aminodipoyl.

(xiii) Substituted glyoxylyl groups of the formula $R^y.CO.CO-$ where $R^y$ is an aliphatic, araliphatic or aromatic group, e.g. a thienyl group, a phenyl group, or a mono-, di- or tri- substituted phenyl group, the substituents being, for example, one or more halogen atoms (F, Cl, Br, or I), methoxy groups, methyl groups or amino groups, or a fused benzene ring. Included in this group are also the α-carbonyl derivatives of the above substituted glyoxylyl groups, formed for example with hydroxylamine, semicarbazide, thiosemicarbazide, isoniazide or hydrazine.

(xiv) Formyl.

(xv) Hydrocarbyloxycarbonyl and substituted hydrocarbyloxy groups (wherein the 7-amino group forms part of a urethane), in particular lower alkoxycarbonyl groups (such as methoxycarbonyl, ethoxycarbonyl and, most preferably, t-butoxycarbonyl groups); halo lower alkoxycarbonyl groups e.g. 2,2,2-trichloroethoxycarbonyl; aralkoxycarbonyl groups such as benzyloxycarbonyl, 4-methoxybenzyloxycarbonyl, diphenylmethoxycarbonyl and 4-nitrobenzyloxycarbonyl groups. Cycloalkoxycarbonyl groups are also advantageous, especially the adamantyloxycarbonyl group.

(xvi) Haloformyl e.g. chloroformyl.

DISPLACEMENT WITH NUCLEOPHILES

Compounds of general formula IV may, for example, be reacted with an alkali metal salt of a lower aliphatic acid e.g. potassium acetate, for example by heating in acetone, or in the cold with N,N-dimethylformamide, to yield a compound of the general formula:

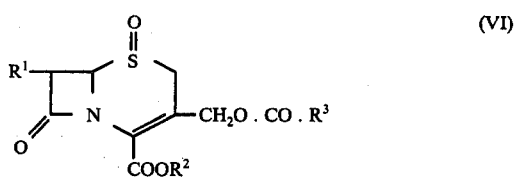
(VI)

where $R^1$ and $R^2$ have the above defined meanings and $R^3COOH$ is a lower aliphatic acid. The use of an alkali metal salt of a lower aliphatic acid is however only an example of a range of compounds having a nucleophilic atom, e.g. nitrogen, carbon, sulphur or oxygen which may be employed under conditions which are effective to displace the group X by the nucleophile. Reactions of this type may have advantages over conventional nucleophilic reactions involving acetates in cephalosporin C type compounds. Nucleophilic substances which may be used have been widely described in earlier literature and patents pertaining to cephalosporin chemistry. Examples of such nucleophiles include:

NITROGEN NUCLEOPHILES

Examples of nitrogen nucleophiles include tertiary aliphatic, aromatic, araliphatic and cyclic amines including trialkylamines, for example, triethylamine, pyridine bases such as pyridine and alkyl pyridines; heterocyclic amines having more than one heteroatom, at least one heteroatom being nitrogen, such as pyrimidines, purines, pyridazines, pyrazines, pyrazoles, imidazoles, triazoles and thiazoles.

Thus the term "nitrogen nucleophile" includes compounds of the following formulae:

$NR^aR^bR^c$ (a)

in which $R^a$, $R^b$ and $R^c$, which may be the same or different are hydrogen atoms or substituted or unsubstituted e.g. lower alkyl aliphatic, araliphatic e.g. benzyl or aromatic e.g. phenyl, groups; any two together with the nitrogen atom if desired forming a heterocyclic ring which may be interrupted by one or more further hetero-atoms. Examples of such compounds include N-methylaniline, piperidine morpholine, etc.

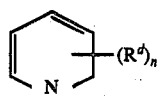
(b)

in which n is 0 or an integer from 1 to 5 and $R^d$, which when n is from 2 to 5, may be the same or different, is an aliphatic, e.g. lower alkyl such as methyl, ethyl, n-propyl, iso-propyl etc; an aryl e.g. phenyl; an araliphatic, e.g. phenyl lower alkyl such as benzyl, phenylethyl etc; or an alkoxymethyl e.g. methoxymethyl, ethoxymethyl, n-propoxymethyl, iso-propoxymethyl etc; or acyloxymethyl e.g. alkanoyloxymethyl such as acetoxymethyl; formyl; carbamoyl; acyloxy e.g. alkanoyloxy such as acetoxy; esterified carboxyl; alkoxy e.g. methoxy, ethoxy, n-propoxy, iso-propoxy etc; aryloxy e.g. phenoxy; aralkoxy e.g. benzyloxy; alkylthio e.g. methylthio, ethylthio; arylthio; aralkylthio; cyano; hydroxy; N-monoloweralkylcarbamoyl e.g. N-methylcarbamoyl, N-ethylcarbamoyl etc; N,N-diloweralkylcarbamoyl e.g. N,N-dimethylcarbamoyl, N,N-diethylcarbamoyl etc; N-(hydroxyloweralkyl) carbamoyl e.g. N-(hydroxymethylcarbamoyl, N-(hydroxyethyl)carbamoyl etc; or carbamoylloweralkyl e.g. carbamoylmethyl, carbamoylethyl etc. group.

(c)

in which $R^d$ is as defined in (b) and m is 0 or an integer from 1 to 4,

(d)

in which $R^d$ and m are as defined in (c),

(e)

in which $R^d$ and m are as defined in (c),

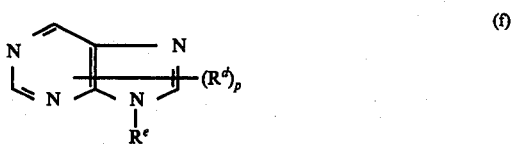
(f)

in which $R^d$ is as defined in (b), p is 0 or an integer from 1 to 3, and $R^e$ is an aliphatic, araliphatic, aryl, or acyl radical or a hydrogen atom.

(g)

in which $R^d$, $R^e$ and p are as defined in (f),

(h)

in which $R^d$, $R^e$ and p are as defined in (f),

(i)

in which $R^d$ and $R^e$ are as defined in (f) and q is 0, 1 or 2,

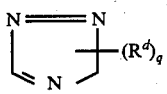
(j)

in which R$^d$ and q are as defined in (i)

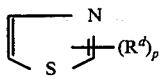
(k)

in which R$^d$ and p are as defined in (f), and

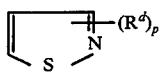
(l)

in which R$^d$ and p are as defined in (f).

(m) azides e.g. alkali metal azides.

CARBON NUCLEOPHILES

Examples of "carbon nucleophiles" include inorganic cyanides, pyrroles and substituted pyrroles, e.g. indoles, and compounds giving stabilised carbanions, for example, acetylenes and compounds having β-diketone groups, for example, acetoacetic and malonic esters and cyclohexane-1,3-diones or enamines, ynamines or enols.

Thus the term "carbon nucleophile" includes compounds of the following formulae:

$$M^{\nu+}(CN)_\nu^-  \qquad (a')$$

in which M is a metal cation, preferably an alkali metal or alkaline earth metal cation or a quaternary ammonium ion, and ν is the valency of the cation.

(b')

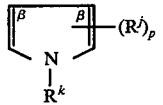

in which R$^j$ is an aliphatic, araliphatic or aryl group or an esterified carboxy, acyloxy or acyl group, p is 0 or an integer from 1 to 3, and R$^k$ is an alkyl, aralkyl, or aryl group or a hydrogen atom, at least one of the β-positions being unsubstituted, (c')

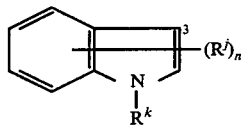

in which R$^j$ and R$^k$ are as defined in (b') and n is 0 or an integer from 1 to 5, the 3-position being unsubstituted,
(d')

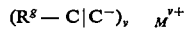
$(R^s — C|C^-)_\nu \quad M^{\nu+}$ in which R$^s$ is an aliphatic, araliphatic or aryl group or a hydrogen atom, and M and ν are as defined in (a')

(e')

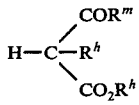

in which the groups R$^h$, which may be the same or different, are hydrogen atoms or alkyl, aralkyl or aryl groups and R$^m$ is an alkyl, aralkyl, aryl, alkoxy, aralkoxy or aryloxy group.

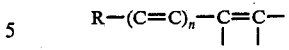
(f)

where R is an electron donating group or atom and n is 0 or an integer of from 1 to 5.

SULPHUR NUCLEOPHILES

Examples of "sulphur nucleophiles" include thiourea and aliphatic, aromatic, araliphatic, alicyclic and heterocyclic substituted thioureas; dithiocarbamates; aromatic, aliphatic and cyclic thioamides, for example thioacetamide and thiosemicarbazide; thiosulphates; thiols; thiophenols; thioacids, e.g. thiobenzoic acid or thiopicolinic acid; and dithioacids.

Thus the term "sulphur nucleophile" includes compounds of the formulae:

$$R^1R^2N — CS — NR^3R^4 \qquad (a'')$$

in which R$^1$, R$^2$, R$^3$ and R$^4$, which may be the same or different may each represent a hydrogen atom, an aliphatic e.g. lower alkyl such as methyl, ethyl, n-propyl etc. group; an alicyclic e.g. cyclohexyl, cyclopentyl etc. group; an aromatic e.g. phenyl, naphthyl etc. group; an araliphatic e.g. benzyl group; or a heterocyclic group; or R$^1$ and R$^3$ together form a divalent group. R$^2$ or R$^4$ may alternatively be a group —NR$^1$R$^3$ where R$^1$ and R$^3$ are as defined above.

HR$^q$.CS.NR$^r$R$^s$  (b'')

in which R$^q$ is a straight or branched chain aliphatic or araliphatic group, and R$^r$ and R$^s$, which may be the same or different, may each represent a hydrogen atom or an aliphatic group e.g. lower alkyl such as methyl, ethyl, n-propyl etc. group; an araliphatic e.g. benzyl group; an acyl e.g. a lower alkanoyl such as acetyl etc. group or an aryl e.g. phenyl, naphthyl etc. group.

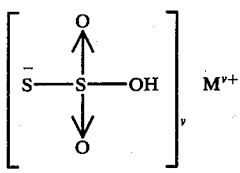
(C'')

in which M is a metal cation, preferably an alkali or alkaline earth metal cation, or a quaternary ammonium ion, and ν is the valency of the cation.

R$^1$.S(O)$_n$H  (d'')

in which R$^1$ has the above defind meaning, e.g. lower alkyl, and n is 0, 1 or 2. A preferred class of nucleophiles falling within the above formula (d'') are those having the general formula

R$^a$SH in which R$^a$ is an aliphatic e.g. lower alkyl e.g. methyl, ethyl, n-propyl etc.; araliphatic, e.g. phenyl lower alkyl e.g. benzyl, phenylethyl etc. or substituted phenyl lowe alkyl; alicylic e.g. cycloalkyl e.g. cyclopentyl or cyclohexyl; aromatic e.g. phenyl or substituted phenyl or heterocyclic group e.g. 5-methyl-1,3,4-thiadiazol-2-yl.

OXYGEN NUCLEOPHILES

Examples of oxygen nucleophiles include water, alcohols, for example alkanols such as methanol, ethanol, propanol and butanol and lower alkanoic acids. Water furnishes both $H_2O$: and $OH^-$ and is thus a competitor nucleophile in any reaction occurring in aqueous medium.

The term "oxygen nucleophile" thus includes compounds of the following formula:

$$R'(CO)_nOH$$

in which the group $R'$ may be lower alkyl (e.g. methyl, ethyl, n-propyl, isopropyl, n-butyl, isobutyl etc.); lower alkenyl (e.g. allyl); lower alkynyl (e.g. propynyl, etc.); lower cycloalkyl (e.g. cyclopentyl, cyclohexyl, etc); lower cycloalkyl lower alkyl (e.g. cyclopentylmethyl, cyclohexylethyl etc.); aryl (e.g. phenyl or naphthyl); aryl lower alkyl (e.g. benzyl); heterocyclic; heterocyclic lower alkyl (e.g. furfuryl) or any of these groups substituted by, for example, one or more of lower alkoxy (methoxy, ethoxy, etc.), lower alkylthio (methylthio, ethylthio, etc), halogen (chlorine, bromine, iodine or fluorine), lower alkyl (methyl, ethyl etc), nitro, hydroxy, acyloxy, carboxy, carbalkoxy, lower alkylcarbonyl, lower alkylsulphonyl, lower alkoxysulphonyl, aino, lower alkylamino or acylamino groups; and $n$ is 0 or 1. Where the oxygen nucleophile is an acid this will generally be employed as a salt with an inorganic or organic base. Such salts include alkali metal e.g. sodium or potassium or trialkylammonium e.g. triethylammonium.

Reactions with nucleophiles, particularly oxygen nucleophiles, may be facilitated by the presence of a salt of mercury, silver or gold, preferably mercury. We particularly prefer to use mercuric ($Hg^{++}$) salts. The efficacy of the reaction is also dependent on other factors including the nature of the anion of the salt, the type of cations which it produces in aqueous solution and the solubility of the salt in the reaction medium which, whenever the nucleophile is a lower alkanol, is conveniently the latter itself.

The metal salt is advantageously one of the formula $HgD_2$ or $HgD$ which furnishes $Hg^{++}$ and/or $HgD^+$ cations, preferably the former, in aqueous solution, $D^-$ being a weakly nucleophilic anion; a like-acting salt $Hg_nE_2$ of mercury with a di- or polyvalent anion where E is an n-valent anion, $n$ being 2 or greater, or a salt of the formula $Ag_mF$ where F is an m-valent anion of a weakly nucleophilic nature and $m$ and 1 or greater.

The anion of the salt should be substantially non-oxidising to compound (IV) under the conditions of the reaction and should preferably be an anion of a strong acid, i.e. an acid having a pKa value in aqueous solution of less than 2, to facilitate formation of the desired cations.

Nucleophilic properties in the anion may complete with those in the chosen nucleophile; therefore it is desirable that the anion having a nucleophilic constant less than that of the acetate ion for conventional one-step nucleophilic displacement in aqueous media at a tetrahedral carbon centre (see, for example, Hine's "Physical Organic Chemistry" McGraw-Hill, 1962 pp 159-161). Mercuric salts with anions of nucleophilic constant less than acetate generally promote fast reactions of the required type. Mercuric and silver salts with the attributes described above include the perchlorate, nitrate, trifluoroacetate and tetrafluoroborate. Mercurous perchlorate also possesses the desired properties.

The metal salt will normally be used in an amount at least equivalent to the compound of formula (IV).

REACTION CONDITIONS FOR THE DISPLACEMENT OF X BY THE NUCLEOPHILE

The displacement of X in compounds of formula (IV) by the nucleophile may conveniently be effected by maintaining the reactants in solution or suspension at a moderate temperature, e.g. from $-40°$ to $+120°$ C such as from $0°$ to $+120°$ C preferably from $-20$ to $+35°$ C e.g. from 0 to $+35°$ C advantageously at ambient temperature. Reactions are usually complete for the replacement of bromine by pyridine in N,N-dimethylformamide in about 2 hours at 20° C and in correspondingly longer times at lower temperatures or correspondingly shorter times at higher temperatures.

The nucleophile displacement reactions may be facilitated by the addition of an acid acceptor such as an organic base which promotes the formation of the nucleophile anion in the form of a salt. Suitable organic bases include tri (lower alkyl)amines e.g. triethylamine. However, reactions with tertiary nitrogen nucleophiles in general do not require an acid acceptor.

The reaction is advantageously effected using from one to ten molar equivalents of incoming nucleophile. The pH value of the reaction solution under aqueous conditions is advantageously maintained within the limits 5 - 8. When working under non-aqueous conditions, the reaction medium should be neither extremely basic nor extremely acidic.

Organic solvents such as dioxan, ethyl acetate, formamide, N,N-dimethylformamide or acetone may be employed. The organic solvents may be used in the presence or absence of water. In certain cases the nucleophile itself may be the solvent e.g. when the nucleophile is pyridine or a lower alcohol.

Organic media whic may be used include lower alkanoic acid nitriles e.g. acetonitrile or propionitrile; halogenated hydrocarbons e.g. methylene chloride, chloroform, ethylene dichloride or perchloroethylene; hydrocarbons e.g. benzene; cyclic ethers e.g. dioxan or tetrahydrofuran; amides of the general formula $R^5.CO.NR^6R^7$ where $R^5$ is a hydrogen atom or an alkyl group containing 1 to 5 carbon atoms and $R^6$ and $R^7$, which may be the same or different, are each a hydrogen atom or an alkyl group containing 1 to 5 carbon atoms, or, alternatively $R^6$ and $R^7$ together form a divalent aliphatic group which, together with the adjacent nitrogen atom, forms a heterocyclic ring. Examples of amides of this type are N,N-dimethylformamide, N,N-diethylformamide, N,N-dimethylacetamide, formamide and N-methylformamide. Other solvents which may be used include N-lower alkyl pyrrolidones e.g. N-methylpyrrolidone and di-lower alkyl sulphoxides, e.g. dimethylsulphoxide.

The reaction medium need not be liquid at room temperature. Solids, e.g. acetamide, may be used so long as they are liquid at the reaction temperature.

The reaction product may be separated from the reaction mixture, which may contain, for example, unchanged cephalosporin and other substances, by a variety of processes including recrystallization, ionophoresis, paper chromatogrphy or by chromatography on ion-exchange resins.

After the introduction of the desired nucleophilic group the 1-sulphinyl group may be reduced by any convenient means. This may, for example, be effected by reduction of the corresponding acyloxysulphonium or alkyloxysulphonium salt prepared in situ by reaction with e.g. acetyl chloride in the case of an acetoxy-sulphonium salt, reduction being effected by, for example, sodium dithionite or by iodide ion as in a solution of potassium iodide in a water miscible solvent e.g. acetic acid, tetrahydrofuran, dioxan, dimethylformamide or dimethylacetamide. The reaction may be effected at a temperature of $-20°$ to $+50°$ C.

Alternatively, reduction of the 1-sulphinyl group may be effected by phosphorus trichloride or tribromide in solvents such as methylene chloride, dimethylformamide or tetrahydrofuran, preferably at a temprature of $-20°$ to $+50°$ C.

It will be observed from the foregoing that the $\Delta^3$ unsaturation has not been subject to isomerisation throughout the sequence of reactions described. This is an important feature of the invention.

Alternatively, the compound of general formula (IV) may be first reduced in like manner to form a compound of general formula:

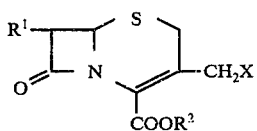

(VII)

wherein $R^1$, $R^2$ and X have the above defined meanings, which may then be reacted with a nucleophile as directed above. This step may however give rise to $\Delta^3 \rightarrow \Delta^2$ isomerisation.

Where the group $R^2$ is the residue of an alcohol or phenol this may be removed at any convenient stage of the synthesis by the methods indicated above. Protection of the 4-carboxyl may be required in some of the stages and the exact point of removal will depend on this factor. Should the group $R^2$ be removed during a specific reaction it may be necessary to re-esterify the carboxyl group if protection is subsequently necessary.

When the group $R^2$ is removed after the introduction of a nitrogen nucleophile, particularly a nitrogen nucleophile of (b) above, the resulting compound may conveniently be recovered as a quaternary ammonium salt e.g. the hydronitrate. The resulting salt may then be converted to the free betaine by the methods described in British Pat. Nos. 1,101,561 or 1,101,562.

Where at any stage the product of a 7β-acylamido compound not having the desired acyl group, the 7β-acylamido compound may be N-deacylated to yield the corresonding 7β-amino compound and the latter acylated with an appropriate acylating reagent.

Suitable methods of N-deacylating cephalosporin derivatives having 7β-acylamido groups are described in British Pat. Nos. 1,041,985 and 1,119,806; Belgian Pat. No. 719,712 and in South African Pat. Specifications Nos. 68/5048 and 68/5327. Another method of N-deacylation which may be used is acid catalysis. For example, N-deformylation of a 7β-formamido group may be effected with a mineral acid at a temperature of minus 15° to $+100°$ C, preferably $+15$ to 40° C. A convenient reagent for the N-deformylation is concentraed hydrochloric acid in methanol, dioxan or tetrahydrofuran. Alternativey N-deformylation may be effected with the aid of a Lewis acid in a lower alkanol or a lower alkane diol, under substantially anhydrous conditions. N-deformylation under such substantially anhydrous conditions may be effected at a temperature of from $-40°$ to $+100°$ C advantageously at from $-20°$ to $+70°$ C.

The 7β-amino compound may be separated as an insoluble salt e.g. a hydrochloride or a hydrogen p-toluene sulphonate or it may be precipitated by adjustment of the pH (e.g. to an isoelectric point), if necessary by extraction with a suitable solvent. The 7β-amino compound may then be reacylated. Reacylation can then be effected with the acylating agent of choice. A wide variety of acylating agents for use in the cephalosporin field have been described in the literature.

When the 7β-acylamido group contains an amino group it will be necessary to protect this during the various reaction stages. The protecting group is conveniently one which can be removed by hydrolysis without affecting the rest of the molecule, especially the lactam and 7β-amido linkages. The amine protecting group and the esterifying group at the 4—COOH position can be removed using the same reagent. An advantageous procedure is to remove both groups at the last stage in the sequence. Protected amine groups include urethane, arylmethyl (e.g. trityl) amino, or sulphenylamino types. Such groups can in general be removed by one or more reagents selected from dilute mineral acids e.g. dilute hydrochloric acid, concentrated organic acids, e.g. concentrated acetic acid, trifluoroacetic acid, and liquid hydrogen bromide at very low temperatures, e.g. $-80°$ C. A convenient protecting group is the t-butoxycarbonyl group, which is radily removed by hydrolysis with dilute mineral acid, e.g. dilute hydrochloric acid, or preferably with a strong organic acid (e.g. formic acid or trifluoroacetic acid) e.g. at a temperature of 0–40° C., preferably at room temperature (15–25° C). Another convenient protecting group is the 2,2,2-trichloroethoxycarbonyl group which may be split off by an agent such as zinc/acetic acid, zinc/formic acid, zinc/lower alcohols or zinc/pyridine.

According to one embodiment of the invention the reactions described above may be proceeded with via the following sequence of steps wherein $R^1$ and $R^2$ have the above defined meanings, $R^{10}CO$ is the final acyl group and Y is the residue of the nucleophile.

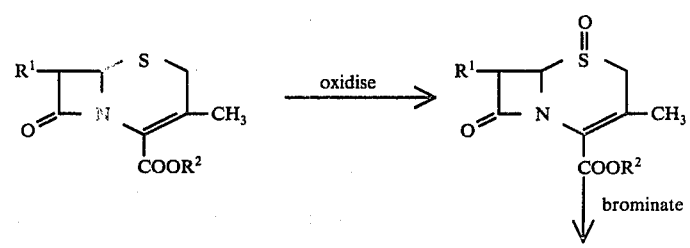

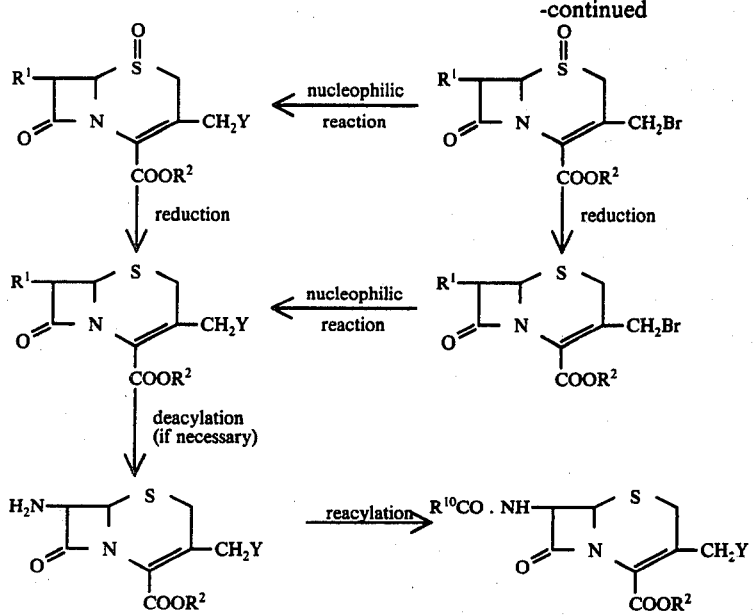

After the formation of the —CH$_2$Br group, the bromine may be exchanged for iodine or chlorine to yield the analogous —CH$_2$I or CH$_2$Cl compounds. The latter may then be subjected to the nucleophilic reaction, similar considerations also applying to the reaction schemes set out below.

An advantageous embodiment of the process according to the invention involves the following sequence of reactions:

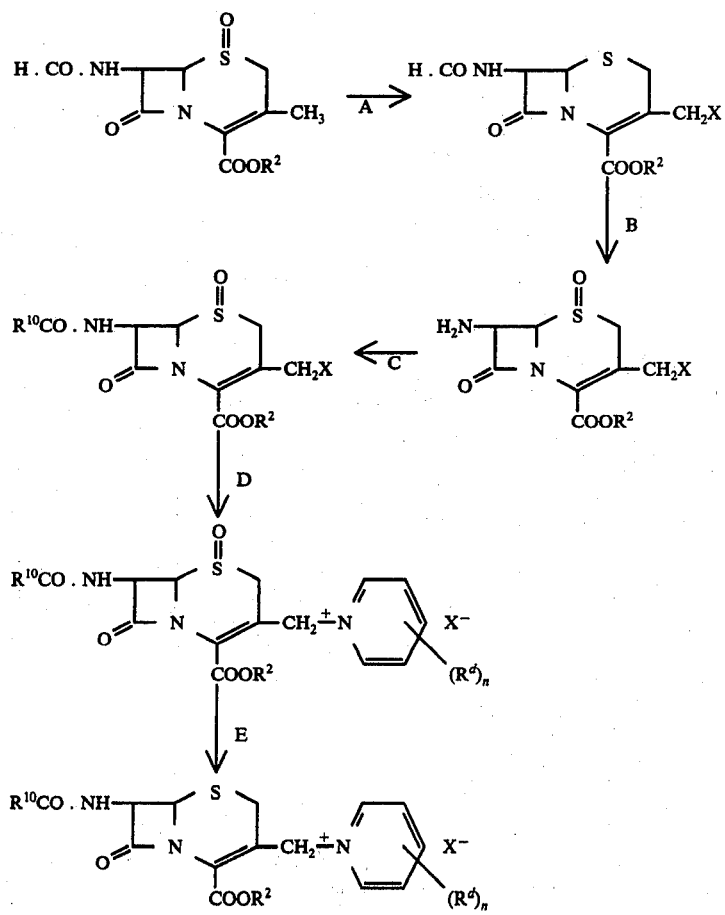

wherein X, R$^2$, R$^d$ and n have the above defined meanings, and R$^{10}$CO is the final acyl group.

The above sequence is advantageous for a number of reasons: (1) step A involving the bromination of the 3-methyl group, followed if desired by halogen transfer, can be effected without substantial attack of the formamido group which might be the case with $R^{10}CO$ e.g. when it is 2-thienylacetyl; (2) step B involving N-deformylation can be effected readily; (3) step C involving the introduction of the final acyl group $R^{10}CO$ is effected before step D which might otherwise be disadvantageous and (4) retention of the oxide group until step D is complete minimises $\Delta^3 \rightarrow \Delta^2$ isomerisation which would otherwise tend to occur in the presence of the pyridine nucleophile. By proceeding in this manner we are able to arrive at a satisfactory route to the compounds of general formula (VIII) defined below.

Another advantageous embodiment of the process according to the invention involves the following sequence of reaction steps:

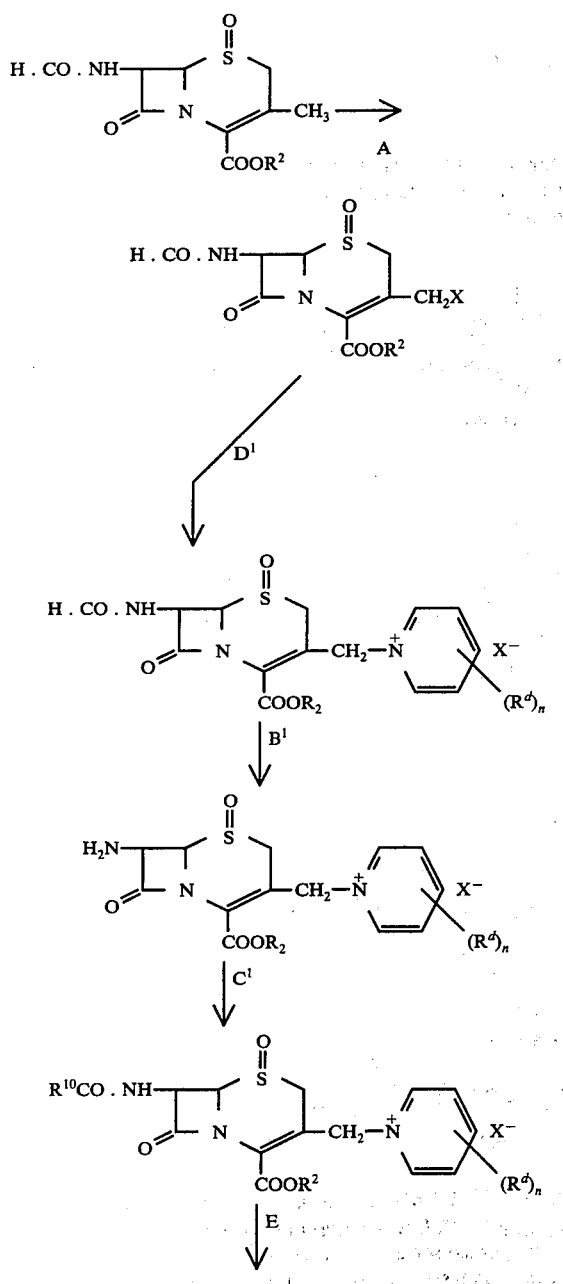

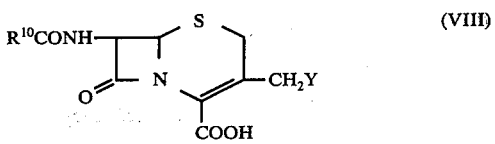

The sequence with steps A, $B^1$ and $D^1$ affords similar advantages to that described for the earlier sequence with steps A, B and D.

The present invention provides a significant, alternative route to those already known for preparing compounds of formula (VIII) below.

Compounds of the general formula $$R^{10}CONH\text{—}[\beta\text{-lactam-S-CH}_2Y]\text{—COOH} \quad \text{(VIII)}$$

where $R^{10}CO$ is an acyl group and Y is the residue of a nucleophile and their salts in general possess antibacterial activity.

Important members of formula (VIII) which may be prepared by the process according to the invention include cephaloram, cephalothin, cephaloridine, cefazolin, cephaloglycine, 7β-(D-2-amino-2-phenylacetamido)-3-methylthiomethylceph-3-em-4-carboxylic acid, 7β-(D-2-amino-2-phenylacetamido)-3-methoxymethylceph-3-em-4-carboxylic acid and N-[7β-(2-thienylacetamido)ceph-3-em-3-ylmethyl]-4-(N-hydroxymethylcarbamoyl)pyridinium-4-carboxylate.

In order that the invention may be well understood the following Preparations and Examples are given by way of illustration only. In the Preparations and Examples, unless otherwise stated, (1) ultra-violet (UV) spectra were measured onsolutions in ethanol,
(2) infra-red (IR) spectra were measured on mulls in Nujol,
(3) proton magnetic resonance (PMR) spectra were determined at 60 or 100 MHz as 5–10% solutions in dimethylsulphoxide-$d_6$.

The signs of coupling constants (J) are not assigned. Signals are assigned as singlets (s), doublets (d), double doublets (dd), triplets (t), AB-quartets (AB-q) or multiplets (m).

(4) optical rotations were determined at 19° to 30° at concentrations in the range 0.8 to 1.2% as solutions in dimethylsulphoxide,
(5) solutions were dried over anhydrous magnesium sulphate,
(6) light petroleum was a fraction, b.p. 60°–80°,
(7) all grades of kieselgel G were supplied by Merck AG, Darmstadt, Germany,
(8) methylene chloride was dried by passage through basic alumina (Woelm, activity I); N,N-dimethylformamide was dried by distillation over acidic alumina (Woelm, activity I).
(9) paper electrophoresis was performed on Whatman No. 3 MM paper at 30 v/cm in pH 1.9 buffer consisting of formic acid (16.7 ml, 98%), acetic acid (84 ml), acetone (105 ml) and water (495 ml) or where indicated with a dilution of this buffer to pH 2.2 with four volumes of water. Spots were located by visual examination with a Hanovia "Chromatolite" ultraviolet lamp. $R_c$ values represent movement with respect to N-[7β-(2-thienylacetamido)ceph-3-em-3-ylmethyl] pyridinium-4-carboxylate (cephaloridine), $R_c$ 1.00, as standard; vitamin $B_{12}$ served as an uncharged marker.

The Examples are divided into four sections:

SECTION A relates to the preparation of starting materials of formula I;

SECTION B relates to the bromination of compounds of formula I to yield compounds of formula II;

SECTION C relates to the conversion of the resulting 3-bromomethyl compounds into their 3-iodomethyl and 3-chloromethyl analogues; and SECTION D relates to nucleophilic displacement and subsequent reactions using the products of Sections B and C. This section illustrates the use of alkanoate, nitrogen, sulphur and alkanol nucleophiles.

SECTION A.

Preparation A1

Methyl 3-methyl-7β-phenylacetamidoceph-3-em-4-carboxylate 1β-oxide (a) Methyl 3-Methyl-7β-phenylacetamidoceph-3-em-4-carboxylate A solution of methyl 6β-phenylacetamidopenicillanate 1β-oxide (29.15 g., 80 mmole) in dry dioxan (600 ml.) containing pyridine (1.26 g., 16 mmole) and 89%-phorphoranic acid (1.76 g., 16 mmole) was refluxed for 15.5 hr. The condensed vapours were dried by passage through a bed of molecular sieves (Linde 4A, 1/16 inch; 40 g.) in dry dioxan (ca. 50 ml.) before returning to the reaction mixture, whose volume remained constant at ca. 600 ml. The cooled reaction solution was evaporated in vacuo and the residue dissolved in methylene chloride (500 ml.), then successively washed with water, 2N-hydrochloric acid, water, 3%-aqueous sodium hydrogen carbonate and water (200 ml. of each), dried and evaporated to a solid which crystallised from industrial methylated spirits to provide the title compound as white prisms (18.3 g., 66%), m.p. 196°-198°, $[\alpha]_D + 136°$ (dioxan), $\lambda_{max}$ 259 nm (ε 6,550). Refrigeration of the liquors provided further identical material (1.85 g., 6.7%). Recrystallisation of a small portion of the above solid provided the analytical sample, m.p. 196°-198.5°, $\nu_{max}$ (CHBr$_3$) 3410 (NH), 1775 (azetidin-2-one), 1720 and 1240 (CO$_2$CH$_3$) and 1670 cm.$^{-1}$ (CONH); τ 0.98 (1H, d, J 8Hz; N$\underline{H}$), 2.73 (5H, s; C$_6$$\underline{H}_5$), 4.39 (1H, dd, J 4.5 and 8 Hz; C$_7$-$\underline{H}$), 4.95 (1H, d, J 4.5 Hz; C$_6$-$\underline{H}$), 6.25 (3H, s; CO$_2$C$\underline{H}_3$), 6.37 and 6.69 (2H, partly obscured AB-q, J 18 Hz; C$_2$-C$\underline{H}_2$) 6.46 (2H, s; C$_6$H$_5$C$\underline{H}_2$) and 7.96 (3H, s; C$_3$-C$\underline{H}_3$) (Found: C, 58.7; H, 5.2; N, 7.9; S, 9.25. C$_{17}$H$_{18}$N$_2$O$_4$S (346.4) requires C, 58.9; H, 5.2; N, 8.1; S, 9.3%).

(b) Oxidation of methyl 3-methyl-7β-phenylacetamidoceph-3-em-4-carboxylate (i) With peracetic acid.

A magnetically stirred solution of methyl 3-methyl-7β-phenylacetamidoceph-3-em-4-carboxylate (6.93 g., 20 mmole) in methylene chloride (100 ml.) was treated with ca. 10% peracetic acid solution (38 ml., ca. 50 mmole) dropwise over 15 min. After a further 15 min. stirring, the mixture was treated cautiously with aqueous 3%-sodium hydrogen carbonate (150 ml.) causing the precipitation of a white solid. This was collected by filtration, dissolved in methylene chloride (600 ml.), and added to the organic portion of the original filtrate. The aqueous portion of the filtrate was back-extracted with methylene chloride (150 ml.) which was then bulked with above extracts. The combined organic extracts were washed with saturated aqueous sodium hydrogen carbonate (150 ml.), saturated brine (200 ml.), then dried and evaporated to low bulk to give methyl 3-methyl-7β-phenylacetamidoceph-3-em-4-carboxylate, 1β-oxide (5.65 g., 78%), as white feathery needles, m.p. 226°-227°, $[\alpha]_D + 183°$, $\lambda_{max}$ 265 nm (ε 8,150). Concentration of the liquors afforded an additional crop of identical material (0.69 g., 10%). Thin-layer chromatographic and spectral analysis indicated the above sulphoxide to be a single diastereoisomer $R_F$ 0.45 (Merck coated silica gel with acetone: methylene chloride = 1:4); $\nu_{max}$ (CHBr$_3$) 3310 (NH), 1780 (azetidin-2-one), 1728 (CO$_2$CH$_3$), 1646 and 1540 (CONH) and 1030 cm.$^{-1}$ (S→O); τ 1.71 (1H, d, J 8 Hz; N$\underline{H}$), 2.67 (5H, s; C$_6$$\underline{H}_5$), 4.20 (1H, dd, J 5 and 8 Hz; C$_7$-$\underline{H}$), 5.10 (1H, d, J 5 Hz; C$_6$-$\underline{H}$), 6.18 (3H, s; CO$_2$C$\underline{H}_3$), ca. 6.3 (4H, unresolved multiplet; C$_6$H$_5$C$\underline{H}_2$- and C$_2$-$\underline{H}_2$), 7.95 (3H, s; C$_3$-C$\underline{H}_3$) (Found: C, 56.1; H, 4.9; N, 7.4; S, 8.7. C$_{17}$H$_{18}$N$_2$O$_5$S (362.4) requires C, 56.3; H, 5.0; N, 7.7; S, 8.85%).

(ii) With iodobenzene dichloride

A solution of methyl 3-methyl-7β-phenylacetamidoceph-3-em-4-carboxylate (6.93 g., 20 mmole) in water:pyridine (1:4; 100 ml.) was stirred at −10° in the absence of light and treated with a solution of iodobenzene dichloride (11.0 g., 40 mmole) in dry pyridine (25 ml.) dropwise over 10 min. The mixture was stirred for a further 1 hr. at this temperature, then poured into methylene chloride (200 ml.) and washed with 2N-hydrochloric acid (4 × 200 ml.), water (2 × 200 ml.), 3%-aqueous sodium hydrogen carbonate (2 × 200 ml.), and water (2 × 200 ml.). The dried extract was alternately concentrated, then refrigerated, providing three crops of the cephalosporin 1β-oxide (total 2.27 g., 31.3%) identical in all respects to the material described in 1b (i), white feathery needles, m.p. 226°-227°, $\lambda_{max}$ 265.5 nm (ε 8,150); $R_F$ 0.45 [as in 1b (i)]. Concentration of the filtrate afforded a brown tar which, when treated with ether, deposited off-white prisms (1.62 g.), m.p. 174°-175°, $[\alpha]_D − 70°$ (chloroform) TLC (thin-layer chromatography) analysis revealed the presence of two components ($R_F$ 0.45 and 0.24), the least polar of which corresponded in mobility to the known oxide diastereoisomer. The mixture was taken up in methylene chloride - acetone (4:1) (50 ml.) and chromatographed on Kieselgel G (100 g) with the same solvent mixture. 50 ml. Fractions were collected, evaporated, examined by TLC and combined accordingly. Fractions 8-11 (137 mg.) crystallised from ether to provide a further small quantity of the known oxide diastereoisomer (118 mg.), m.p. 222°-223°, $\lambda_{max}$ 266 nm (ε 8,500). Fractions 13-31 (832 mg.) gave, upon treatment with ether, methyl 3-methyl-7β-phenylacetamidoceph-3-em-4-carboxylate, 1α-oxide (727 mg., 10%), m.p. 184°-185°. Recrystallization from acetone-light petroleum afforded white prisms, m.p. 186°-187°, $[\alpha]_D − 159°$, $\lambda_{max}$ 265 nm (ε 5,150), $\nu_{max}$ (CHBr$_3$) 3440 (NH), 1788 (azetidin-2-one), 1728 (CO$_2$CH$_3$), 1682 and 1515 (CONH), and 1050 cm.$^{-1}$ (S→O); τ 2.75 (5H, s; C$_6$$\underline{H}_5$), 4.42 (1H, dd, J 5 and 8 Hz; C$_7$-$\underline{H}$), 5.28 (1H, d, J 5 Hz; C$_6$-$\underline{H}$), 5.87 and 6.40 (2H, AB-q, J 17 Hz; C$_2$-$\underline{H}_2$) 6.25 (3H, s; CO$_2$C$\underline{H}_3$), 6.45 (2H, s; C$_6$H$_5$C$\underline{H}_2$) and 7.92 (3H, s; C$_3$-C$\underline{H}_3$) (Found: C, 56.1; H, 4.9; N, 7.6; S, 8.7. $C_{17}H_{18}N_2O_5S$ (362.4) requires C, 56.3; H, 5.0; N, 7.7; S, 8.85%).

Preparation A2

2,2,2-Trichloroethyl 3-Methyl-7β-phenylacetamido-ceph-3-em-4-carboxylate, 1β-Oxide

(i) With peracetic acid

A solution of 2,2,2-trichloroethyl 3-methyl-7β-phenylacetamidoceph-3-em-4-carboxylate (8.36 g., 18 mmole) in methylene chloride (100 ml.) was cooled to 5° and stirred whilst a solution of peracetic acid (10% w/v; 20 ml., 26 mmole) was added. The mixture was then stirred at room temperature for 10 minutes. Hydrogen peroxide (29% w/v; 4 ml., 3.6 mmole) was added and stirring was continued for a further 30 minutes. The solution was washed successively with water (2 × 50 ml.), sodium bicarbonate solution (2 × 50 ml; 3%), and water, then dried and evaporated to leave a gel. Crystallisation of the gel from methanol afforded the title compound (2.8 g., 32%) as white crystals, m.p. 199°–199.5°, $[\alpha]_D$ + 97° ($CHCl_3$), $\lambda_{max.}$ 269 nm ($E_{1cm}^{1\%}$ 165). A second crop of the title compound (0.82 g., 9.5%), m.p. 195°–197°, $[\alpha]_D$ + 105° ($CHCl_3$), $\lambda_{max.}$ 269 nm ($E_{1cm}^{1\%}$ 161), was obtained by stirring the mother liquors overnight at room temperature. The filtrate from the second crop was evaporated and the residue was chromatographed on silica gel (0.05 - 0.2 mm; 150 g.), with methylene chloride - acetone mixtures as eluent. Gradient elution gave impure starting material (0.56g, 7%), m.p. 147° - 157°, $[\alpha]_D$ + 67.5° ($CHCl_3$), $\lambda_{max.}$ 260 nm ($E_{1cm}^{1\%}$ 124), followed by the title compound (2.29 g., 27.5%), m.p. 190° - 198°, $[\alpha]_D$ + 105.5° ($CHCl_3$), $\lambda_{max.}$ 269 nm ($E_{1cm}^{1\%}$ 159), part of which was crystallised from methanol to give white needles, m.p. 200.5° - 202° (dec.), $[\alpha]_D$ + 108° ($CHCl_3$), $\lambda_{max.}$ 269 nm ($\epsilon$ 7,450), $\nu_{max.}$ ($CHBr_3$) 1800 (azetidin-2-one), 1740 ($CO_2R$), 1680 and 1510 (CONH), and 1043 cm.$^{-1}$(S→O) (Found: C, 45.3; H, 3.5; Cl, 22.0; N, 5.6; S, 6.5. $C_{18}H_{17}Cl_3N_2O_5S$ (479.8) requires C, 45.1; H, 3.6; Cl, 22.2; N, 5.8; S, 6.7%). Further elution gave the 1α-oxide (0.21 g., 2.5%), m.p. 168°–178°, $[\alpha]_D$ − 199° ($CHCl_3$), $\lambda_{max.}$ 269 nm ($E_{1cm}^{1\%}$ 94), which was crystallised from acetone to give white needles, m.p. 181°–189° (dec.), $[\alpha]_D$ −237° ($CHCl_3$), $\lambda_{max.}$ 269 nm ($\epsilon$ 4,850), $\nu_{max.}$ ($CHBr_3$) 1780 (azetidin-2-one), 1725 ($CO_2R$), 1670 and 1510 (CONH) and 1040 cm.$^{-1}$(S→O) (Found: C, 45.2; H, 3.6; Cl, 21.9; N, 5.6; S, 6.6%).

(ii) With m-chloroperbenzoic acid

A solution of 2,2,2-trichloroethyl 3-methyl-7β-phenylacetamidoceph-3-em-4-carboxylate (18.56 g., 40 mmole) in methylene chloride (200 ml.) was stirred at 0°–10°, and a solution of m-chloroperbenzoic acid (8.91 g., 85% pure; 44 mmole) in methylene chloride (150 ml.) was added over a period of five minutes. Stirring was continued a further 15 minutes and the reaction solution then washed with sodium bicarbonate solution (3%, 4 × 100 ml.). The bicarbonate extracts were combined and extracted with methylene chloride (100 ml.). The combined organic solutions were dried and evaporated to a white solid, purification of which was achieved by column chromatography on silica gel (0.05–0.2 mm., 500 g.) with methylene chloride - acetone mixtures as eluent. The appropriate fractions were combined to give the 1β-oxide (16.32 g., 85%) as a white solid, m.p. 193°–200° $[\alpha]_D$ + 104° ($CHCl_3$), $\lambda_{max.}$ 269 nm. ($E_{1cm}^{1\%}$ 154).

Preparation A3

2,2,2-Trichloroethyl 7β-Formamido-3-methylceph-3-em-4-carboxylate, 1β-Oxide

(a) 2,2,2-Trichloroethyl 7β-Formamido-3-methylceph-3-em-4-carboxylate

Acetic anhydride (8 ml) was added to a solution of 2,2,2-trichloroethyl 7β-amino-3-methylceph-3-em-4-carboxylate (6.91 g, 20 mmole) in 98–100% formic acid (40 ml.), and the orange solution was allowed to stand at room temperature for 35 minutes and then successively evaporated at 30°/15 mm and 30°/1 mm. The orange residue was dissolved in ether (200 ml) and the solution was washed successively with 2N-hydrochloric acid, water and 5% aqueous sodium hydrogen carbonate solution (50 ml of each) and water (100 ml), dried and evaporated to give the title ester as a pale yellow foam (6.50 g, 87%), $[\alpha]_D$ + 96° ($CHCl_3$), $\lambda_{max.}$ 262–263 nm ($E_{1cm}^{1\%}$ 152), $\nu_{max.}$ ($CHBr_3$) 3400 (NH), 1786 (azetidin-2-one), 1740 ($CO_2R$), and 1700 and 1510 cm$^{-1}$(CONH), $\tau$ ($CDCl_3$) 1.74 (CHO), 7.79 ($C_3$–$CH_3$) (Found: Cl, 27.5, 27.2; S, 8.2. $C_{11}H_{11}Cl_3N_2O_4S$ (373.7) requires Cl, 28.5; S, 8.6%).

(b) 2,2,2-Trichloroethyl 7β-Formamido-3-methylceph-3-em-4-carboxylate, 1β-Oxide (i) A suspension of 2,2,2-trichloroethyl 7β-amino-3-methylceph-3-em-4-carboxylate, hydrogen p-toluenesulphonate (155.5 g; 0.3 mmole) in ethyl acetate (600 ml.) and water (600 ml.) was stirred with sodium carbonate (36.0g.) for 1½ hr. The layers were then separated and the aqueous layer extracted with ethyl acetate 230 ml.). The combined organic layers were washed with water (600 ml.), dried and evaporated to give a brown oil which was dissolved in ethyl formate (500 ml.). This solution was heated under reflux for 1hr., then evaporated in vacuo. The brown oil was redissolved in ethyl acetate (600 ml) and washed successively with 2N-hydrochloric acid (600 ml), water (600 ml), 3%-sodium bicarbonate solution (600 ml), water (600 ml), dried and evaporated in vacuo to give a pale yellow foam (112.3g.). This foam was dissolved in methylene chloride (1 liter), cooled in ice and stirred whilst peracetic acid (0.285 mole; 0.95 eq) was added over 35 minutes, then stirred a further 30 minutes at room temperature during which time some crystallisation of the product occurred. Methylene chloride (1 liter) was added and the solution washed successively with water (800 ml) and 3%-sodium bicarbonate solution (1 × 1,500 ml, 1 × 800 ml), then dried and concentrated in vacuo to a volume of ca. 400 ml. Methanol (450 ml) was added and the solution cooled slowly to 0° with stirring. The fine off-white solid was collected and combined with two further crops of material obtained by concentration of the mother liquors. The combined solids were washed with ether-methanol (19:1, 750 ml) and dried at 40° in vacuo to provide the title compound (91.2g; 78%). m.p. 168°–171° (dec), $[\alpha]_D$ + 105° $\lambda_{max.}$ 269.5 nm ($E_{1cm}^{1\%}$ 174). A small sample of this was recrystallised from ethanol to provide an analytical sample as a hemi-ethanol solvate, m.p. 176°–181° (dec), $[\alpha]_D$ + 107° $\lambda_{max.}$ 269 nm ($\epsilon$ 7,740), $\nu_{max.}$ ($CHBr_3$) 3610 (ethanol), 3440 (NH), 1800 (azetidin-2-one), 1741

($CO_2R$), 1698 and 1509 (CONH), and 1041 cm$^{-1}$(S→0), $\tau$(CDCl$_3$) 1.74 (1H, s; C$\underline{H}$O), 2.90 (1H, d, J 10 Hz, N$\underline{H}$), 3.82 (1H,dd, J 10 and 4 Hz; C$_7$-$\underline{H}$), 4.99 and 5.16 (2H, AB-q, J 11 Hz; CO$_2$C$\underline{H}_2$CCl$_3$), 5.40 (1H, d, J 4 Hz; C$_6$-$\underline{H}$), 6.28 and 6.69 (2H, AB-q, $\underline{J}$ 18 Hz; C$_2$-$\underline{H}_2$), 7.74 (3$\underline{H}$,s; C$_3$-C$\underline{H}_3$). Typical signals at $\tau$ 6.34 and 8.76 showed the presence of half a mole of ethanol (Found: C, 35.0; H, 3.4; Cl, 25.5; N, 6.7; S, 7.7 C$_{11}$H$_{11}$Cl$_3$N$_2$O$_5$S 0.5 C$_2$H$_5$OH (412.7) requires: C, 34.9; H, 3.4; Cl, 25.8; N, 6.8; S, 7.8%).

(ii) A solution of 2,2,2-trichloroethyl 7$\beta$-formamido-3-methylceph-3-em-4-carboxylate (6.43 g, 17.2 mmole) in methylene chloride (50 ml) was cooled to 0° and peracetic acid (46.2% w/v/; 2.98 ml, 1.05 equiv.) was added dropwise with stirring over 10 minutes. The pale yellow solution was stirred at 0° for 30 minutes, allowed to warm to room temperature and then washed successively with water, 3% aqueous sodium hydrogen carbonate solution and water (50 ml of each), dried and evaporated to give a yellow solid (5.79 g). This solid crystallised by triturating with warm ethanol (50 ml.) to give the title compound as an ethanol solvate (4.67 g, 66%), m.p. 178°-183° (dec), $[\alpha]_D$ + 110°, $\lambda_{max}$ 269 nm ($\epsilon$ 7450) similar in its spectra to those of the compound described in (i) above.

Preparation A4 t-Butyl
7$\beta$-Formamido-3-methylceph-3-em-4-carboxylate, 1$\beta$-Oxide (a) t-Butyl
7$\beta$-Amino-3-methylceph-3-em-4-carboxylate A mixture of 7$\beta$-amino-3-methylceph-3-em-4-carboxylic acid (16.09 g., 75.2 m.moles), dioxan (100 ml.), sulphuric acid (10 ml.) and isobutylene (90 ml.) was shaken in a pressure bottle until a clear solution resulted (2½ hours). The solution was cooled and poured into a mixture of aqueous sodium bicarbonate (600 ml.), ice (100 g.), and ethyl acetate (150 ml.). The aqueous layer was twice more extracted with ethyl acetate and the extracts were washed with brine and dried. Evaporation left a gum which was triturated with petrol (b.p. 40° – 60°) to give off-white crystals (11.17 g., 55%). A sample was recrystallised from ether to give the pure ester, m.p. 126°, $[\alpha]_D$ + 107° (EtOH), $\lambda_{max}$ 271 nm. (E$_{1cm}$$^{1\%}$ 239) (Found: C, 53.1; H, 6.5; N, 10.1; S, 11.5 C$_{12}$H$_{18}$N$_2$O$_3$S requires: C, 53.3; H, 6.7; N, 10.35; S, 11.85%).

(b) t-Butyl
7$\beta$-formamido-3-methylceph-3-em-4-carboxylate (i) A solution of t-butyl 7$\beta$-amino-3-methylceph-3-em-4-carboxylate (2 g.) in formic acid (20 ml.) and acetic anhydride (3 ml.) was stored at room temperature for 5 minutes. The solvents were removed in vacuo and the residue dissolved in ether. The solution was washed with 2 N-hydrochloric acid and water, and dried. Evaporation of the ether gave the amide (1.74 g.) as a white froth, $[\alpha]_D$ + 127° (CHCl$_3$), $\lambda_{max}$ 266 nm. ($\epsilon$ 6,650), $\nu_{max}$ (CHBr$_3$) 3430 (NH) 1775 ($\beta$-lactam), 1720 (CO$_2$R) and 1690 and 1508 cm$^{-1}$ (CONH), $\tau$ (CDCl$_3$) 1.80 (HCO), 3.03 (NH, d, J 9 Hz), 4.23 (C$_7$- $\underline{H}$, 1H,dd,J 4.5 and 9 Hz), 5.9 (C$_6$- $\underline{H}$, 1H,d, J 4.5 Hz), 6.49 and 6.88 (C$_2$-CH$_2$, 2H, AB-q, J 18 Hz), 7.91 (C$_3$-CH$_3$), 8.48 (t-butyl). (Found: C, 51.0; H, 5.9; N, 9.1; S, 10.6 C$_{13}$H$_{18}$N$_2$O$_4$S requires C, 52.3; H, 6.0; N, 9.3; S, 10.7%).

(ii) A solution of t-butyl 7$\beta$-amino-3-methylceph-3-em-4-carboxylate (0.100 g., 0.3 mmole) in ethyl formate (5 ml., 73 mmole) was heated under reflux for 45 minutes. The solvent was evaporated off in vacuo and the residue was dissolved in ether. Removal of the ether in vacuo afforded the formamido-derivative as a foam, $[\alpha]_D$ + 127° (CHCl$_3$) $\lambda_{max}$ 266 nm. ($\epsilon$ 6,600), R$_f$ 0.4 (benzene:ethyl acetate 2:1 Merck silica), and p.m.r. and i.r. spectra similar to those of a sample prepared by the method described in Preparation A4 (b) (i).

(c) t-Butyl
7$\beta$-Formamido-3-methylceph-3-em-4-carboxylate, 1$\beta$-Oxide

A solution of t-butyl 7$\beta$-formamido-3-methylceph-3-em-4-carboxylate (2.38 g. 8 mmole) in methylene chloride (20 ml.) was cooled in an ice-water bath and stirred while peracetic acid (40% w/v; 1.60 ml, 1.05 equiv.) was added dropwise over 2 minutes. The mixture was stirred at 0°–5° for 30 minutes and then at room temperature for 30 minutes, washed with water, aqueous bicarbonate solution and water, dried (Na$_2$SO$_4$), and evaporated to give a pale yellow gel, which was triturated with acetone-ether to give the 1$\beta$-oxide ester as a cream solid (1.86 g, 74%), m.p. 163°-5° (dec), $[\alpha]_D$ + 182° (CHCl$_3$), $\lambda_{max}$ 264 nm ($\epsilon$ 7,850), $\nu_{max}$(CHBr$_3$) 3390 (NH), 1796 (azetidin-2-one), 1720 (CO$_2$R), 1695 and 1508 (CONH), and 1040 cm$^{-1}$(S→O) $\tau$ (CDCl$_3$, with 2 drops Me$_2$SO-d$_6$) 1.68 (1H,s; NHC$\underline{H}$O), 7.83 (3H,s; C$_3$-C$\underline{H}_3$), 8.42 (9H,s CO$_2$C(C$\underline{H}_3$)$_3$), 8.78 (0.125 mole diethyl ether). The material was used without further purification for subsequent experiments.

Preparation A5

2,2,2-Trichloroethyl
3-Methyl-7$\beta$-phenoxyacetamidoceph-3-em-4-carboxylate, 1$\beta$-Oxide A solution of 2,2,2-trichloroethyl 3-methyl-7$\beta$-phenoxyacetamidoceph-3-em-4-carboxylate (4.80 g.; 10 mmole) in methylene chloride (50 ml) was treated with peracetic acid (1.9 ml., containing 5.26 mmole oxidant per ml.; 10 mmole) at 20° to 30° with stirring for 3 minutes. The solution was washed with water (2 × 20 ml) and dilute sodium bicarbonate solution (20 ml), dried, and evaporated to a white solid (5.075 g). This solid may be used without further purification in subsequent reactions. Recrystallisation of this solid from a mixture of methanol (50 ml) and acetone (15 ml) gave the title compound as white needles (3.10 g; 62.6%), m.p. 172° to 177°, $[\alpha]_D$ + 65° (CHCl$_3$), $\lambda_{max}$ 269 nm (E$_{1cm}$$^{1\%}$ 180) and 275 nm (E$_{1cm}$$^{1\%}$ 163); inflexion at 264 nm (E$_{1cm}$$^{1\%}$ 165).

A small portion of this compound was recrystallised from methanol-acetone to provide an analytical sample, m.p. 173° to 178°, $[\alpha]_D$ + 66.7° (CHCl$_3$), $\lambda_{max}$ 269 nm ($\epsilon$ 9,075) and 275 nm ($\epsilon$ 8,250), inflexion at 265 nm ($\epsilon$ 8,675), $\nu_{max}$ 3450 (NH), 1780 (azetidin-2-one), 1745 (CO$_2$R), 1700 (CONH), 1030 cm.$^{-1}$ (S→O), $\tau$ (CDCl$_3$) 2.15 (1H,d, J 10 Hz; N$\underline{H}$), 2.5 to 3.2 (5H,m; C$_6\underline{H}_5$), 3.88 (1H,dd, J 10 and 4.5 Hz; C$_7$-$\underline{H}$), 4.93 and 5.18 (2H, AB-q, J 12 Hz; C$\underline{H}_2$CCl$_3$), 5.38 (3H, broadened s; C$_6$H$_5$OCH$_2$ and C$_6$-$\underline{H}$), 6.29 and 6.79 (2H, AB-q,J 19 Hz; C$_2$-$\underline{H}_2$), 7.78 (3H,s; C$_3$-C$\underline{H}_3$) (Found: C, 43.7; H, 3.6; Cl, 21.4; N, 5.2; S, 6.6. C$_{18}$H$_{17}$Cl$_3$N$_2$O$_6$S (495.8) requires C, 43.6; H, 3.5; Cl, 21.5; N, 5.7; S, 6.5%).

Preparation A6

2,2,2-Trichloroethyl 3-Methyl-7β-[D-2-(2,2,2-trichloroethoxycarbonylamino)-2-phenylacetamido]-ceph-3-em-4-carboxylate, 1β-Oxide Peracetic acid (46.2% w/v; 1.73 ml, 1.05 equiv.) was added dropwise over 5 minutes to a stirred solution of 2,2,2-trichloroethyl 3-methyl-7β-(D-2-phenyl-2-(2,2,2-trichloroethoxycarbonylamino)acetamido]ceph-3-em-4-carboxylate (6.54 g, 10 mmole) in methylene chloride (50 ml) cooled to 0°. The reaction mixture was stirred at 0° for 30 minutes, washed with water, 3% aqueous sodium hydrogen carbonate solution and water (50 ml of each), dried and evaporated to a yellow solid (6.58 g,), which was triturated with warm ethanol (50 ml) to give the title ester 1β-oxide (5.78 g, 86%), m.p. 216.5° to 217.5° (dec), $[\alpha]_D + 42°$, $\lambda_{max.}$ 269 nm ($\epsilon$ 7,400), $\nu_{max.}$ (CHBr$_3$) 3360 (NH), 1798 (azetidin-2-one), 1734 (CO$_2$R), 1690 and 1500 (CONH), and 1048 cm,$^{-1}$ (S→O), $\tau$ 1.52, 1.63 (two 1H,d, J~8 Hz, NH), 2.6 (5H,m; C$_6$H$_5$). 4.19 (1H,dd, J 9 and 5 Hz; C$_7$-H), 4.43 (1H,d, J 8 Hz; CHNH), 4.82 5.01 (2H, AB-q,J 12 Hz; CH$_2$CCl$_3$), 5.12 (1H,d, J 5 Hz; C$_6$-H), 5.19 (2H,s, NHCO$_2$CH$_2$CCl$_3$), 6.12, 6.42 (2H, AB-q,J 19 Hz; C$_2$-H$_2$) and 7.90 (3H,s; C$_3$-CH$_3$) (Found: C, 37.9; H, 2.8; Cl, 31.8; N, 6.0; S, 4.9. C$_{21}$H$_{19}$Cl$_6$N$_3$O$_7$S (670.2) requires C, 37.6; H, 2.9; Cl, 31.7; N, 6.3; S, 4.8%).

Preparation A7 p-Methoxybenzyl 3-Methyl-7β-phenylacetamidoceph-3-em-4-carboxylate, 1β-Oxide A solution of p-methoxybenzyl 3-methyl-7β-phenylacetamidoceph-3-em-4-carboxylate (9.04 g, 20 mmole) and peracetic acid (50% w/v; 4.6 ml, 1.5 equiv) in methylene chloride (200 ml) was stirred for 30 minutes when saturated sodium hydrogen carbonate solution (150 ml) was added and the stirring continued for a further 15 minutes. The organic phase was washed with 3% sodium hydrogen carbonate solution and saturated brine (200 ml of each), dried and evaporated to ca. 75 ml to give the title ester 1β-oxide (7.19 g, 77%), m.p. 194 to 194.5°, $\lambda_{max.}$ 226.5 nm (E$_{1cm}^{1\%}$ 372) and 266 nm (E$_{1cm}^{1\%}$ 212), inflexion at 279 nm (E$_{1cm}^{1\%}$ 140). Evaporation of the filtrate gave a second crop (1.30 g, 14%), m.p. 188 to 189°, $\nu_{max.}$ 227 nm (E$_{1cm}^{1\%}$ 355) and 266 nm (E$_{1cm}^{1\%}$ 193), inflexion at 279 nm (E$_{1cm}^{1\%}$ 133). Part (1.5 g) of the first crop was crystallised from methylene chloride to give white crystals (0.90 g), m.p. 194° to 195°, $[\alpha]_D + 129°$, $\nu_{max.}$ 227 nm ($\epsilon$ 17,350) and 266 nm ($\epsilon$ 10,000), inflexion at 279 nm ($\epsilon$ 6,700), $\nu_{max.}$ 1775 (azetidin-2-one), 1728 and 1716 (CO$_2$R), 1652 and 1540 (CONH), 1236 (OMe) and 1032 cm$^{-1}$(S→O), $\tau$ 1.72 (1H,d, J 8 Hz; NH), 2.63, 3.07 (4H,2d J 9 Hz; CH$_2$C$_6$H$_4$OCH$_3$), 2.69 (5H,s; C$_6$H$_5$), 4.25 (1H,dd J 8,5 Hz; C$_7$-H), 4.80 (2H,s; CH$_2$C$_6$H$_4$), 5.16 (1H,d, J 5 Hz; C$_6$-H), 6.21, 6.44 (2H, AB-q, J 18 Hz; C$_2$-H$_2$), 6.24 (3H,s; OCH$_3$) 6.30, 6.48 (2H, AB-q, J 14 Hz; C$_6$H$_5$CH$_2$), 7.98 (3H,s; C$_3$-CH$_3$) (Found: C, 61.5; H, 5.1; N, 5.7; S, 6.8. C$_{24}$H$_{24}$N$_2$O$_6$S (468.5) requires C, 61.5; H, 5.2, N, 6.0; S, 6.8%).

Preparation A8 t-Butyl 3-Methyl-7β-phenylacetamidoceph-3-em-4-carboxylate, 1β-Oxide

Phenylacetyl chloride (0.58 ml, 1.1 equiv.) was added to a stirred solution of t-butyl 7β-amino-3-methylceph-3-em-4-carboxylate (1.08 g, 4 mmole) in dimethylacetamide (2.5 ml) and acetonitrile (10 ml.) The mixture was stirred at ca. 25° for 45 minutes and the acetonitrile was removed in vacuo. Water (50 ml) and ethyl acetate (150 ml) were added and the organic phase was washed with water, 3% sodium hydrogen carbonate solution and water (50 ml of each), dried and evaporated. The residual colourless oil was dissolved in methylene chloride (10 ml) and cooled in an ice-bath while peracetic acid (40% w/v; 1.16 ml, 1.1 equiv.) was added dropwise. The solution was stirred at ca. 20° for 30 minutes and saturated sodium hydrogen carbonate solution (20 ml) was added. The organic phase was washed with water (50 ml), dried and evaporated to a white gelatinous solid, t.l.c. (acetone-methylene chloride; 1:4) R$_f$ 0.49, 0.80, which was purified by chromatography on Kieselgel G (50g). Elution with acetonemethylene chloride (1:9) gave a pale yellow solid which was crystallised from acetone-light petroleum, b.p. 40°-60° (1:1; 10 ml) to give t-butyl 3-methyl-7β-phenylacetamidoceph-3-em-4-carboxylate, 1,1-dioxide (0.17 g, 11 %), m.p. 87 to 88°, $[\alpha]_D + 36.5°$, $\lambda_{max.}$ 259 nm ($\epsilon$ 8,150), $\nu_{max.}$ (CHBr$_3$) 3410 (NH), 1798 (acetidin-2-one), 1714 (CO$_2$R) and 1680 and 1510 cm$^{-1}$ (CONH), $\tau$ (CDCl$_3$) 2.66 (5H,s; C$_6$H$_5$), 3.06 (1H,d, J 10.5 Hz; NH), 3.90 (1H,dd, J 10.5, 5Hz; C$_7$-H), 5.19 (1H,d, J 5 Hz; C$_6$-H), 6.09, 6.55 (2H, AB-q, J 18 Hz; C$_2$-H$_2$), 6.34 (2H,s; C$_6$H$_5$CH$_2$), 7.94 (3H,s; C$_3$-CH$_3$), 8.49 (9H,s; CO$_2$C(CH$_3$)$_3$). (Found: C, 56.9; 56.6; H, 5.8; 5.7; N, 6.3, 6.3; S, 7.4 C$_{20}$H$_{24}$N$_2$O$_6$S (420.5) requires C, 57.1; H, 5.75; N, 6.7; S, 7.6%). Further elution with acetone-methylene chloride (1:9) gave a white gelatinous solid which dissolved in acetone (10 ml) and reprecipitated by addition of light petroleum (b.p. 40°-60°; 10 ml) to give the title ester 1β-oxide (1.04 g, 67%), m.p. 181° to 182° (dec), $[\alpha]_D + 164°$, $\lambda_{max.}$ 265 nm ($\epsilon$ 7,900), $\nu_{max.}$ (CHBr$_3$) 3390 (NH), 1790 (azetidin-2-one), 1716 (CO$_2$R), 1678 and 1510 (CONH) and 1050 cm$^{-1}$ (S→O), $\tau$ (CDCl$_3$ + 3 drops Me$_2$SO-d$_6$) 2.68 (5H,s; C$_6$H$_5$), 4.12 (1H,dd, J 9.5,4.5 Hz; C$_7$-H), 5.34 (1H,d, J 4.5 Hz; C$_6$-H), 6.37 (2H,s; C$_6$H$_5$CH$_2$), 6.56 (2H,s; C$_2$-H$_2$), 7.91 (3H,s; C$_3$-CH$_3$), 8.47 (9H,s; CO$_2$C(CH$_3$)$_3$) (Found: C, 60.0, 59.6; H, 6.1, 5.9; N, 6.7, 6.7; S, 7.8 C$_{20}$H$_{24}$N$_2$O$_5$S (404.5) requires C, 59.4; H, 6.0; N, 6.9; S, 7.9%).

PREPARATION A9

2,2,2-Trichloroethyl 3-Methyl-7β-(2,2,2-trichloroethoxy carbonylamino)ceph-3-em-4-carboxylate, 1β-Oxide (a) 2,2,2-Trichloroethyl 3-Methyl-7β-(2,2,2-trichloroethoxy carbonylamino)ceph-3-em-4-carboxylate 2,2,2-Trichloroethyl chloroformate (3.15 ml, 22 mmole) was added to a suspension of 2,2,2-trichloroethyl 7β-amino-3-methylceph-3-em-4-carboxylate hydrogen p-toluenesulphonate (10.36 g, 20 mmole) in a mixture of dimethylacetamide (25 ml) and acetonitrile (100 ml.) The mixture was stirred at ca. 25° for 30 minutes, the acetonitrile was evaporated and ethyl acetate (80 ml) was added. The solution was washed with saturated sodium hydrogen carbonate solution (80 ml), dried and evaporated to an oil which could not be crystallised. The oil was taken up in chloroform (50 ml), washed with water (3 × 50 ml) and re-evaporated to an orange from which on trituration with methanol (20 ml) gave the title ester as an off-white solid, $\lambda_{max.}$ 262 nm ($E_{1cm}^{1\%}$ 113.5). Crystallisation from ethanol gave an analytical sample, m.p. 179° to 181.5°, $[\alpha]_D + 70°$, $\lambda_{max.}$ 262 nm ($\epsilon$ 6,000), $\nu_{max}$ (CHBr$_3$) 3410 (NH), 1780 (azetidin-2-one), 1740 and 1520 (NHCO$_2$R) and 1740 cm$^{-1}$ (CO$_2$R), $\tau$(CDCl$_3$) 3.98 (1H,d,J 9.5 Hz; N$\underline{H}$), 4.34 (1H,dd,J 9.5 Hz; C$_7$-$\underline{H}$) 4.91 (1H,d J 5 Hz; C$_6$-$\underline{H}$), 4.91, 5.08 (2H, AB-q, J 12 Hz; CO$_2$C$\underline{H}_2$CCl$_3$), 5.17 (2H,s; NHCO$_2$C$\underline{H}_2$CCl$_3$), 6.34, 6.73 (2H, AB-q, J 18 Hz; C$_2$-$\underline{H}_2$), 7.74 (3H,s; C$_3$-C$\underline{H}_3$) (Found: C, 30.3; H, 2.4; Cl, 40.2; N, 5.3; S, 6.5. C$_{13}$H$_{12}$Cl$_6$N$_2$O$_5$S (521.1) requires C, 30.0; H, 2.3; Cl, 40.8; N, 5.3; S, 6.2%

(b) 2,2,2-Trichloroethyl 3-Methyl-7β-(2,2,2-trichloroethoxycarbonylamino)-ceph-3-em-4-carboxylate, 1β-Oxide Peracetic acid (40% w/v; 2.0 ml, 1.05 equiv.) was added over 15 minutes to a stirred solution of 2,2,2-trichloroethyl 3-methyl-7β-(2,2,2-trichloroethoxycarbonylamino)ceph-3-em-4-carboxylate (5.24 g, 10.07 mmole) in methylene chloride (50 ml) cooled in an ice-bath. A white solid separated from the solution. The cooled mixture was stirred for 30 minutes, and the solid was filtered off, washed with water and dried to give the title ester 1β-oxide (3.285g. 61%), $[\alpha]_D + 66°$, $\lambda_{max.}$ 269 nm ($E_{1cm}^{1\%}$ 135). The filtrate and washings were combined and the organic phase was washed with water (2 × 25 ml), 4% sodium hydrogen carbonate solution (20 ml), and water (15 ml), dried and evaporated. The residual solid was triturated with methanol to give a less pure second crop of ester 1β-oxide (1.60 g, 30%), m.p. 205° to 207.5°, $[\alpha]_D + 57°$, $\lambda_{max}$ 269 nm ($E_{1cm}^{1\%}$ 135). Part of the first crop was crystallised from boiling methanol to give an analytical sample, m.p. 201° to 202° (dec), $[\alpha]_D + 71°$, $\lambda_{max}$ 269 nm ($\epsilon$ 7,500), $\nu_{max}$ 3396 (NH), 1772 and 1764 (azetidin-2-one), 1750 (CO$_2$R), 1730 and 1516 (NHCO$_2$R) and 1050 cm$^{-1}$ (S→O), $\tau$ 2.50 (1H,d, J 9 Hz; N$\underline{H}$), 4.26 (1H,dd, J 9,5 Hz; C$_7$-$\underline{H}$), 4.75, 4.87 (2H, AB-q, J 12 Hz; CO$_2$C$\underline{H}_2$CCl$_3$ 4.96 (1H,d, J 5 Hz; C$_6$-$\underline{H}$), 5.05 (2H,s; NHCO$_2$C$\underline{H}_2$CCl$_3$), 6.12 (2H,s; C$_2$-$\underline{H}$), 7.84 (3H,s; C$_3$-C$\underline{H}_3$) (Found: C, 29.3; H, 2.3; Cl, 39.0; N, 5.1; S. 5.9. C$_{13}$H$_{12}$Cl$_6$N$_2$O$_6$S (537.1) requires C, 29.1; H, 2.3; Cl, 39.6; N, 5.2; S, 6.0%).

Preparation A10 t-Butyl 3-Methyl-7α-phenoxyacetamidoceph-3-em-4-carboxylate, 1β-Oxide (a) t-Butyl 3-Methyl-7β-phenoxyacetamidoceph-3-em-4-carboxylate A solution of ethylene oxide (12 ml) in dry methylene chloride (30 ml) was added to a solution of t-butyl 7β-amino-3-methylceph-3-em-4-carboxylate (52 g, 0.193 mole) in dry methylene chloride (200 ml) cooled in an ice-water bath. A solution of redistilled phenoxyacetyl chloride (33.2 g, 0.194 mole) in dry methylene chloride (25 ml) was added over 2 minutes with stirring. The mixture was stirred for 2 hours, washed with 3% sodium hydrogen carbonate solution (2 × 70 ml), and water, N-hydrochloric acid and brine (70 ml of each), dried and evaporated to a foam. This foam was redissolved in methylene chloride (200 ml) and part (3 ml) of the solution was reevaporated to a white foam (1.13 g), $[\alpha]_D + 107°$, $\lambda_{max}$ 268.5 nm ($\epsilon$ 7,850) 274.5 nm ($\epsilon$ 7,000), inflexion at 264 nm ($\epsilon$ 7,500), $\nu_{max}$ (CHBr$_3$) 3417 (NH), 1786 (azetidin-2-one), 1718 (CO$_2$R) and 1697 and 1530 cm$^{-1}$ (CONH), $\tau$ 0.99 (1H,d, J 8.5 Hz; NH), 2.5 to 3.2 (5H,m; C$_6$H$_5$OCH$_2$), 4.34 (1H,dd, J 8.5, 5 Hz; C$_7$-$\underline{H}$), 4.91 1H,d, J 5 Hz; C$_6$-H), 5.38 (2H,s; C$_6$H$_5$OC$\underline{H}_2$), 6.38, 6.66 (2H, AB-q, J 18 Hz; C$_2$-$\underline{H}_2$), 8.01 (3H,s; C$_3$-C$\underline{H}_3$), 8.52 (9H,s; CO$_2$C(CH$_3$)$_3$) (Found: C, 58.3, 58.4; H, 5.95, 6.0; N, 6.7, 7.0; S, 7.7 C$_{20}$H$_{24}$N$_2$O$_5$S (404.5) requires C, 59.4; H, 6.0; N, 6.9; S, 7.7%).

(b) t-Butyl 3-Methyl-7β-phenoxyacetamidoceph-3-em-4-carboxylate, 1β-Oxide

The remainder of the methylene chloride solution of t-butyl 3-methyl-7β-phenoxyacetamidoceph-3-em-4-carboxylate from (a) was stirred and cooled to −5° and peracetic acid (38.6% w/v; 34.4 ml, 0.190 mole) was added over 30 minutes, keeping the temperature below 5°. T.l.c. (acetone-methylene chloride; 1:4) showed that oxidation was incomplete so portions (5 × 1 ml) of peracetic acid were added and stirring continued until t.l.c. showed that only a trace of unchanged sulphide remained. The reaction mixture was washed with 3% sodium hydrogen carbonate solution (3 × 100 ml) and brine (100 ml), dried and evaporated to a gel. This gel was dissolved in 1,2-dichloroethane (500 ml), and the solution was evaporated to ca. 200 ml and then rediluted to 500 ml with dry 1,2-dichloroethane. Part (62.2 ml) of this solution was used for Example B10 (i) the remainder was evaporated to a gel which was triturated with methanol:light petroleum, (3:2) and chilled. The white crystalline solid was collected and washed with light petroleum to give the title ester 1β-oxide (41.54 g), m.p. 116° to 120° with softening at 99° to 100°, $[\alpha]_D + 55.5°$, $\lambda_{max}$ 262.5 nm ($E_{1cm}^{1\%}$ 204) and 267 nm ($E_{1cm}^{1\%}$ 207), inflexion at 273 nm ($E_{1cm}^{1\%}$ 165), t.l.c. (acetone-methylene chloride; 1.4) R$_f$ 0.44, with faint spots at R$_f$ 0.26, 0.65. Evaporation of the filtrate and retrituration with methanol-light petroleum gave a second crop (7.71 g), m.p. 95° to 96°, $[\alpha]_D + 71°$, $\lambda_{max}$ 263 nm ($E_{1cm}^{1\%}$ 211) and 267 nm ($E_{1cm}^{1\%}$ 212), inflexion at 273 nm ($E_{1cm}^{1\%}$ 169). The mother liquors were chromatographed on Kieselgel G (350 g) with acetone-methylene chloride (1:4) as eluant to give unchanged starting material (3.31 g), title ester 1β-oxide (12.65 g), m.p. 92° to 95°, $[\alpha]_D + 73°$, $\lambda_{max}$ 263 nm ($E_{1cm}^{1\%}$ 202) and 267.5 nm ($E_{1cm}^{1\%}$ 205), inflexion at 273 nm ($E_{1cm}^{1\%}$ 165), and t-butyl 3-methyl-7β-phenoxyacetamidoceph-3-em-4-carboxylate, 1α-oxide as a pale yellow foam which was crystallised from acetone to give a white crystalline solid (1.33 g), m.p. 95° to 110°, $[\alpha]_D - 125°$ $\lambda_{max}$ 263 nm ($\epsilon$ 6,500) and 268 nm ($\epsilon$ 6,700), inflexion at 274.5 nm ($\epsilon$ 5,450), $\nu_{max.}$ 3252 and 3210 (NH), 1760 (azetidin-2-one), 1716 (CO$_2$R), 1700 and 1540 (CONH) and 1024 cm$^{-1}$ (S→O), $\tau$ 0.71 (1H,d, J 9 Hz; NH), 2.5 to 3.1 (5H,m; C$_6$H$_5$OCH$_2$), 4.34 (1H,dd, J 9, 4.5 Hz; C$_7$-$\underline{H}$), 5.22 (1H,d, J 4.5 Hz; C$_6$-$\underline{H}$), 5.38 (2H,s; C$_6$H$_5$OC$\underline{H}_2$), 5.86, 6.42 (2H, AB-q, J 17 Hz; C$_2$-$\underline{H}_2$), 7.98 (3H,s; C$_3$-C$\underline{H}_3$), 8.50 (9H,s; CO$_2$C(CH$_3$)$_3$), 7.90 (ca. 0.3M acetone) (Found: C, 57.2, 56.9; H, 5.9, 6.0; N, 6.2, 6.3; S, 7.2. C$_{20}$H$_{24}$N$_2$O$_6$S (420.5) requires C, 57.1; H, 5.75; N, 6.7; S, 7.6%). A small portion of the chromatographed 1β-oxide was crystallised from methanol-light petroleum giving, m.p. 84° to 91°, $[\alpha]_D +$ 78°, $\lambda_{max}$ 263 nm ($\epsilon$ 9,150) and 267.5 nm ($\epsilon$ 9,250), inflexion at 273 nm ($\epsilon$ 7,350), $\nu_{max}$ 3375 and 3280 (NH), 1765 (azetidin-2-one), 1715 (CO$_2$R), 1660, 1670 and 1520 (CONH), and 1045 cm$^{-1}$ (S→O), $\tau$ 1.88 (1H,d, J 10z; N$\underline{H}$), 2.5 to 3.1 (5H,m; C$_6$$\underline{H}$$_5$OCH$_2$), 4.03 (1H,dd, J 10,5 Hz; C$_7$-$\underline{H}$), 5.06 (1H,d, J 5 Hz; C$_6$-$\underline{H}$), 5.32 (2H,s; C$_6$H$_5$OC$\underline{H}$$_2$), 6.15, 6.39 (2H, AB-q, J 19 Hz; C$_2$-$\underline{H}$$_2$), 7.99 (3H,s; C$_3$-C$\underline{H}$$_3$), 8.49 (9H,s; CO$_2$C(CH$_3$)$_3$) (Found: C, 56.4; H, 5.7; N, 6.6; S, 7.5%).

Preparation A11

7$\beta$-Formamido-3-methylceph-3-em-4-carboxylic acid, 1$\beta$-oxide

7$\beta$-Amino-3-methylceph-3-em-4-carboxylic acid (21.4g, 0.1 mole) was added with stirring to a mixture of formic acid (98–100%;50 ml) and acetic anhydride (13 ml). The black reaction mixture was stirred at 20° for 1 hour and then cooled to ca 5° when peracetic acid (43.7% w/v; 17.4 ml, 0.1 mole) was added over a period of 15 minutes. A light brown solid had precipitated by the end of the addition. The reaction mixture was diluted with water (50 ml) and stirred for a further 10 minutes, and the solid was filtered off, washed with water (30 ml), dried (10.63 g) and crystallised from boiling water (120 ml) to give the title acid (6.18 g, 24%), m.p. 165°–168° resolidifying and then melting at 185°–193°, [$\alpha$]$_D$$^{25}$ + 293° (c 1.13; H$_2$O), [$\alpha$]$_D$$^{25}$ + 211° (c 1.09; Me$_2$SO), $\lambda_{max.}$ (pH 6 phosphate) 255 nm (E$_{1cm}$$^{1\%}$ 329, $\epsilon$ 8,500), $\nu_{max.}$ (Nujol) 3300 (NH), 3620 and ca 2600 (OH, monomeric and dimeric), 1770 (azetidin-2-one), ca 1760 and 1720 (CO$_2$H, monomeric and dimeric), 1660 and 1535 (CONH) and 990 cm$^{-1}$(S→O), $\tau$ (D$_2$O, NaHCO$_3$) 1.80 (1-proton singlet; C$\underline{H}$O), 4.12 (1-proton doublet, J 5 Hz, C$_7$-$\underline{H}$), 5.14 (1-proton doublet, J 5 Hz, C$_6$-$\underline{H}$), 6.36 (2-proton singlet; C$_2$-$\underline{H}$$_2$), 8.04 (3-proton singlet; C$_3$-C$\underline{H}$$_3$) (Found: C, 37.5, 37.85; H, 4.0, 4.0; N, 9.9, 9.6; S, 12.2 C$_9$H$_{10}$N$_2$O$_5$S (258.3) requires C, 41.85; H, 3.9; N, 10.85; S, 12.4%). The compound was probably a hydrate.

Preparation A12

(a) 2,2,2-Trichloroethyl 7$\beta$-(DL-2-Bromophenylacetmido)-3-methylceph-3-em-4-carboxylate 2,2,2-Trichloroethyl 7$\beta$-amino-3-methylceph-3-em-4-carboxylate (3.5 g., 10.1 mmole) and dicyclohexylcarbodiimide (2.5 g., 12.1 mmole) were dissolved in dry methylene chloride (40 ml). A solution of DL-$\alpha$-bromophenylacetic acid (2.6 g., 12.1 mmole) in dry methylene chloride (10 ml) was added slowly. The reaction mixture was stirred for 2 hours at ca 25°, then at 5° overnight, and then filtered and the filtrate evaporated to a brown oil. The oil was dissolved in ethyl acetate (50 ml) and washed with dilute sodium bicarbonate solution (2 × 50 ml) and brine (50 ml) and evaporated to an oil which on dilution with ether (10 ml) and precipitation with light petroleum yielded the title compound as a cream solid (4.80 g., 88.5%); m.p. 98° to 115°; [$\alpha$]$_D$ + 62° (CHCl$_3$); $\nu_{max.}$ 3275(NH), 1766 (azetidin-2-one), 1730 (CO$_2$R), and 1660 and 1535 cm$^{-1}$ (CONH); $\tau$ (CDCl$_3$) 2.3 to 2.8 (5H,M,C$_6$H$_5$), 4.28 and 4.32 (1H,2 superimposed dd,J,4.5 and 9 Hz, C$_7$-$\underline{H}$, diastereomeric pair), 4.55 and 4.56 (1H, 2 s, PhC$\underline{H}$Br, diastereomeric pair), 4.99 (1H,d,J 4.5 Hz,C$_6$-$\underline{H}$), 5.04 and 5.24 (2H,ABq, J 12 Hz, CO$_2$CH$_2$CCl$_3$), 6.48 and 6.77, and 6.48 and 6.80 (2H, 2 superimposed ABq, J 19 Hz, C$_2$-$\underline{H}$$_2$, diastereomeric pairs), 7.80 (3H,s, C$_3$-C$\underline{H}$$_3$). (Found: C,40.8 and 40.7; H, 3.1 and 3.2; N, 5.2 and 5.2; S, 5.8; total halogen content 3.94 equiv./mole. C$_{18}$H$_{16}$BrCl$_3$N$_2$O$_4$S (542.7) requires: C, 39.8; H, 3.0; N, 5.2; S, 5.9%; total halogen content 4 equiv./mole)

(b) 2,2,2-Trichloroethyl 7$\beta$-(DL-2-Bromophenylacetamido)-3-methylceph-3-em-4-carboxylate, 1$\beta$-Oxide A solution of 2,2,2-trichloroethyl 7$\beta$-(DL-2-bromophenylacetamido)-3-methylceph-3-em-4-carboxylate (1.542 g, 2.85 mmole) in methylene chloride (40 ml) was reacted with peracetic acid (ca 40% solution in acetic acid, 0.54 ml) at ca 25° by stirring for several minutes. Sodium bicarbonate (0.5 g.) was added and stirring continued for 5 minutes. The mixture was then filtered and the filtrate evaporated leaving the title compound as a white solid which could be used without further purification in subsequent stages. An analytical specimen was obtained by crystallisation of the crude solid from acetone m.p. 199° to 204°; [$\alpha$]$_D$ + 110°; $\lambda_{max.}$ 267 nm ($\epsilon$ 8,820); $\nu_{max.}$3356 (NH), 1755 (azetidin-2-one), 1725 (CO$_2$R), 1695, 1675 and 1515 (CON$\underline{H}$), 1020 and 1045 (S→O); $\tau$ (CDCl$_3$ + trace Me$_2$SO-D$_6$) 1.42 (1H,d, J 9 Hz, N$\underline{H}$), 2.3 to 2.7 (5H, m, C$_6$$\underline{H}$$_5$), 4.21 (1H,dd, J 4.5 and 9 Hz, C$_7$-$\underline{H}$), 4.24 and 4.26 (1H, 2S, C$_6$H$_5$C$\underline{H}$Br, diastereomeric pair), 4.93 and 5.18 (2H, ABq, J 12.5 Hz, CO$_2$C$\underline{H}$$_2$CCl$_3$), 5.12 (1H,d, J 4.5 Hz, C$_6$-$\underline{H}$) 6.2 and 6.64 (2H, ABq, J 18 Hz, C$_2$-$\underline{H}$$_2$). (Found: C, 39.0; H, 3.0; N, 4.7; S, 5.7; total halogen content 3.94 equiv./mole. C$_{18}$H$_{16}$BrCl$_3$N$_2$O$_5$S (558.7) requires: C, 38.7; H, 2.9; N, 5.0; S, 5.7% total halogen content 4 equiv./mole).

SECTION B

Example B1

Bromination of methyl 3-methyl-7$\beta$-phenylacetamidoceph-3-em-4-carboxylate, 1$\beta$-oxide to give methyl 3-bromomethyl-7$\beta$-phenyl-acetamidoceph-3-em-4-carboxylate, 1$\beta$-oxide (i) Photo-initiated bromination with N-bromosuccinimide in refluxing chloroform A solution of methyl 3-methyl-7$\beta$-phenylacetamidoceph-3-em-4-carboxylate, 1$\beta$-oxide (1.45 g., 4 mmole) and N-bromosuccinimide (1.25 g., 7 mmole) in dry, ethanol-free chloroform (100 ml.) was heated to reflux in an atmosphere of nitrogen and illuminated with tungsten light (1 × 100-watt bulb) for 1 hr. The reaction solution was evaporated to half its volume, then applied to eight preparative thin-layer plates (40 × 20 cm., coated with Kieselgel HF$_{254+366}$, 2mm. thick). The plates were eluted with methylene chloride-acetone (4:1) and the bands having R$_F$ 0.4 were removed, combined, and extracted with methylene chloride - acetone (1:1, 600 ml.). Evaporation of the organic solution so obtained gave the title compound (423 mg., 24%) as a pale cream solid, m.p. 170°–8° (dec.), [$\alpha$]$_D$ +50° $\lambda_{max.}$ 280.5 nm (E$_{1cm}$$^{1\%}$ 209), $\nu_{max.}$ 1772 (azetidin-2-one), 1702 (CO$_2$CH$_3$), 1640 and 1516 (CONH), and 1026 cm.$^{-1}$ (S→O), $\tau$ 5.37 and 5.55 (2H, AB-q, J 5 Hz; C$\underline{H}$$_2$Br). Part of this product was further purified by washing with cold methylene chloride which gave a white solid, m.p. 193°–4° (dec.), [$\alpha$]$_D$ + 60°, $\lambda_{max.}$ 281 nm ($\epsilon$ 9,960) (Found: C, 46.7; H, 3.9; Br, 18.0; N, 5.6; S, 7.4. C$_{17}$H$_{17}$BrN$_2$O$_5$S (441.3) requires: C, 46.3; H, 3.9; Br, 18.1; N, 6.35; S, 7.3%). The product gave a pink-purple colour (after TLC) on spraying with pyridine, warming to 60°–80° for 2–3 minutes, removing the excess of pyridine by evaporation in vacuo, and spraying with potassium iodoplatinate reagent.

(ii) Initiated by azobisisobutyronitrile in refluxing chloroform.

A solution of methyl 3-methyl-7β-phenylacetamidoceph-3-em-4-carboxylate, 1β-oxide (150 mg., 0.43 mmole), N-bromosuccinimide (80 mg., 0.45 mmole, 1.05 eq.) and azobisisobutyronitrile (5 mg., 0.037 mmole) in dry, ethanol-free chloroform (15 ml.) was heated to reflux in an atmosphere of nitrogen for 9.5 hours, and then evaporated. The residual orange oil was dissolved in methylene chloride - acetone (minimum volume, 4:1) and chromatographed on a column of Kieselgel G (10 g.) with methylene chloride - acetone (4:1) as eluent and fractions of 10 ml. Fractions 10 and 11 were combined and evaporated to give the title compound (65 mg., 35%) as an off-white crystalline solid, m.p. 125°–160° (dec.), $\lambda_{max.}$ 280 nm ($E_{1cm}^{1\%}$ 154), similar by infrared and p.m.r. spectroscopy and by TLC with the product from Example B1 (i).

Example B2

Bromination of 2,2,2-trichloroethyl 3-methyl-7β-phenylacetamidoceph-3-em-4-carboxylate, 1β-oxide to give 2,2,2-trichloroethyl 3-bromomethyl-7β-phenylacetamidoceph-3-em-4-carboxylate, 1β-oxide (i) Photo-initiated bromination with N-bromosuccinimide in refluxing chloroform A solution of 2,2,2-trichloroethyl 3-methyl-7β-phenylacetamidoceph-3-em-4-carboxylate, 1β-oxide (9.584 g., 20 mmole) in dry, ethanol-free chloroform (300 ml.) was heated to reflux in an atmosphere of nitrogen, and illuminated by fluorescent strip-lighting (8 × 40-watt lamps). N-Bromosuccinimide (890 mg., 5 mmole) was added and the mixture refluxed for 1¾hr., further portions of N-bromosuccinimide (6 × 890 mg.) being added at intervals of 15 min. The reaction was then evaporated to a brown gum. This gum was dissolved in methylene chloride - acetone (9:1 respectively, 50 ml.) and chromatographed on Kieselgel G (0.05 - 0.2 mm., 400 g.) with methylene chloride - acetone (9:1) as eluent. In this way the 3-bromomethyl compound (2.35 g., 21%) was obtained as a cream solid, m.p. 153° - 162°, $[\alpha]_D$ + 35° (c 0.78), $\lambda_{max.}$ 283 nm ($E_{1cm}^{1\%}$ 159). The chromatography fractions immediately before those containing the above material were triturated with acetone - ether (1:1) to remove less polar contaminants. This afforded a further amount of the 3-bromomethyl compound (600 mg., 11%) as a cream solid, m.p. 144° - 157°, $[\alpha]_D$ + 31°, $\lambda_{max.}$ 283 nm ($E_{1cm}^{1\%}$ 165). A small sample of this product was recrystallised from acetone - ether (2:1) to give the 3-bromomethyl compound as white crystals, m.p. 163° - 166°, $[\alpha]_D$ + 32°, $\lambda_{max.}$ 284 nm (ε 9,500), $\nu_{max.}$ 1784 (azetidin-2-one), 1783 ($CO_2R$), 1654 and 1526 (CONH), and 1036 cm.$^{-1}$ (S → O), τ 1.48 (1H,d, J 8 Hz; -NH), 2.72 (5H,s; $C_6H_5$), 4.11 (1H,dd; J 4.5; and 8 Hz; $C_7$-H), 4.75 and 4.93 (2H, AB-q, J 12 Hz; $CH_2CCl_3$), 5.00 (1H,d, J 4.5 Hz; $C_6$-H), 5.34 and 5.50 (2H, AB-q, J 10 Hz; $CH_2Br$), 5.97 and 6.22 (2H, AB-q, J 18 Hz; $C_2$-H_2), 6.26 and 6.47 (2H, AB-q, J 14 Hz; $C_6H_5CH_2$) (Found: C, 38.6; H, 2.7; N, 4.8; S, 5.8; total halogen content, 3.95 equiv./mole compound. $C_{18}H_{16}BrCl_3N_2O_5S$ (558.7) requires: C, 38.7; H, 2.9; N, 5.0; S, 5.7%; total halogen content, 4.00 equiv./mole compound (ii) Photo-initiated bromination with N-bromosuccinimide in chloroform at 15°

A solution of 2,2,2-trichloroethyl 3-methyl-7β-phenylacetamidoceph-3-em-4-carboxylate, 1β-oxide (50 mg., 0.104 mmole and N-bromosuccinimide (18.5 mg., 0.104 mmole) in dry, ethanol-free chloroform (2.5 ml.) was kept at 15° in a stoppered tube and illuminated with tungsten light (1 × 100-Watt bulb) for 22 hr. Examination by TLC revealed the presence of the title compound in the reaction mixture. Identification of the title compound on the TLC plate was made by comparing the $R_F$ with that of material obtained in B2 (i) above, and by its characteristic pink colour when sprayed with pyridine, warmed at 60°–80° for 5 min., the excess of pyridine evaporated, and the plate then sprayed with iodoplatinate reagent.

(iii) Bromination with N-bromosuccinimide initiated by azobisisobutyronitrile in refluxing chloroform A solution of 2,2,2-trichloroethyl 3-methyl-7β-phenylacetamidoceph-3-em-4-carboxylate, 1β-oxide (102.5 mg., 0.214 mmole), N-bromosuccinimide (56 mg., 0.311 mmole) and azobisisobutyronitrile (5 mg.) in dry, ethanol-free chloroform (5 ml.) was protected from the light, and heated to reflux. After 2½ hr. a further portion of N-bromosuccinimide (20 mg., 0.111 mmole) was added, refluxing continued until a total of 4.5 hr. had elapsed from the start of the reaction. The solution was cooled and applied to a preparative thin-layer plate (20 × 20 cm. coated with Kieselgel $HF_{254+366}$, 2 mm. thick); the plate was developed with methylene chloride - acetone (4:1). The appropriate band was removed and extracted with methylene chloride - acetone (1:1, 100 ml.). Evaporation of the organic solution afforded the title compound (36 mg., 30%), m.p. 144°–9°, $\lambda_{max.}$ 283 nm ($E_{1cm}^{1\%}$ 151).

(iv) Bromination with molecular bromine, activated by light

A solution of 2,2,2-trichloroethyl 3-methyl-7β-phenylacetamidoceph-3-em-4-carboxylate, 1β-oxide (500 mg., 1.04 mmole) in dry, ethanol-free chloroform (25 ml.) was heated to reflux in an atmosphere of nitrogen and illuminated with tungsten light (1 × 100-watt bulb). To this refluxing solution was added a solution of bromine (0.1 ml., 312 mg., 1.73 mmole) in dry, ethanol-free chloroform (10 ml.) over a period of 70 min. After the reaction had proceeded for 95 min., the solvent was evaporated, and the residual oil purified by chromatography on Kieselgel G (0.05 - 0.2 mm., 50 g.) using methylene chloride - acetone (9:1) as eluent. The appropriate fractions from the chromatography were combined to give the 3-bromomethyl compound (198 mg., 34%) as pale yellow crystals, m.p. 158°–160°, $\lambda_{max.}$ 283 nm ($E_{1cm}^{1\%}$ 171). A small sample of this product was recrystallised from acetone - petroleum ether (b.p. 60° to 80°) to give white needles, m.p. 163°–8°, $[\alpha]_D$ + 32° (c 0.69), $\lambda_{max.}$ 284 nm (ε 9,500) (Found: C, 38.7; H, 2.9; N, 4.9; S, 5.7; total halogen content, 3.92 equiv./mole compound. $C_{18}H_{16}BrCl_3N_2O_5S$ (558.7) requires: C, 38.7; N, 2.9; N, 5.0; S, 5.7%; total halogen content, 4.00 equiv./mole compound).

(v) Bromination with N-bromocaprolactam

A solution of 2,2,2-trichloroethyl 3-methyl-7β-phenylacetamidoceph-3-em-4-carboxylate, 1β-oxide (97 mg., 0.202 mmole) and N-bromocaprolactam (44 mg., 0.23 mmole) in dry, ethanol-free chloroform (5 ml.) was heated under reflux, in an atmosphere of nitrogen, and illuminated with tungsten light (1 × 100-watt bulb) for 2 hr. The golden solution was then cooled and applied to a preparative thin-layer plate (20 × 20 cm., coated with Kieselgel HF$_{254+366}$, 2 mm. thick), and the plate was eluted with methylene chloride - acetone (4:1). The band of R$_F$0.35 was removed and extracted with methylene chloride - acetone (1:1, 250 ml.). Evaporation of the filtrate so obtained afforded starting material (21 mg., 22%) as a cream solid, $\lambda_{max.}$ 269 nm (E$_{1cm}^{1\%}$ 159). The band of R$_F$ 0.5, when treated in a similar manner, yielded the 3-bromomethyl compound (17 mg., 15%) as a cream solid, $\lambda_{max.}$ 283 nm (E$_{1cm}^{1\%}$ 153).

(vi) Bromination with N-bromophthalimide

A solution of 2,2,2-trichloroethyl 3-methyl-7β-phenylacetamidoceph-3-em-4-carboxylate, 1β-oxide (102 mg., 0.21 mmole) and N-bromophthalimide (72 mg., 0.30 mmole) in dry, ethanol-free chloroform (5 ml.) was heated under reflux, in an atmosphere of nitrogen, and illuminated with tungsten light (1 × 100-watt bulb) for 5½ hr. The reaction mixture was cooled and applied to a preparative thin-layer plate (20 × 20 cm coated with Kieselgel HF$_{254+366}$, 2 mm. thick), and the plate was eluted with methylene chloride - acetone (4:1). Work-up of the appropriate bands afforded starting material (63 mg., 50% based on E$_{1cm.}^{1\%}$ values), $\lambda_{max.}$ 270 nm (E$_{1cm}^{1\%}$ 129), and the 3-bromomethyl compound (61 mg., 32.5% based on E$_{1cm.}^{1\%}$ values), $\lambda_{max.}$ 284 nm (E$_{1cm.}^{1\%}$ 111). Both compounds were obtained as white solids contaminated with phthalimide.

(vii) By Photochemically-initiated bromination at 20° in 1,2-dichloroethane.

A solution of 2,2,2-trichloroethyl 3-methyl-7β-phenylacetamidoceph-3-em-4-carboxylate, 1β-oxide (5 g., 10.4 mmole) in 1,2-dichloroethane (400 ml.) was stirred at 20°, under a dry nitrogen atmosphere, with N-bromosuccinimide (2.80 g., 15.7 mmole; 1.51 eq.). The mixture was illuminated with a Hanovia 125-watt medium pressure mercury arc using a Pyrex-filter, the temperature being maintained at 20° throughout the reaction. After 3 hours the solution was washed with water (2 × 100 ml.) and the aqueous layers collectively washed with 1,2-dichloroethane (50 ml.). The combined organic layers were dried and evaporated leaving a brown gum which was chromatographed on Kieselgel G (150-200 g.), with methylene chloride - acetone (9:1) as solvent. The appropriate fractions were combined and evaporated, then triturated with methanol and re-evaporated to provide the *title compound* as an off-white solid (2.501 g., 43%), m.p. 158°-165° (dec.), [α]$_D$ + 31°, $\lambda_{max.}$ 282.5 nm (E$_{1cm}^{1\%}$ 170). Fractions collected before those containing the title compound were evaporated and triturated with methanol to provide a crude sample of 2,2,2-trichloroethyl 3-bromomethyl-7β-(DL-2-bromo-2-phenylacetamido)ceph-3-em-4-carboxylate, 1β-oxide as a pale yellow solid (0.643 g.), m.p. 183°-6°, [α]$_D$ + 15.9°, $\lambda_{max.}$ 278.5 nm (E$_{1cm}^{1\%}$ 147) identified by TLC and PMR by comparison with an authentic sample.

(viii) By photochemically-initiated bromination at 0° in 1,2-dichloroethane

A solution of 2,2,2-trichloroethyl 3-methyl-7β-phenylacetamidoceph-3-em-4-carboxylate, 1β-oxide (5 g., 10.4 mmole) in 1,2-dichloroethane (400 ml.) was stirred at 0° under a dry nitrogen atmosphere with N-bromosuccinimide (2.80 g., 15.7 mmole; 1.51 eq.). The mixture was illuminated for 1 hour with a Hanovia 125-watt medium pressure mercury arc using a Pyrex filter, the temperature being maintained at 0° throughout the reaction. The solution was washed with water (2 × 100 ml.) and the combined aqueous layers washed with 1,2-dichloroethane (50 ml.). The combined organic layers were dried and evaporated to give a yellow oil which was chromatographed on Kieselgel G (160 g.), with methylene chloride - acetone (9:1) as solvent. In this way the title compound was obtained as an off-white solid (2.805 g., 48%), m.p. 156°-164° (dec.), [α]$_D$ 30° $\lambda_{max.}$ 283 nm (E$_{1cm}^{1\%}$ 171.5). Fractions collected before those containing the title compound were combined and triturated with methanol to give a crude sample of 2,2,2-trichloroethyl 3-bromomethyl-7β-(DL-2-bromo-2-phenylacetamido)ceph-3em-4-carboxylate 1β-oxide (1.256 g.), m.p. 180°-6° (dec.), [α]$_D$ + 9.8° (C 0.48), $\lambda_{max.}$ 278.5 nm (E$_{1cm.}^{1\%}$ 139), identified by TLC and PMR by comparison with an authentic sample.

(ix) By photochemically-initiated bromination at −20° in 1,2-dichloroethane

A solution of 2,2,2-trichloroethyl 3-methyl-7β-phenylacetamidoceph-3-em-4-carboxylate, 1β-oxide (5.0 g., 10.4 mmole) in 1,2-dichloroethane (400 ml.) was stirred at −20° under a dry nitrogen atmosphere with N-bromosuccinimide (2.78 g., 15.6 mmole; 1.5 eq.). The mixture was illuminated for 3½ hours with Hanovia 125-watt medium pressure mercury arc, the temperature being maintained at −20° throughout. The solution was then washed with water (2 × 200 ml.) and the combined aqueous layers washed with dichloroethane (50 ml.). The combined organic layers were dried an evaporated to give an orange solid which was chromatographed on Kieselgel G (250 g.) with methylene chloride - acetone (9:1) as solvent. In this way the title compound was obtained in two batches, both as off-white solids, having the following respective constants:
(i) (0.904 g., 15.5%), m.p. 150°-155° (dec), [α]$_D$ + 31.5° $\lambda_{max.}$ 282.5 nm (E$_{1cm.}^{1\%}$ 165), (ii) (2.306 g., 39.8%), m.p. 156-168° (dec), [α]$_D$ 36.7°, $\lambda_{max.}$ 282.5 nm (E$_{1cm.}^{1\%}$ 168).

Fractions eluted before those containing the title compound were combined, evaporated, and triturated with methanol to give 2,2,2-trichloroethyl 3-bromomethyl-7β-(DL-2-bromophenylacetamido)ceph-3-em-4-carboxylate, 1β-oxide (0.751 g., 11.3%9, m.p. 191°-2° (dec.), [α]$_D$ + 5.1°, $\lambda_{max.}$ 281.5 nm (E$_{1cm.}^{1\%}$ 152).

(x) Photoinitiated bromination with N-bromosuccinimide in refluxing benzene

A solution of 2,2,2-trichloroethyl 3-methyl-7β-phenylacetamidoceph-3-em-4-carboxylate, 1β-oxide (5 g., 10.4 mmole) in benzene (500 ml.) was stirred and heated to reflux in an atmosphere of nitrogen, and illuminated with fluorescent striplighting (8 × 40-watt lamps). N-Bromosuccinimide (3 g., 16.85 mmole) was added and the mixture refluxed for 30 minutes, then evaporated. The residual yellow gum was dissolved in methylene chloride - acetone (10:1, 10 ml.) and chromatographed on Kieselgel-G (0.05 - 0.2 mm; 150 g.), with methylene chloride - acetone (10:1) as eluent. In this way the 3-bromomethyl compound (2.40 g., 41%) was obtained as a cream solid, m.p. 150°-155°, [α]$_D$ + 31°, $\lambda_{max.}$ 283 nm (E$_{1cm.}^{1\%}$ 164). This product showed TLC behaviour and gave infrared and p.m.r. spectra identical with those of an authentic sample of the product.

The chromatogrphy fractions before those which contained the 3-bromomethyl product were combined and triturated with acetone - ether to give 2,2,2-trichloroethyl 3-bromomethyl-7β-(DL-2-bromophenylacetamido)-ceph-3-em-4-carboxylate, 1β-oxide (380 mg.) as a white solid, m.p. 190°-2° (dec.), $[\alpha]_D$ + 15.3°, $\lambda_{max.}$ 282 nm ($E_{1cm}^{1\%}$ 163), $\nu_{max.}$ (CHBr$_3$) 3350 (NH), 1798 (azetidin-2-one), 1735 (CO$_2$R), 1670 and 1510 (CONH), 1045 cm.$^{-1}$ (S→O), $\tau$ 1.09 (1H, d, J 8 Hz; N$\underline{H}$), 2.42 and 2.64 (5H,two m; C$_6$H$_5$), 4.00 (1H,s; C$_6$H$_5$-C$\underline{H}$Br-), 4.08 (1H,dd, J 4.5 and 8 Hz;, C$_7$-$\underline{H}$), 4.75 and 4.93 (2H, AB-q,J 12 Hz; -C$\underline{H}_2$CCl$_3$), 4.90 (1H,d,J 4.5 Hz; C$_6$-$\underline{H}$), 5.29, 5.45 and 5.34, 5.49 (two AB-q totalling 2protons, arising because the product is a diastereomeric mixture, J 12 Hz; -CH$_2$Br), 5.85 and 6.10 (two AB-q totalling 2-protons, J 19 Hz; C$_2$-$\underline{H}_2$). Recrystallization of a small sample gave the analytical specimen, m.p. 193°-4° (dec., ($[\alpha]_D$ + 21.2° $\lambda_{max.}$ 284 nm ($\epsilon$ 10,400) (Found: C, 34.4; H, 2.4; N, 4.1; S, 5.3; total halogen content, 4.88 equiv./mole compound. C$_{18}$H$_{15}$Br$_2$Cl$_3$N$_2$O$_5$S (639.6) requires: C, 33.9; H, 2.4; N, 4.4; S, 5.0%; total halogen content, 5.00 equivs./mole compound).

Evaporation of the mother liquors of the dibromo-compound yielded 2,2,2-trichloroethyl 2β-bromo-3-metyl-7β-phenylacetamidoceph-3-em-4-carboxylate, 1β-oxide ( 1.33 g.) as a yellow foam $[\alpha]_D$ − 121° (CHCl$_3$), 80$_{max.}$ 289 nm ($\epsilon$6,590), $\nu_{max.}$ (CHBr$_3$) 3350 (NH), 1798 (azetidin-2-one), 1735 (CO$_2$R), 1670 and 1510 (CONH), 1045 cm.$^{-1}$ (S→O), $\tau$(CDCl$_3$) 2.70 (5H, s; C$_6$$\underline{H}_5$-), 3.40 (1H, d, J 10 hz, N$\underline{H}$), 3.87 (1H,dd,J10 and 4.5 Hz; C$_7$-$\underline{H}$), 4.86 (1H,d. J 4.5 Hz; C$_6$-$\underline{H}$), 4.91 (1H,s; C$_2$-$\underline{H}$), 5.01 and 5.16 (2H, AB-q J 12 Hz; C$\underline{H}_2$CCl$_3$), 6.37 (2H,s; C$_6$H$_5$C$\underline{H}_2$), 7.70 (3H,s, C$_3$-C$\underline{H}_3$). The crude foam gave a total halogen analysis of 4.05 equivs./mole compound.

EXAMPLE B3

Bromination of 2,2,2-trichloroethyl 7β-formamido-3-methylceph-3-em-4-carboxylate, 1β-oxide (i) to give 2,2,2-trichloroethyl 3-bromomethyl-7β-formamido-ceph-3-em-4-carboxylate, 1β-oxide (i) By photochemically-initiated bromination in refluxing chloroform.

A solution of 2,2,2-trichloroethyl 7β-formamido-3-methylceph-3-em-4-carboxylate, 1β-oxide hemi-ethanol solvate (2.065 g., 5 mmole) in chloroform (200 ml) was washed with water (3 × 100 ml) to remove the ethanol, dried and concentrated to ca. 100 ml. N-Bromosuccinimide (1.435 g. 7.5 mmole) was added, and the reaction mixture was heated under reflux for 30 minutes in a stream of nitrogen while being illuminated by 8 × 40-watt tungsten strip-lights, when TLC (acetone-methylene chloride; 1:4, run twice) showed the presence of less polar products, together with a trace of starting material. The reaction mixture was washed with water (2 × 100 and 1 × 50 ml) to remove succinimide, dried and evaporated. The residual foam was dissolved in the minimum volume of acetone-methylene chloride (1:4) and chromatographed on Kieselgel G (TLC grade; 100 g) with acetone-methylene chloride (1:4; 500 ml) and then acetone-methylenechloride (1:2) as eluant. Fractions of 25 ml were collected and examined by TLC (acetone-methylene chloride; 1:4). The appropriate fractions were combined and evaporated to give an off-white solid (1.08 g) which was triturated with a mixture of ether (40 ml) and acetone (5 ml) to give the title compound (0.95 g, 40%), m.p. 172°-174° (dec.), $\lambda_{max}$ 283 nm ($E_{1cm}^{1\%}$ 201), part (154 mg) of which was recrystallized from a mixture of warm chloroform (25 ml) and light petroleum (b.p. 40°-60°; 10 ml) to give an analytical sample (121 mg), m.p. 173°-174° (dec.), $[\alpha]_D$ + 4.3°., $\lambda_{max}$ 283 nm ($\epsilon$ 9,980), $\nu_{max}$ 3265 (NH), 1785 (azetidin-2 -one), 1735, 1720 and 1240 (CO$_2$R), 1660 and 1530 (CONH), and 1030 cm.$^{-1}$ (S→O), $\tau$ 1.58 (1H,d, J 9 Hz; N$\underline{H}$), 1.84 (1H,s; C$\underline{H}$O), 3.99 (1H,dd, J 9,5 Hz; C$_7$—$\underline{H}$), 4.77 and 4.95 (2H,Ab-q,J 12 Hz; CO$_2$C$\underline{H}_2$CCl$_3$), 4.94 (1H,d, J 5 hz; C$_6$-$\underline{H}$), 5.33 and 5.47 (2H, AB-q,J 10 Hz; C$_3$—CH$_2$ Br), 5.93 and 6.20 (2H, AB-q,J 18 Hz; C$_2$—$\underline{H}_2$) (Found: C, 28.1; H, 2.1; N, 6.0; S, 6.9; total halogen content, 4.00 equiv./mole compound. C$_{11}$H$_{10}$BrCl$_3$N$_2$O$_5$S (468.6) requires C, 28.2; H, 2.15; N, 6.0; S, 6.8%. total halogen content 4.00 equiv./mole compound).

(ii) By photochemically-initiated bromination at 12°

A solution of 2,2,2-trichloroethyl 7β-formamido-3-methylceph-3-em-4-carboxylate, 1β-oxide (5g; 12.85 mmole) in 1,2-dichloroethane (125 ml, dried by passing through basic alumina) was cooled to 0° and stirred, under an atmosphere of dry nitrogen, with N-bromosuccinimide (3.42 g; 19.25 mmole; 1.5 equiv). The mixture was illuminated by a Phillips 125-watt medium pressure U.V. lamp using a Pyrex-filter. The temperature of the reaction rose to 12° , and was maintained thereat until the completion of the reaction, as determined by TLC. The mixture was then washed with water (3 × 50 ml) and the aqueous layers washed with 1,2-dichloroethane (50 ml). The combined organic layers were dried and concentrated to approximately 10 ml, when crystallization commenced. The mixture was chilled overnight and then filtered. The solid was washed with dichloroethane-ether mixture (1:1, 5ml.) then with ether, then dried at 40° in vacuo. The title compound was obtained as a white powder (3.23 g; 53.5%), m.p. 160°-2° (dec), $[\alpha]_D$ −4.1°, $\lambda_{max}$ 282.5 nm ($E_{1cm}^{1\%}$ 196). The product was similar in PMR spectrum and R$_F$ values to that of Example B3 (i).

(iii) By photochemically-initiated bromination at 0°

A solution of 2,2,2-trichloroethyl 7β-formamido-3-methylceph-3-em-4-carboxylate, 1β-oxide (4.223g; 10.83 mmole) in dry 1,2-dichloroethane (400 ml) was cooled to 0°, under a dry nitrogen atmosphere, and stirred with N-bromosuccinimide (2.89 g; 16.28 mmole: 1.5 eq). The temperature of the mixture was maintained at 0° whilst it was illuminated by a Hanovia 125-watt medium pressure UV lamp with a Pyrex-filter. After 1hr. the reaction solution was washed with water (3 × 100 ml) and the aqueous layers washed with 1,2-dichloroethane (50 ml). The combined organic layers were dried and evaporated, leaving a pale-yellow sticky solid which was triturated with methanol (25 ml) to provide the title compound as a cream solid (2.405 g; 47.5%), m.p. 148°-155° (dec), $\lambda_{max}$ 283 nm ($E_{1cm}^{1\%}$ 198). The filtrate from this trituration was chromatographed on Kieslgel G with methylene chloride:acetone (1:1) as solvent, to provide a further amount of the title compound as a cream solid (1.215 g; 23.9%), m.p. 132°-140° (dec), $\lambda_{max}$ 283 nm ($E_{1cm}^{1\%}$ 182). Both samples of the product were similar in PMR spectra and R$_F$ values as sample prepared in Example B3 (i).

(iv) By photochemically-initiated bromination at −20°

A solution of 2,2,2-trichloroethyl 7β-formamido-3-methylceph-3-em-4-carboxylate, 1β-oxide (10 g; 25.7 mmole) in dry 1,2-dichloroethane (400 ml) was cooled to −20° under a dry nitrogen atmosphere. N-bromosuccinimide (4.80 g; 27.0 mmole; 1.08 eq) was stirred into the solution which was then illuminated for 4 hours with a Hanovia 125-watt medium pressure UV lamp with a Pyrex-filter, the temperature being maintained at −20° throughout. The mixture was then allowed to warm to 10° and washed with brine (3 × 50 ml), and the aqueous layer extracted with 1,2-dichloroethane (50 ml). The combined organic layers were dried and concentrated to approximately 100 ml, then chilled. The title compound, obtained by filtration, was a white solid (8.446 g; 70%), m.p. 160°–165° (dec), $[\alpha]_D$ +4.7° $\lambda_{max}$ 282 nm ($E_{1cm}^{1\%}$194). The PMR spectrum of this product showed it to contain 7% of the starting material, the presence of which was confirmed by TLC analysis. The mother liquors of the product were chromatographed on Kieselgel G with methylene chloride-acetone (1:1) as solvent; in this way, a further amount of the title compound was obtained (0.785 g; 6.5%); m.p. 167°–170° (dec), $[\alpha]_D$ + 3.3°, $\lambda_{max}$283 nm ($E_{1cm}^{1\%}$211). This sample of the product was similar in its PMR spectrum and $R_F$ values to the sample obtained in Example B3(i). Also obtained from the chromatography was an amount of starting material (0.300 g; 3% input material), m.p. 168°–170° (dec), $\lambda_{max}$ 269 nm ($E_{1cm}^{1\%}$ 184).

(v) Bromination with photochemical initiation provided by tungsten light (a) N-Bromosuccinimide (6.05 g, 1.5 equiv.) was added to a stirred solution of 2,2,2-trichloroethyl 7β-formamido-3-methylceph-3-em-4-carboxylate, 1β-oxide (8.86 g, 22.7 mmole) in dry 1,2-dichloroethane (400 ml) at 0° in a dry nitrogen atmosphere. The temperature was maintained at 0° ± 5° and irradiated for 2hr. with 6 tungsten bulbs (150 watt), then with 3 tungsten bulbs for a further 2¼ hr. The orange solution was washed with dilute sodium acetate solution (200 ml), water (200 ml), combined with the 1,2-dichloroethane backwash (200 ml) of the combined aqueous layers, dried and evaporated to low volume to give the title compound as an off-white solid (6.36 g, 60%), $\lambda_{max.}$ 282 nm ($E_{1cm}^{1\%}$ 204).

(b) A solution of 2,2,2-trichloroethyl 7β-formamido-3-methylceph-3-em-4-carboxylate, 1β-oxide (10.0 g, 25.6 mmole) in dry 1,2-dichloroethane (400 ml) was reacted with N-bromosuccinimide (6.84 g, 1.5 equiv.) under a dry nitrogen atmosphere as in a) using tungsten light (3 × 150 watt bulbs) for 1hr. at −10°± 5°, then for 4hr. at −20°. The title compound was obtained, by a procedure as described in a) as an off-white solid (7.71 g, 64.4%), $\lambda_{max}$ 283 nm ($E_{1cm}^{1\%}$201)

(c) A solution of 2,2,2-trichloroethyl 7β-formamido-3-methylceph-3-em-4-carboxylate, 1β-oxide (8.86 g, 22.7 mmole) in dry 1,2-dichloroethane (400 ml) was reacted with 1,3-dibromo-5,5-dimethylhydantoin (4.87 g, 0.75 equiv.) in a dry nitrogen atmosphere using tungsten light initiation (3 × 150 watt bulbs) at 0° for ½ hr, then at −20° for 5 hr. Isolation, as described in a) gave the title compound as an off-white solid (6.476 g, 61%9, $\lambda_{max}$ 282.5 nm ($E_{1cm}^{1\%}$ 199).

(d) A solution of 2,2,2-trichloroethyl 7β-formamido-3-methylceph-3-em-4-carboxylate, 1β-oxide (4.52 g, 11.5 mmole) in 1,2-dichloroethane (250 ml) was stirred with sodium acetate solution (15 ml, 4.25 molar (buffered to pH 7 by the addition of glacial acetic acid. This two-phase solution was then reacted with 1,3-dibromo-5,5-dimethylhydantoin (2.74 g, 0.83 equiv.) in a dry nitrogen atmosphere at 0°, using tungsten-light initiation (3 × 150 watt bulbs), for 1½ hr. The title compound was isolated as in a) as an off-white solid (3.769 g, 70%), $\lambda_{max}$ 282.5 nm ($E_{1cm}^{1\%}$ 196)

(vi) Bromination using 125-watt medium pressure Mercury arc-Pyrex filter in 1,2-dichloroethane and a variety of bromination agents.

| | Conc$^n$ of (I) in g/100 ml. | Vol. of 1,2-di-chloro-ethane in ml. | Molar equiv. | Brominating Agent | Temp. | Time in Hr. |
|---|---|---|---|---|---|---|
| a | 2 | 300 | 1.5 | N-Bromosuccinimide | 0 | 3½ |
| b | 2 | 300 | 1.5 | N-Bromosuccinimide + 1 ml H$_2$O | 0 | 1¼ |
| c | 2 | 300 | 1.5 | N-Bromoacetamide | −20 | 14 |
| d | 2 | 300 | 1.5 | N-Bromocaprolactam | 0 | 5¼ |
| e | 2 | 300 | 1.5 | N-Bromophthalimide | 0 | 4½ |
| f | 2 | 300 | 0.75 | 1,3-Dibromo-5,5-dimethylhydantoin | 0 | 1¾ |
| g | 2 | 300 | 0.75 | 1,3-Dibromo-5,5-dimethylhydantoin + 3 ml H$_2$O | 0 | 1 |

| | (II)$^+$ | | | |
|---|---|---|---|---|
| | % Yield | m.p. | $[\alpha]_D$ | $E_{1cm}^{1\%}$ at 282–3nm |
| a | 56.5 | 164–165° | +0.3° | 201 |
| b | 55 | 169–171° | −3.5° | 194 |
| c | 44.7 | 161–165° | +0.85° | 199 |
| d | 50.8 | 168.5–170.5° | +0.5° | 199 |
| e | 55.8* | 162–164° | +1.6° | 194 |
| f | 55 | 168–170° | −5.15° | 204 |
| g | 58 | 164– | −5.5° | 194 |

-continued

165°

| | Conc.^n of (I) in g/100 ml. | Vol. of 1,2-dichloroethane in ml. | Molar equiv. | Brominating Agent | Temp. | Time in Hr. |
|---|---|---|---|---|---|---|
| h | 2 | 250 | 0.75 | 1,3-Dibromo-5,5-dimethylhydantoin + $Na_2CO_3$(1 eq) + 4 ml $H_2O$ | 0 | ¼ |
| i | 2 | 250 | 0.75 | 1,3-Dibromo-5,5-dimethylhydantoin + ml $H_2O$ | −17 | 1½ |
| j | 2 | 300 | 0.75 | 1,3-Dibromo-5-ethyl 5-methylhydantoin | 0 | 2½ |
| k | 2 | 300 | 0.75 | 1,3-Dibromo-5-isopropyl-5-methyl hydantoin | 0 | 1¼ |
| l | 2 | 250 | 1.5 | Bromine | 0 | 4 |
| m | 2 | 250 | 1.5 | 1,3,5-Tribromo-1,2,4-triazole | 0 | 3 |

(II)+

| | % Yield | m.p. | $[\alpha]_D$ | $E^{1\%}_{1cm}$ at 282-3 nm |
|---|---|---|---|---|
| h | 59.5 | 165–168° | −9.6° | 203 |
| i | 65.3 | 170–171° | −0.2° | 201 |
| j | 53 | 164–166° | −2.7° | 197 |
| k | 50.8 | 167–170° | −5.6° | 201 |
| l | ⌽12.6± | 160–170° | +1.85° | 212 |
| m | ⌽35.5∞ | 161–164° | +1.5° | 212 |

+Isolated after an aqueous wash, by concentration of the solution.
*Contaminated with phthalimide
±30% (I) recovered although all $Br_2$ was consumed
∞13% (I) recovered
⌽Product isolated by chromatography on Kieselgel G.

(vii) Bromination at −20° with photochemical initiation at 350 nm

N-Bromosuccinimide (27.4 g, 1.5 equiv.) was added to a stirred solution of 2,2,2-trichloroethyl 7β-formamido-3-methylceph-3-em-4-carboxylate, 1β-oxide (40 g, 0.103 mole) in dry 1,2-dichloroethane (2 l) cooled to −20° in an atmosphere of dry nitrogen. This mixture was circulated at −20° for 9 hr. through a Pyrex jacket surrounding an Atlas 40-watt ultraviolet tube peaking at 350 nm. The dark orange reaction solution was washed with water (3 × 1 l), combined with the 1,2-dichloroethane backwash (1 l) of the combined aqueous washings, dried and evaporated to low volume to give the title ester, 1β-oxide as an off-white solid (24.46 g, 51%), m.p. 160° to 162°, $[\alpha]_D$ − 6°,$\lambda_{max.}$ 282 nm ($E_{1cm}^{1\%}$ 202).

EXAMPLE B4

Bromination of t-Butyl 7β-formamido-3-methylceph-3-em-4-carboxylate, 1β-oxide to give t-butyl-3-bromomethyl-7β-formamidoceph-3-em-4-carboxylate, 1β-oxide (i) By photochemical initiated bromination at reflux A suspension of t-butyl 7β-formamidoceph-3-em-4-carboxylate, 1β-oxide (314 mg, 1 mmole) and N-bromosuccinimide (287 mg. 1.5 equiv.) in benzene (50 ml) was heated under reflux for 30 minutes in a stream of dry, oxygen-free nitrogen while being illuminated by 8 × 40-watt tungsten strip-lights. The benzene was removed in vacuo and the residue was dissolved in acetone-methylene chloride (1:4 ; 5 ml) and chromatographed on Kieselgel G (TLC grade; 40 g) using acetone-methylene chloride (1:4) as eluant. Fractions of 10 ml were collected and examined by TLC (acetone-methylene chloride, 1:2). Fractions 29-45 were combined and evaporated to give a pale-orange solid (171 mg),$\lambda_{max}$ 278.5 nm ($E_{1cm}^{1\%}$ 208), which was dissolved in acetone (ca. 4 ml.). Addition of light petroleum (b.p. 40°-60°; ca. 5 ml) precipitated the bromo-ester as an off-white gelatinous solid (117 mg. 30%), m.p. softens at ca. 175° decomposes above 200°, $[\alpha]_D$ + 26.5°,$\lambda_{max}$ 278 nm (ε10,150), $\nu_{max}$ 3320 (NH) 1770 (azetidin-2-one), 1716 ($CO_2R$), 1682 and 1526 (CONH), and 1021 $cm^{-1}$ (S→0), τ 1.64 (1H,d, J 9 Hz; NH). 1.82 (1H,s, NHCHO), 4.03 (1H,dd, J 9, 5 Hz; $C_7$-H), 5.01 (1H,d, J 5 Hz; $C_6$-H), 5.37, 5.61 (2H, AB-q, J 10 Hz; $C_3$-$CH_2$Br). 6.02, 6.30 (2H, AB-q, J 18 Hz; $C_2$-$H_2$), 8.50 (9H,s; $CO_2C(CH_3)_3$).

(ii) By photochemically-initiated bromination at −20°

A suspension of t-butyl 7β-formamido-3-methylceph-3-em-4-carboxylate, 1β-oxide (7.55 g, 24 mmole) in dry 1,2-dichloroethane (420 ml) was stirred at 25° and then briefly warmed to 60° to achieve complete solution. The solution was allowed to cool to ca. 30°, and N-bromosuccinimide (6.41 g, 36 mmole), was added. The solution was cooled under a dry nitrogen atmosphere to −20° and illuminated for 3¼ hours with a Hanovia 125-watt medium pressure mercury arc with a Pyrex-filter, the temperature being maintained in the range −15° to −20° throughout. The solution was washed with 0.5 M-aqueous sodium acetate solution (100 ml) and water (100 ml), dried and evaporated. The residual gelatinous solid was dissolved in chloroform (ca. 50 ml) and chromatographed on a column (i.d. 9.5 cm) of Kieselgel (0.05 to 0.2 mm; 200 g). Elution with chloroform-ethyl acetate (1:1; 1 l) and ethyl acetate (100 ml) gave a yellow gum which was triturated with ether (20 ml) to give t-butyl 2β-bromo-3-bromomethyl-7β-formamidoceph-3-em-4-carboxylate, 1β-oxide as a pale yellow solid (1.43 g, 13%), m.p. 128° to 130°, $\lambda_{max}$ 295 nm ($E_{1cm}^{1\%}$ 181), part (300 mg) of which was triturated with a mixture of ether (ca. 8 ml), and methanol (ca. 1 ml) to give an analytical sample as a white solid (115 mg), m.p. 132° to 134°, $[\alpha]_D - 232°$, $\lambda_{max}$ 295 nm (ε 8.650), $\nu_{max}$(CHBr$_3$) 3400 (NH), 1810 (azetidin-2-one), 1730 (CO$_2$R), 1702 and 1512 (CONH) and 1060 cm$^{-1}$(S→0), τ1.44 (1H,d, J 9 Hz; NH), 1.83 (1H,s; CHO), 3.83 (1H,s; C$_2$H), 3.94 (1H,dd, J 9.5 Hz; C$_7$-H), 4.59 (1H,d, J 5 Hz; C$_6$-H), 5.56 (2H,s; C$_3$-CH$_2$Br), 8.45 (9H, s; Co$_2$CMe$_3$) (Found: C, 33.0; H, 3.4; Br, 32.9; N, 6.1; S, 6.6. C$_{13}$H$_{16}$Br$_2$N$_2$O$_5$S (472.2) requires C, 33.1; H, 3.4; Br, 33.9; N, 5.9; S, 6.8%). Further elution with ethyl acetate (700 ml) and then ethyl acetateacetone (2:1; 800 ml) gave first mixed fractions and then the title ester, 1β-oxide as a pale orange solid (4.82 g, 51%), m.p.≦200°, $\lambda_{max}$ 278 nm ($E_{1cm}^{1\%}$ 252), part (300 mg) of which was triturate with warm isopropanol (5 ml) containing a few drops of methanol to give a white solid (207 mg), m.p. >200°, $[\alpha]_D + 25°$,$\lambda_{max}$ 278 nm, (ε9,800), $\nu_{max}$ (CHBr$_3$)3440 (NH), 1802 (azetidin-2-one), 1720 (CO$_2$R), 1695 and 1508 (CONH) and 1038 cm$^{-1}$ (S→0) (Found : C, 39.6; H, 4.4; Br, 19.8; N, 7.1; S, 7.9. C$_{13}$H$_{17}$BrN$_2$O$_5$S (393.3) requires C,, 39.7; H, 4.4; Br, 20.3; N, 7.1; S, 8.15 %).

EXAMPLE B5

Bromination of 2,2,2-trichloroethyl 3-methyl-7β-phenoxyacetamido ceph-3-em-4-carboxylate, 1β-oxide to give 2,2,2-trichloroethyl 3-bromomethyl-7β-phenoxyacetamidoceph-3-em-4-carboxylate, 1β-oxide (i) Bromination at −10° to 0°.

A solution of 2,2,2-trichloroethyl 3-methyl-7β-phenoxyacetamidoceph-3-em-4-carboxylate, 1β-oxide (3.26 g; 6.56 mmole) in 1,2-dichloroethane (150 ml; dried by passing through basic alumina) was stirred with N-bromosuccinimide (1.76 g, 9.9 mmole, 1.5 eq.) in a dry nitrogen atmosphere and cooled to −10°. The reaction solution was illuminated with a medium-pressure mercury arc (125-watt) using a Pyrex filter for 1 hr. 25 minutess at between −10° and 0°. The mixture was then washed with water (3 × 75 ml) and the aqueous layers were back-extracted with 1,2-dichloroethane (75 ml). The combined organic layers were dried and evaporated to a yellow gum which was triturated with methanol to give the title compound as an off-white solid (2.12 g, 56.3%) m.p. 148° to 150°; $[\alpha]_D - 30.4°$,$\lambda_{max}$ 275 nm. ($E_{1cm}^{1\%}$ 161) inflexions at 271 nm ($E_{1cm}^{1\%}$ 145) and 280 nm ($E_{1cm}^{1\%}$ 153). Chromatography of the mother liquors afforded a further amount of the title compound (0.20 g, 5.3%), m.p. 152° to 155.5°, $[\alpha]_D - 36.3°$,$\lambda_{max}$ 276 nm ($E_{1cm}^{1\%}$ 161), inflexions at 272 nm ($E_{1cm}^{1\%}$ 146) and 281 nm ($E_{1cm}^{1\%}$ 159). Recrystallisation of a small amount of the title compound from methanol gave an analytical sample, m.p. 157° to 161°, $[\alpha]_D - 36°$,$\lambda_{max}$. 276 nm (ε9,850), inflexions at 271 nm (ε8,650) and 282 nm (ε9,450), $\nu_{max}$. 3420 (NH), 1789 (azetidin-2-one), 1745 (CO$_2$R), 1702 and 1521 (CONH), 1024 cm.$^{-1}$)S→0); τ 1.83 (1H,d, J 9 Hz; NH), 2.60 to 3.15 (5H,m, C$_6$H$_5$), 3.86 (1H,dd, J 9 and 5 Hz; C$_7$-H), 4.74 and 4.91 (2H, AB-q,J 12 Hz; CH$_2$CCl$_3$), 4.88 (1H,d, J 5 Hz; C$_6$-H), 5.31 (2H,s; C$_6$H$_5$OCH$_2$), 5.40 (2H,s; CH$_2$Br), 5.87 and 6.17 (2H, AB-q,J 18 Hz; C$_2$H$_2$). (Found; C, 37.4; H, 2.8; N, 4.8; S, 5.6; total halogen content, 3.91 equiv./mole. C$_{18}$H$_{16}$BrCl$_3$N$_2$O$_6$S (574.7) requires C, 37.6; H, 2.8; N, 4.9; S, 5.6%; total halogen content 4 equiv./mole).

(ii) Bromination at −20°.

2,2,2-Trichloroethyl 3-methyl-7β-phenoxyacetamidoceph-3-em-4-carboxylate, 1β-oxide (10.78 g, 21.76 mmole) was reacted as in (i), except that the temperature was kept at −20°, to give the title compound (8.36 g, 69%), similar to that obtained in (i).

EXAMPLE B6

Bromination of 2,2,2-trichloroethyl 3-methyl-7β-[D-2-(2,2,2-trichloroethoxycarbonylamino)-2-phenylacetamido]-ceph-3-em-4-carboxylate, 1β-oxide to give 2,2,2-trichloroethyl 3-bromomethyl-7β-[D-2-(2,2,2-trichloroethoxycarbonylamino)-2-phenylacetamido]ceph-3-em-4-carboxylate, 1β-oxide N-Bromosuccinimide (1.87 g, 1.4 equiv.) was added to a solution of 2,2,2-trichloroethyl 3-methyl-7β-[D-2-phenyl-2-(2,2,2-trichloroethoxycarbonylamino)acetamido]ceph-3-em-4-carboxylate 1β-oxide (5.03 g, 7.5 mmole) in dry 1,2-dichloroethane (400 ml). The suspension was cooled to −30° under a dry nitrogen atmosphere and illuminated for 1 hour with a Hanovia 125-watt medium pressure UV lamp with a Pyrex-filter, the temperature being maintained between −20° and −30° throughout. TLC (acetone-methylene chloride; 1:19) indicated that little reaction had occurred so the temperature was raised to 0° and illumination was continued for a further 2 hours. The reaction mixture was washed with water (2 × 200 ml) and evaporated to an orange foam which was chromatographed on Kieselgel G (150 g) with acetone-methylene chloride (1:19) as eluent. The appropriate fractions where combined and evaporated to give the title compound as a yellow solid (2.44 g, 43.5%), m.p. 172° to 174°, $[\alpha]_D - 14°$,$\lambda_{max}$. 282 nm (ε 9,000), $\nu_{max}$ 3330 (NH), 1790 (azetidin-2-one), 1738 (CO$_2$R), 1706 and 1530 (NHCO$_2$R), 1660 and 1530 (CONH) and 1040 cm.$^{-1}$ (S→0), τ 1.54 (two superimposed 1H,d; NH), 2.6 (5H,m; C$_6$H$_5$), 4.06 (1H,dd; J 8.5 and 4.5 Hz; C$_7$H), 4.44 (1H,d, J 8 Hz; CH-NH), 4.78 and 4.95 (2H, AB-q, J 12 Hz; CO$_2$CH$_2$CCl$_3$), 5.04 (1H,d, J 4.5 Hz; C$_6$H), 5.19 (2H, s; NHCO$_2$CH$_2$CCl$_3$), 5.37, 5.53 (2H, AB-q, J 10 Hz; CH$_2$Br), 6.03, 6.29 (2H, AB-q, J 18 Hz; C$_2$-H$_2$). (Found: C, 34.45; H, 2.6; N, 5.1; S, 4.3; total halogen content, 6.8 equiv./mole compound. C$_{21}$H$_{18}$BrCl$_6$N$_3$O$_7$S (749.1) requires C, 33.7; H, 2.4; N, 5.6; S, 4.3%, total halogen content, 7.0 equiv./mole compound.) Subsequent fractions were evaporated to give unchanged starting material (;b 0.87 g, 17%), $\lambda_{max}$. 268.5 nm ($E_{1cm}^{1\%}$ 103).

EXAMPLE B7

Bromination of p-methoxybenzyl 3-methyl-7β-phenylacetamidoceph-3-em-4-carboxylate, 1β-oxide to give p-methoxybenzyl 3-bromomethyl-7β-phenylacetamidoceph-3-em-4-carboxylate, 1β-oxide A solution of p-methoxybenzyl 3-methyl-7β-phenylacetamidoceph-3-em-4-carboxylate, 1β-oxide (4.00 g, 8.55 mmole) in dry 1,2-dichloroethane (400 ml) was cooled to −20° in an atmosphere of dry nitrogen, N-bromosuccinimide (228 g, 1.5 equiv.) was added, and the mixture was illuminated with a Hanovia 125-watt medium pressure mercury arc using a Pyrex-filter for 2 hours, the temperature being kept at ca. −20° throughout. The fine precipitate that had separated was collected by filtration (1.80 g), $[\alpha]_D +$ 114°, $\lambda_{max}$ (0.1M pH 6 phosphate) 254 nm ($E_{1cm}^{1\%}$ 193) and 309.5 nm ($E_{1cm}^{1\%}$ 67), τ7.97 (s; $C_3$-$CH_3$), and the filtrate was washed with water (3 × 200 ml), combined with the dichloroethane back-wash (100 ml) of the combined aqueous washings, dried and evaporated to a red-black semi-solid. Trituration with methanol gave the title ester 1β-oxide as an off-white solid (254 mg, 5.4%), m.p. 171° to 174° (dec), $[\alpha]_D$ −28° ($Me_2NCHO$), $\lambda_{max}$ (MeOH) 225.5nm (ε 16,500) and 272.5 nm (ε 9,050), inflexion at 277.5 nm (ε 8.500), τ 1.64 (1H,d, J 9 Hz; $NH$), 2.63, 3.05 (4H,2d, J 9 Hz; $CH_2C_6H_4OCH_3$), 2.70 (5H,s; $C_6H_5$), 4.16 (1H,dd, J 9,5 Hz; $C_7$-$H$) 4.74 (2H,s; $CH_2C_6H_4$), 5.08 (1H,d, J 5 Hz; $C_6$-$H$), 5.38, 5.58 (2H, AB-q, J 11 Hz; $C_3$-$CH_2Br$), 6.06, 6.31 (2H, AB-q, J 18 Hz; $C_2$-$H_2$), 6.24 (3H,s; $OCH_3$), 6.36, 6.40 (2H, AB-q, $C_6H_5CH_2$). Chromatography of the filtrate on Kieselgel G gave p-methoxybenzaldehyde identified by comparision of its infrared spectrum with that of an authentic sample and by conversion into its 2,4-dinitrophenylhydrazone, m.p. 250° to 251°.

Part (500 mg) of the mixture of acids obtained above by filtration of the reaction mixture was suspended in tetrahydrofuran (50 ml) and esterified with a solution of diazomethane in ether. The solvents were removed and the residual white solid was dissolved in methylene chloride (40 ml). The resulting solution was washed with water (20 ml) and 3% sodium hydrogen carbonate solution (2 × 15 ml), dried and evaporated, and the residue was subjected to preparative layer chromatography on Kieselgel G with acetone-methylene chloride (1:1) as eluant. Elution of the less polar band gave methyl 3-bromomethyl-7β-phenylacetamidoceph-3-em-4-carboxylate (104 mg, 8.8 %), m.p. 193° to 194°, $[\alpha]_D +$ 59°, $\lambda_{max}$ 277.5 nm ($E_{1cm}^{1\%}$ 197), while elution of the more polar band gave methyl 3-methyl-7β-phenylacetamidoceph-3-em-4-carboxylate (170 mg, 19.7%), m.p. 210° to 215°, $[\alpha]_D +$ 185°, $\lambda_{max}$ 265 nm ($E_{1cm}^{1\%}$ 219).

EXAMPLE B8

Bromination of t-butyl 3-methyl-7β-phenylacetamidoceph-3-em-4-carboxylate, 1β-oxide to give t-butyl 3-bromomethyl-7β-phenylacetamidoceph-3-em-4-carboxylate, 1β-oxide A solution of t-butyl 3-methyl-7β-phenylacetamidoceph-3-em-4-carboxylate, 1β-oxide (389 mg, 1 mmole) and N-bromosuccinimide (287 mg, 1.5 equiv.) in benzene (50 ml) was heated under reflux for 1 hour in a stream of dry nitrogen while being illuminated by 8 × 40 watt fluorescent strip-lights. The reaction mixture was filtered from a trace of insoluble material and the benzene was evaporated. The residue was chromatographed on Kieselgel G (50 g) with acetone-methylene chloride (1:12) as eluant. The appropriate fractions as determined by TLC (acetone-methylene chloride; 1:8) were combined, evaporated and triturated with ether (ca. 2 ml) to give the title ester 1β-oxide as a white crystalline solid (134 mg, 29%), m.p. 158° to 160°, $[\alpha]_D +$ 52°, $\lambda_{max}$ 279 nm (ε 9,300), $\nu_{max}$ 3250 (NH), 1786 (azetidin-2-one), 1710 ($CO_2R$), 1673 and 1526 (CONH) and 1028 cm.$^{-1}$(S→O), τ 1.57 (1H,d, J 8.5 Hz; $NH$), 2.62 (5H,s; $C_6H_5$), 4.12 (1H,dd, J 8.5, 5 Hz; $C_7$-$H$), 5.01 (1H,d J 5 Hz; $C_6$-$H$), 5.32, 5.60 (2H, AB-q, J 12 Hz; $C_3$-$CH_2Br$), 6.18 (2H, broad s; $C_2H_2$), 6.34 (2H,s; $C_6H_5CH_2$), 8.42 (9H,s; $CO_2C(CH_3)_3$). (Found: C, 49.5; H, 4.8; Br, 16.0, 16.2; N, 5.5; S, 6.7. $C_{20}H_{23}BrN_2O_5S$ (483.4) requires C, 49.7; H, 4.8; Br, 16.5; N, 5.8; S, 6.6%).

EXAMPLE B9

Bromination of 2,2,2-trichloroethyl 3-methyl-7β-(2,2,2-trichloroethoxycarbonylamino)-ceph-3-em-4-carboxylate, 1β-oxide to give 2,2,2-trichloroethyl 3-bromomethyl-7β-(2,2,2-trichloroethoxycarbonylamino)ceph-3-em-4-carboxylate, 1β-oxide A solution of 2,2,2-trichloroethyl 3-methyl-7β-(2,2,2-trichloroethoxycarbonylamino) ceph-3-em-4-carboxylate, 1β-oxide (3.83 g, 7.13 mmole) and N-bromosuccinimide (1.78 g, 1.4 equiv.) in benzene (350 ml) was heated under reflux for 1 hour in a stream of dry nitrogen while being illuminated by 8 × 40 watt fluorescent strip-lights. The benzene was removed in vacuo and the residual orange foam was chromatographed on Kieselgel G (150 g) with acetone-methylene chloride (1:25) as eluant. The appropriate fractions as determined by TLC (acetone-methylene chloride; 1:15) were combined and evaporated to give a white solid (1.54 g.). Trituration with ether (ca. 20 ml) gave the title ester 1β-oxide (1.43 g, 33%), m.p. 202° to 204°, $[\alpha]_D −$ 4.9°, $\lambda_{max}$ 282.5 nm (ε 9,600), $\nu_{max}$ 3380 (NH), 1778 (azetidin-2-one), 1740 ($CO_2R$), 1730 and 1526 ($NHCO_2R$) and 1020 cm$^{-1}$ (S→O), τ 2.33 (1H,d, J 9 Hz; $NH$), 4.22 (1H,dd, J 9,5 Hz; $C_7$-$H$), 4.78, 4.95 (2H, AB-q, J 12 Hz; $CO_2CH_2CCl_3$), 4.92 (1H,d; J 5 Hz; $C_6$-$H$), 5.11 (2H,s; $NHCO_2CH_2CCl_3$), 5.35, 5.49 (2H, AB-q, J 10 Hz; $C_3$-$CH_2Br$), 5.92, 6.17 (2H, AB-q, J 18 Hz; $C_2$-$H_2$) (Found: C, 25.6; H, 2.0; N, 4.3; S, 5.2; total halogen 6.86 equiv./mole. $C_{13}H_{11}BrCl_6N_2O_6S$ (616) requires C, 25.3; H, 1.8; N, 4.55; S, 5.2%; total halogen 7 equiv./mole).

EXAMPLE B10

Bromination of t-butyl 3-methyl-7β-phenoxyacetamidoceph-3-em-4-carboxylate, 1β-oxide to give t-butyl 3-bromomethyl-7β-phenoxyacetamidoceph-3-em-4-carboxylate, 1β-oxide (i) By photochemically initiated bromination at −20° in the presence of water The solution of t-butyl 3-methyl-7β-phenoxyacetamidoceph-3-em-4-carboxylate, 1β-oxide in 1,2-dichloroethane (62.2 ml) from Preparation A 10(b) was diluted to 300 ml with dry 1,2-dichloroethane, and cooled to 5° and stirred in an atmosphere of nitrogen. 1,3-Dibromo-5,5-dimethylhydantoin (5.1 g, 17.85 mmole) and water (1 ml) were added and the stirred reaction mixture was cooled to −20° and illuminated for 1½ hours by a Philips 125-watt mercury arc using a Pyrex-filter. The brown solution was washed with water (2 × 100 ml), dried and evaporated to a foam which was triturated with acetone. The crystalline material was filtered off, washed with cold acetone-ether (1:1) and dried to give the title ester 1β-oxide (4.19 g, 35% from t-butyl 7β-amino-3-methylceph-3-em-4-carboxylate)m.p. 130° to 133° (dec.), $[\alpha]_D −26°$ $\lambda_{max}$ 275 nm (ε 11,300), inflexions at 264 nm (ε 8,700), 270 nm (ε 10,350) and 279.5 nm (ε 10,750), $\nu_{max}$ 3357 (NH) 1794 (azetidin-2-one), 1720 ($CO_2R$), 1694 and 1516 (CONH) and 1004 cm$^{-1}$(S→O), τ 1.86 (1H,d, J 10,5 Hz; $NH$), 2.5 to 3.2 (5H,m; $C_6H_5OCH_2$), 3.93 (1H,dd, J 10 Hz; $C_7$-$H$), 4.97 (1H,d, J 5 Hz; $C_6$-$H$), 5.32 (2H,s; $C_6H_5OCH_2$), 5.41, 5.57 (2H, AB-q, J = 9.5 Hz; C$_3$-C$\underline{H}_2$Br), 6.00, 6.26 (2H, AB-q, J 19 Hz; C$_2$-$\underline{H}_2$), 8.46 (9H,s; CO$_2$C(CH$_3$)$_3$), 7.91 (1H,s; ca.0.15 M acetone) (Found: C, 48.2, 48.4; H, 4.7, 4.8; Br, 15.7; N, 5.6, 5.7, S, 6.2. C$_{20}$H$_{23}$BrN$_2$O$_6$S (499.4) requires C, 48.1; H, 4.6; Br, 16.0; N, 5.6; S, 6.4%). The mother liquors were chromatographed on Kieselgel G (150 g) using acetone-methylene chloride (3:17) as eluant to give a second crop of the ester 1β-oxide (1.04 g. 9% as above), m.p. 128° to 132° (dec.) [α]$_D$ − 28°, λ$_{max}$ 275 nm (E$_{1cm}^{1\%}$ 218).

(ii) By photochemically initiated bromination at + 5° to −5° in the presence of aqueous sodium hydrogen carbonate A solution of t-butyl 3-methyl-7β-phenoxyacetamidoceph-3-em-4-carboxylate, 1β-oxide (5.0g, 11.9 mmole) in 1,2-dichloroethane (250 ml) was cooled to 0° and 1,3-dibromo-5,5-dimethylhydantoin (2.48 g, 8.65 mmole), sodium hydrogen carbonate (1.00 g, 11.9 mmole) and water (5 ml) were added. The stirred reaction mixture was illuminated by three 150-watt tungsten bulbs in an atmosphere of nitrogen for 75 minutes while the temperature was kept between +5° and −5°. The solution was washed with water (2 × 125 ml), combined with the dichloroethane back-wash (125 ml) of the combined aqueous washings, dried and evaporated to a yellow foam. Trituration with acetone-light petroleum (ca. 1:1) and refrigeration gave the title ester 1β-oxide as a light beige solid (4.49 g, 76%), m.p. 126° to 130°, [α]$_D$ −57°, λ$_{max}$ 274.5 nm (E$_{1cm}^{1\%}$ 197), τ 7.90 (3H,s; 0.5 M acetone).

EXAMPLE B11

Preparation of 2,2,2-trichloroethyl 3-bromomethyl-7β-phenoxyacetamidoceph-3-em-4-carboxylate 1β-oxide (the product of Example B5) from the starting material of Preparation A5 without isolation of intermediate 2,2,2-Trichloroethyl 3-methyl-7β-phenoxyacetamidoceph-3-em-4-carboxylate (10.00 g; 20.8 mmole) was oxidised as in Preparation A5 except that the temperature was kept at 0°, to give a crude product (10.4 g) which was dissolved in 1,2-dichloroethane (400 ml) and brominated as in Example B5 (i) to give the title compound (8.57 g, 71.8%) m.p. 156° to 157°; [α]$_D$ −43.6°, λ$_{max}$ 275 nm (E$_{1cm}^{1\%}$ 164), inflexions at 270 nm (E$_{1cm}^{1\%}$ 146) and 280 nm (E$_{1cm}^{1\%}$ 158).

EXAMPLE B12

2,2,2-Trichloroethyl 3-Bromomethyl-7β-(DL-2-bromophenylacetamido)ceph-3-em-4-carboxylate, 1β-Oxide N-Bromosuccinimide (1.43 g., 8.04 mmole) was added to a stirred solution of 2,2,2-trichloroethyl 7β-(DL-2-bromophenylacetamido)-3-methylceph-3-em-4-carboxylate (3.0 g., 5.36 mmole) in dry 1,2-dichloroethane (150 ml) at 0° in a dry nitrogen atmosphere. The reaction solution was irradiated with ultraviolet light (125 watt mercury arc with Pyrex filter) at 0° for 1¼ hrs. The solution was then washed with water (3 × 75 ml) and combined with the 1,2-dichloroethane backwash (75 ml) of the combined aqueous layers, dried and evaporated to give an oily solid. Trituration of this solid with methanol gave the title compound as a pale yellow solid (2.19 g.) m.p. 187°-189°; [α]$_D$ + 19.1°; λ$_{max}$ 278.5 nm (E$_{1cm}^{1\%}$ 150). Comparison of the product with that obtained in Example B2(X) by TLC and PMR techniques showed the two to be essentially the same except that the product obtained in this example was contaminated with 5 to 10% of the starting 3-methyl 1β-oxide analogue.

SECTION C

Conversion of 3-bromomethyl compounds to 3-iodomethyl and 3-chloromethyl analogues.

EXAMPLE C1 t-Butyl 7β-Formamido-3-iodomethylceph-3-em-4-carboxylate, 1β-Oxide

Potassium iodide (1.00 g, 6 mmole) was added to a solution of t-butyl 3-bromomethyl-7β-formamidoceph-3-em-4-carboxylate, 1β-oxide (0.79 g, 2 mmole) in acetone (30 ml), and the suspension was stirred for 2 hours in the absence of light. The acetone was removed in vacuo and the residue was distributed between chloroform and water (30 ml of each). The aqueous phase was re-extracted with chloroform (20 ml) and the combined chloroform phases were washed with water (20 ml), dried and evaporated to give title ester 1β-oxide (0.89 g, 100%), m.p. 110° to 130° (dec.), [α]$_D$ −13.6°, λ$_{max}$ 290 nm (ε 9,350), τ 1.63 (1H,d, J 9 Hz; N$\underline{H}$) 1.81 (1H,s; C$\underline{H}$O), 4.06 (1H,dd, J 9, 5 Hz; C$_7$-$\underline{H}$), 5.02 (1H,d, J 5 Hz; C$_6$-$\underline{H}$), 5.42, 5.65 (2H, AB-q, J 9 Hz; C$_3$-C$\underline{H}_2$I), 6.12 (2H,s; C$_2$-$\underline{H}_2$), 8.46 (9H,s; CO$_2$C(C$\underline{H}_3$)$_3$).

EXAMPLE C2

2,2,2-Trichloroethyl 7β-Formamido-3-iodomethylceph-3-em-4-carboxylate, 1β-Oxide

Sodium iodide (480 mg, 3.21 mmole) was added to a solution of 2,2,2-trichloroethyl 3-bromomethyl-7β-formamidoceph-3-em-4-carboxylate, 1β-oxide (500 mg, 1.07 mmole) in acetone (20 ml), and the mixture was stirred for 30 minutes in the absence of light, poured into water and extracted with methylene chloride (3 × 15 ml). The dried extract was evaporated and the residue was triturated with ethyl acetate to give the title ester 1β-oxide (116 mg, 21%), λ$_{max}$ 294 nm.

EXAMPLE C3

2,2,2-Trichloroethyl 3-Chloromethyl-7β-Formamidoceph-3-em-4-carboxylate 1β-Oxide Potassium chloride (1.60 g, 21.4 mmole) was added to a stirred solution of 2,2,2-trichloroethyl 3-bromomethyl-7β-formamidoceph-3-em-4-carboxylate, 1β-oxide (500 mg, 1.07 mmole) in N,N-dimethylformamide (50 ml). The mixture was stirred for 3 hours, diluted with methylene chloride (200 ml), washed with water (5 × 100 ml), combined with the methylene chloride back-wash (100 ml) of the aqueous washings, dried and evaporated to a yellow liquid. The liquid was redissolved in methylene chloride (100 ml) and this solution was washed with water (3 × 100 ml), combined with the methylene chloride back-wash (50 ml) of the aqueous washings, dried and evaporated to a pale yellow semisolid. Trituration with methanol gave a solid which was filtered off, washed with methanol-ether and ether, and dried to give the title ester 1β-oxide (315 mg, 69.5%), [α]$_D$ + 38°, λ$_{max}$ 276 nm (ε 8,650), τ 1.54 (1H,d, J 10 Hz; N$\underline{H}$), 1.81 (1H,s; C$\underline{H}$O), 3.95 (1H,dd, J 10,5 Hz; C$_7$-$\underline{H}$), 4.75, 4.93 (2H, AB-q, J 12 Hz; C$\underline{H}_2$CCl$_3$), 4.92 (1H,d, J 5 Hz; $C_6$-H̱), 5.26, 5.41 (2H, AB-q, J 12 Hz; $C_3$-CH̱$_2$Cl), 5.90, 6.21 (2H, AB-q, J 18 Hz; $C_2$-H̱$_2$).

EXAMPLE C4

2,2,2-Trichloroethyl 3-Iodomethyl-7β-(2-thienylacetamido)-ceph-3-em-4-carboxylate, 1β-Oxide A mixture of 2,2,2-trichloroethyl 3-bromomethyl- and 2,2,2-trichloroethyl 3-chloromethyl-7β-(2-thienylacetamido)-ceph-3-em-4-carboxylate, 1β-oxide (2.82 g., ca 5 mmole) was dissolved in acetone (70 ml). The solution was protected from the light and sodium iodide (2.25 g., 15 mmole) was added. The mixture was stirred for 1½ hours, poured into water (100 ml) and extracted with methylene chloride (3 × 50 ml). The combined methylene chloride extract was evaporated and the yellow residue was triturated with ethyl acetate (ca 15 ml) to give the title ester 1β-oxide (2.02 g., 66%), m.p. 185° (dec.), $[\alpha]_D$ −7.6°, $\lambda_{max}$ 227.5 nm ($\epsilon$ 12,650) and 294 nm ($\epsilon$ 9,300), $\tau$ 1.61 (1H,d, J 8.5 Hz; NH̱), 2.63, 3.05 (1H,2H,2m; 2-thienyl), 4.15 (1H,dd, J 8.5, 5 Hz; $C_7$-H̱), 4.76, 4.95 (2H, AB-q, J 12 Hz; CH̱$_2$CCl$_3$), 4.99 (1H,d, J 5 Hz; $C_6$-H̱), 5.40, 5.57 (2H, AB-q, J 9 Hz; $C_3$-CH̱$_2$I), 6.05 (2H, s; CH̱$_2$CONH), 6.05, 6.23 (2H, AB-q, J 16 Hz; $C_2$-H̱$_2$), (Found: C, 31.1; H, 2.3; N, 4.4; S, 10.8; total halogen 3.94 equiv./mole compound. $C_{16}H_{14}Cl_3IN_2S_2$ (611.7) requires C, 31.4; H, 2.3; N, 4.6; S, 10.5%; total halogen 4 equiv./mole compound).

SECTION D

Nucleophilic displacement and subsequent reaction using the products of Sections B and C

REACTIONS INVOLVING ALKANOATE NUCLEOPHILES

EXAMPLE D1

Methyl 3-acetoxymethyl-7β-phenylacetamidoceph-3-em-4-carboxylate, 1β-oxide

A suspension of methyl 3-bromomethyl-7β-phenylacetamidoceph-3-em-4-carboxylate, 1β-oxide (90 mg., 0.204 mmole) and potassium acetate (100 mg., 1.02 mmole; 5 eq.) in acetone (15 ml.) was heated to reflux in an atmosphere of nitrogen for 1.5 hours. After cooling, the reaction mixture was applied to two preparative thin-layer plates (20 × 20 cm., 2 mm. coating of Kieselgel HF$_{254+366}$) and the plates developed with methylene chloride - acetone (4:1) as eluent. The bands having an R$_F$ of 0.3 were removed, and extracted with methylene chloride - acetone (1:1), and the organic solution evaporated, to leave the title compound as a pale cream solid (58 mg., 67%), m.p. 210°–215° (dec.), $[\alpha]_D$ + 112°, $\lambda_{max}$ 268 nm (E$_{1cm}$$^{1\%}$ 187). This compound had IR and PMR spectra which very closely resembled those of the compound obtained either by oxidation of methyl 3-acetoxymethyl-7β-phenylacetamidoceph-3-em-4-carboxylate, or by esterification of 3-acetoxymethyl-7β-phenylacetamidoceph-3-em-4-carboxylic acid 1-oxide with diazomethane (Cocker et al., J. Chem. Soc. (c), 1966, 1142).

EXAMPLE D2

(i) 2,2,2-Trichloroethyl 3-acetoxymethyl-7β-phenylacetamidoceph-3-em-4-carboxylate, 1β-oxide A solution of 2,2,2-trichloroethyl 3-bromomethyl-7β-phenylacetamidoceph-3-em-4-carboxylate, 1β-oxide (1.12 g., 2 mmole) in dry N,N-dimethylformamide (60 ml.) was stirred at room temperature, and acetic acid (2 g.) and potassium acetate (1.01 g., 10 mmole) were added. After stirring for 1 hr., the reaction mixture was poured into water (500 ml.) and extracted with ethyl acetate (3 × 100 ml.). The combined ethyl acetate layers were washed successively with brine (75 ml.), 3%-sodium bicarbonate solution (75 ml.) and brine (3 × 75 ml.). The solution was then dried and stirred with charcoal (5 g.) for 1 hr., filtered through Kieselguhr and evaporated to leave the title compound (0.82 g., 77%) as a white solid, m.p. 106°–111°, $[\alpha]_D$ + 62° (CHCl$_3$), $\lambda_{max}$ 272 nm (E$_{1cm}$$^{1\%}$ 139).

A small sample of the product was recrystallised from ethyl acetate to give white crystals, m.p. 121°–5°, $[\alpha]_D$ + 92°, $\lambda_{max}$ 272 nm ($\epsilon$ 7,370), $\nu_{max}$ 1780 (azetidin-2-one), 1740 and 1220 (CH$_3$COO), 1740 (CO$_2$R), 1645 and 1524 (CONH), 1030 cm.$^{-1}$ (S→O), $\tau$ 7.96 (CH$_3$COO), 6.29 and 6.46 (AB-q,J 14 Hz; PhCH̱$_2$CO), 5.98 and 6.36 (AB-q,J 18 Hz; $C_2$-H̱$_2$), 5.00 and 4.81 (AB-q, J 12 Hz; CO$_2$CH̱$_2$CCl$_3$), 5.31 and 4.86 (AB-q, J 13 Hz; CH̱$_2$OCOCH$_3$), 5.04 (d, J 4.5 Hz; $C_6$-H̱), 4.11 (dd, J 4.5 and 8.5 Hz; $C_7$-H̱), 2.71 (C$_6$H$_5$) and 1.63 (d, J 8.5 Hz; NH̱) (Found: C, 45.0; H, 3.6; Cl, 19.7; N, 4.4; S, 5.8. $C_{20}H_{19}Cl_3N_2O_7S$ requires: C, 44.7; H, 3.6; Cl, 19.8; N, 5.2; S, 6.0%).

(ii) Sodium 3-acetoxymethyl-7β-phenylacetamidoceph-3-em-4-carboxylate

Potassium iodide (6.0 g.), followed by acetyl chloride (freshly distilled, 1.0 ml.), was added to a solution of 2,2,2-trichloroethyl 3-acetoxymethyl-7β-phenylacetamidoceph-3-em-4-carboxylate, 1β-oxide (1.075 g., 2 mmole) in glacial acetic acid (50 ml.). Iodine was immediately liberated. The reaction mixture was stirred for 6 mins. at room temperature before the addition of N-sodium thiosulphate solution (10 ml.). The solution was evaporated in vacuo and the residue partitioned between water and ethyl acetate (50 ml. each). The layers were separated and the aqueous portion extracted with further ethyl acetate (25 ml.). The combined extracts were washed with 3%-aqueous sodium hydrogen carbonate, then saturated brine (50 ml. each), dried and evaporated to a pale yellow foam (987 mg.). Thin-layer chromatographic analysis [coated silica gel, with methylene chloride-acetone (9:1)] revealed the presence of starting 1β-oxide (R$_F$ 0.3) and a new less polar component (R$_F$ 0.7). The foam was dissolved in acetone and applied to two preparative thin-layer plates (Kieselgel HF$_{254+366}$; 20 × 20 cm. × 2 mm.). The plates were eluted with methylne chloride-acetone (9:1) and the appropriate bands extracted with the same solvent mixture, and evaporated. The more polar band gave a pale yellow oil (121 mg.) which was triturated with ethyl acetate (2 ml.) to give the starting sulphoxide ester (50 mg., 4.65%), m.p. 116°–122°, $[\alpha]_D$ + 89°, $\lambda_{max}$ 272 nm (E$_{1cm}$$^{1\%}$ 142).

The less polar band provided a white foam (642 mg.), $\lambda_{max}$ 262 nm (E$_{1cm}$$^{1\%}$ 124). The bulk of this material (628 mg.) was dissolved in anhydrous formic acid-methylene chloride (4:1, 15 ml.) and the solution cooled to 0°–5° with stirring. Zinc dust (1.2 g., 18.36 gm. equiv.) (freshly activated by washing with 2N-hydrochloric acid then anhydrous formic acid) was added portion-wise over 2–3 min. The mixture was stirred at 0°–5° for 15 hr., then filtered through Celite, the filter pad being washed with anhydrous formic acid - methylene chloride (4:1, 5 ml.). The filtrate was evaporated in vacuo leaving a yellow oil to which 3% aqueous sodium hydrogen carbonate (50 ml.) and ethyl acetate (50 ml.) were added. A small amount of insoluble material was removed by filtration and the layers were separated. The organic layer was extracted with further 3% sodium hydrogen carbonate (30 ml.) and then the combined aqueous portions were layered with ethyl acetate (50 ml.) and acidified to pH 1.0 with 2N-hydrochloric acid. After an additional extraction with ethyl acetate (30 ml.), the combined extracts were washed with saturated brine (30 ml.), dried, and evaporated to a colourless oil (313 mg.). This was dissolved in ethyl acetate - n-butanol (4:1) (15 ml.) and treated with a 10% solution of sodium 2-ethylhexanoate in n-butanol (1.95 ml.). The gelatinous precipitate was set aside at 0° for 30 min. and then collected, being successively washed with ethyl acetate - n-butanol (1:1) (5 ml.), ethyl acetate (5 ml.) and ether (25 ml.). The resulting white solid was dried at 1 mm. to give the title compound (180 mg., 22.4%), $[\alpha]_D$ + 141.5° ($H_2O$); $\lambda_{max.}$ (0.1M phosphate buffer at pH 6.0) 259 nm ($\epsilon$ 8,300); $\nu_{max.}$ 3285 (NH), 1750 (azetidin-2-one), 1730 and 1250 ($OCOCH_3$) 1659 and 1630 (CONH) and 1626 cm.$^{-1}$ ($CO_2^-$); $\tau$ ($D_2O$) 2.67 (5H,s; $C_6H_5$), 4.42 (1H,d, J 4.5 Hz; $C_7$-H), 4.98 (1H,d, J 4.5 Hz; $C_6$-H), 5.16 and 5.37 (2H, AB-q, J 12 Hz; $CH_2OCOCH_3$) 6.35 (2H,s; $C_6H_5CH_2$), 6.42 and 6.73 (2H, AB-q, J 18 Hz; $C_2$-$CH_2$) and 7.94 (3H,s; $OCOCH_3$).

The above material was compared both chromatographically and by microbiological assay with a sample of the title sodium salt, $[\alpha]_D$ + 140° ($H_2O$), prepared from cephalosporin C via phenylacetylation of 7β-aminocephalosporanic acid. The two specimens had identical $R_F$ values in a descending system on equilibrated Whatman No. 1 paper buffered at pH 5, eluting with the upper phase from ethyl acetate - n-butanol - 0.1M sodium acetate buffer at pH 5 (8:1:8), the lower phase being in the tank.

The two specimens were also compared microbiologically by in vitro tube dilution assay in parallel. The minimum inhibitory concentration in μg./ml. is given for each organism, with the value obtained for the authentic sample given in brackets:

Staph.aureus 604, 0.8 (0.8); Staph.aureus 663, 0.8 (0.8); Staph.aureus 3452, 1 (<0.5); Staph.aureus 11127, <0.5 (<0.5); E.coli 573, 31 (31); E. coli 9001, 31 (31); S. typhimurium 804, 16 (31); Pr. mirabilis 2, 31 (8); Pr.mirabilis 431, 8 (8); Ps. pyocyanea 150, >250 (>250); C. albicans C 316, >250 (>250); Strep.faecalis 850, 16 (16); Pr.morgani NCTC 235, >250 (250); Klebsiella 415, 62 (62).

EXAMPLE D3

(i) 2,2,2-Trichloroethyl 3-Acetoxymethyl-7β-formamidoceph-3-em-4-carboxylate, 1β-Oxide Potassium acetate (245 mg., 2.5 mmole) was added to a solution of 2,2,2-trichloroethyl 3-bromomethyl-7β-formamidoceph-3-em-4-carboxylate, 1β-oxide (234 mg, 0.5 mmole) in N,N-dimethylformamide (10 ml) and glacial acetic acid (0.5 ml). The dark solution was stirred for 1 hour and diluted with water (50 ml) and ethyl acetate (25 ml.). The aqueous phase was extracted with ethyl acetate (3 × 25 ml), and the combined ethyl acetate extract was washed with water (2 × 25 ml) and then stirred with charcoal and anhydrous magnesium sulphate for 30 minutes. The mixture was filtered through Celite and the filtrate was evaporated to a pale yellow solid (202 mg). Trituration with a mixture of acetone (ca. 5 ml) and ether (ca. 15 ml) gave the title ester 1β-oxide (113 mg, 50.5%), m.p. 173° to 174° (dec), $[\alpha]_D$ + 87°, $\lambda_{max.}$ 271.5 nm ($\epsilon$ 8,650), $\nu_{max.}$ 3390 (NH), 1765 (azetidin-2-one), 1740 and 1730 ($CO_2R$), 1690 and 1500 (CONH) and 1040 cm$^{-1}$ (S→O), $\tau$ 1.62 (1H,d, J 9 Hz; NH), 1.85 (1H,s; CHO), 4.00 (1H,dd, J 9,5 Hz; $C_7$-H), 4.82, 5.01 (2H, AB-q, J 12 Hz; $CH_2CCl_3$), 4.87, 5.29 (2H, AB-q, J 13 Hz; $C_3$-$CH_2OCOCH_3$), 4.99 (1H,d, J 5 Hz; $C_6$-H), 5.93, 6.33 (2H, AB-q, J 18 Hz; $C_2$-$H_2$), 7.94 (3H,s; $OCOCH_3$) (Found: C, 35.3; H, 3.0; Cl, 23.3; N, 6.0; S, 7.3. $C_{13}H_{13}Cl_3N_2O_7S$ (447.7) requires C, 34.9; H, 2.9; Cl, 23.75; N, 6.3; S, 7.2%).

(ii) 2,2,2-Trichloroethyl, 3-Acetoxymethyl-7β-aminoceph-3-em-4-carboxylate, 1β-Oxide Hydrochloride Phosphorus oxychloride (0.92 ml, 10 mmole) was added to a stirred suspension of 2,2,2-trichloroethyl 3-acetoxymethyl-7β-formamidoceph-3-em-4-carboxylate, 1β-oxide (1.12 g, 2.5 mmole) in dry methanol (20 ml) when the temperature rose to 30°. The reaction mixture was stirred for 40 minutes, diluted with ether (ca. 20 ml) and refrigerated for 30 minutes to give a ca. 1:1 mixture of the title hydrochloride and 7β-amino-3-hydroxymethylceph-3-em-4-carboxylic acid γ-lactone, 1β-oxide, hydrochloride (0.81 g, 89%), $\lambda_{max.}$ (MeOH) 266 nm ($E_{1cm}^{1\%}$ 180), $\nu_{max}$ ca. 2550 ($NH_3$+), broad 1780 (azetidin-2-one and γ-lactone), 1728 ($CO_2R$) and 1026 cm$^{-1}$ (S→O) $\tau$ 4.80, 4.98 (ca. 1H,AB-q, J 12 Hz; $CO_2CH_2CCl_3$), 4.88, 5.27 (ca. 1H, AB-q, J 14 Hz; $C_3$-$CH_2OCOCH_3$), 7.94 (ca. 1.5 H,s; $OCOCH_3$) and 4.91 (ca. 1H,s; $C_3$-$CH_2O$.$CO$-$C_4$).

EXAMPLE D4

(a) 2,2,2-Trichloroethyl 3-Bromomethyl-7β-(2-thienylacetamido) ceph-3-em-4-carboxylate, 1β-Oxide A solution of ethylene oxide (40 ml) in dry methylene chloride (30 ml) followed by thienylacetyl chloride (1.2 ml, 1.05 equiv.) was added to a suspension of 2,2,2-trichloroethyl 7β-amino-3-bromomethylceph-3-em-4-carboxylate, 1β-oxide, hydrobromide (4.94 g, 9.5 mmole) in dry methylene chloride (40 ml). The solid went into solution after 2 minutes. The mixture was stirred for 4 minutes, washed with 2.4% sodium carbonate solution (50 ml), combined with the methylene chloride backwash (25 ml) of the alkaline washings, washed with water and saturated aqueous sodium bromide solution (50 ml of each), dried and evaporated. The residue was triturated with light petroleum, b.p. 40°–60°, to give the title ester 1β-oxide (4.94 g, 92%), $[\alpha]_D$ + 23°, $\lambda_{max}$ 232 nm ($\epsilon$11,350) and 283 nm ($\epsilon$9,100).

(b) 2,2,2-Trichloroethyl 3-Acetoxymethyl-7β-(2-thienylacetamido)ceph-3-em-4-carboxylate, 1β-Oxide (i) Glacial acetic acid (4.72 ml) and potassium acetate (2.32 g, 23.6 mmole) were added to a solution of 2,2,2-trichloroethyl 3-bromomethyl-7β-(2-thienylacetamido)ceph-3em-4-carboxylate, 1β-oxide (2.66 g, 4.72 mmole) in N,N-dimethylformamide (100 ml). The reaction mixture was stirred at 22° for 3 hours, and diluted with ethyl acetate and water (200 ml of each). The aqueous phase was extracted with ethyl acetate (3 × 100 ml) and the combind ethyl acetate extract was washed with water (2 × 50 ml), stirred with charcoal and anhydrous magnesium sulphate for 1 hour, filtered through Celite and evaporated. The oily residue was triturated with light petroleum, b.p. 40°–60°, to give the title ester 1β-oxide (1.71 g, 68%), m.p. 130° to 132° (dec), $[\alpha]_D$ +85.5°, $\lambda_{max}$ 236 nm ($\epsilon$11,300) and 269 nm ($\epsilon$ 7,600), $\lambda_{max}$ 3330 (NH), 1800 (azetidin-2-one), 1735 and 1725 (CO$_2$), 1660 and 1530 (CONH) and 1055 cm$^{-1}$ (S→O), $\tau$ 1.60 (1H,d, J 9 Hz; NH), 2.64, 3.05 (1H,2H, 2m; 2-thienyl), 4.10 (1H,dd. J 9,5 Hz; C$_7$-H), 4.81,5.00 (2H, AB-q, J 12 Hz; CH$_2$CCl$_3$), 4.87, 5.31 (2H, AB-q, J 14 Hz; C$_3$-CH$_2$OCOCH$_3$), 5.03 (1H,d, J 5 Hz; C$_6$-H), 5.97, 6.36 (2H, AB-q, J 18 Hz; C$_2$-H$_2$), 6.05, 6.23 (2H, AB-q, J 16 Hz; CH$_2$CONH), 7.97 (3H,s;OCOCH$_3$) (Found: C, 39.6; H, 3.2; Cl, 19.5; N, 4.9; S, 11.9 C$_{18}$H$_{17}$Cl$_3$N$_2$O$_7$S$_2$ (533.8) requires C, 39.8; H, 3.2; Cl, 19.6; N, 5.2; S, 11.8%).

(ii) In an experiment similar to (i), but using 2,2,2-trichloroethyl 3-iodomethyl-7β-(2-thienylacetamido)-ceph-3-em-4-carboxylate, 1β-oxide (1.53 g, 2.5 mmole) as starting material, the title ester 1β-oxide was obtained as a buff solid (0.66 g, 50%), m.p. 129° to 130°, $[\alpha]_D$ + 86°, $\lambda_{max.}$ 237 nm ($\epsilon$ 10,950) and 272 nm ($\epsilon$ 7,900).

(c) 2,2,2-Trichloroethyl 3-Acetoxymethyl-7β-(2-thienylacetamido) ceph-3-em-4-carboxylate Potassium iodide (3.0 g) and acetyl chloride (0.5 ml) were added to a solution of 2,2,2-trichloroethyl 3-acetoxymethyl-7β-(2-thienylacetamido)ceph-3-em-4-carboxylate, 1β-oxide (534 mg, 1 mmole) in glacial acetic acid (25 ml). Iodine was liberated immediately. The reaction mixture was stirred for 10 minutes at ca. 20°, and a slution of sodium metabisulphite (0.40 g) in water (10 ml) was added. The solvents were removed in vacuo and the residue was distributed between ethyl acetate and water (25 ml of each). The aqueous phase was extracted with ethyl acetate (12 ml) and the combined organic phases were washed with 3% sodium hydrogen carbonate solution (2 × 25 ml) and saturated brine (25 ml), dried and evaporated to a yellow gum. This gum was crystallised from aqueous I.M.S. to give the title ester as white cyrstals (336 mg. 65%), m.p. 116° to 117°, $[\alpha]_D$ + 56°, $\lambda_{max.}$ 237 nm ($\epsilon$ 10,900) and 264 nm ($\epsilon$ 6,750), $\nu_{max}$ 3330 (NH), 1765 (azetidin-2-one), 1720 (CO$_2$R) and 1680 and 1535 cm$^{-1}$(CONH), $\tau$ 1.87 (1H,d, J 8 Hz; NH), 2.62, 3.04 (1H,2H,2m; 2-thienyl), 4.23 (1H,dd, J 8,5Hz; C$_7$-H), 4.80 (1H, d, J 5 Hz; C$_6$-H), 4.83, 5.05 (2H, AB-q,J 12 Hz; CH$_2$CCl$_3$), 5.01, 5,24 (2H, AB-q, J 13 Hz; C$_3$-CH$_2$OCOCH$_3$), 6.23 (2H,s; CH$_2$CONH), 6.24, 6.46 (2H, AB-q, J 18 Hz; C$_2$-H$_2$), 7.96 (3H,s; OCOCH$_3$) (Found: C, 40.4,40.4; H, 3.2, 3.3; Cl, 19.95; N, 4.9,5.1; S, 12.2. C$_{18}$H$_{17}$Cl$_3$N$_2$O$_6$S$_2$ (517.8) requires C, 41.0; H, 3.2; Cl, 20.15; N, 5.3; S, 12.15%).

(d) Sodium 3-Acetoxymethyl-7β-(2-thienylacetamido)ceph-3-em-4carboxylate

A solution of 2,2,2-trichlorcethyl 3-acetoxymethyl-7β-(2-thienylacetamido)ceph-3-em-4-carboxylate (2.71 g, 5.2 mmole) in anhydrous formic acid (50 ml) was added to a suspension of zinc dust (2.7 g) and zinc chloride (60 mg) in anhydrous formic acid (50 ml) cooled in an ice-bath. The cooling bath was withdrawn, and the reaction mixture was stirred at ca. 25° for 5 hours, refrigerated overnight and filtered through a pad of Celite. The filter bed was washed with formic acid, and the filtrate and washings were passed through a column of Deacidite FF ion-exchange resin (Cl$^-$ form; ca. 25 ml), eluting with formic acid (98–100%). The eluate (180 ml) was evaporated in vacuo and the residue was distributed between ethyl acetate (100 ml) and 3% aqueous sodium hydrogen carbonate solution (400 ml), some solid remaining out of solution. The ethylacetate phase was re-extracted with 3% sodium hydrogen carbonate solution (50 ml), and the combined alkaline extracts were acidified to pH 1 with 2N-hydrochloric acid in the presence of ethyl acetate (50 ml). The aqueous phase was re-extracted with ethyl acetate (50 ml), and the combined ethyl acetate extract was washed with brine (25 ml), dried and evaporated. The residual foam was dissolved in acetone (10 ml) and a 10% solution of sodium 2-ethylhexanoate in acetone was added dropwise until precipitation was complete. After overnight refrigeration, the solid was collected, washed with acetone and dried to give the title sodium salt (0.60 g, 27%), $[\alpha]_D$ +106°, $\lambda_{max.}$ (pH 6 0.1 M phosphate) 237 nm (E$_{1cm}^{1\%}$ 316), inflexion at 260 nm (E$_{1cm}^{1\%}$ 178), with IR and PMR spectra similar to material obtained by thienylacetylation of 7β-aminocephalosporanic acid derived from cephalosporin C.

EXAMPLE D5

Preparation of 2,2,2-trichloroethyl 3-acetoxymethyl-7β-formamidoceph-3-em-4-carboxylate fromthe product of Example B3 without isolating the product of the nucleophilic displacement Glacial acetic acid (5 ml) and N,N-dimethylformamide (125 ml) were added to a mixture of 2,2,2-trichloroethyl 3-bromomethyl-7β-formamidoceph-3-em-4-carboxylate, 1β-oxide (17.715 g, 25 mmole) and potassium acetate (12.25 g, ca. 125 mmole). The resulting mixture which darkened rapidly was stirred at ca. 20° for 1 hour when potassium iodide (30 g, 180 mmole) and acetyl chloride (13 ml, 0.183 mole) were added with stirring. The temperature of the reaction mixture rose to ca. 50°. After stirring for 15 minutes, M-sodium thiosulphate solution (30 ml) was added and the reaction mixture was diluted with methylene chloride (500 ml) and water (1 l) and shaken vigorously. The aqueous layer was re-extracted with methylene chloride (2 × 100 ml) and the combined organic phases were washed with water (300 ml) containing M-sodium thiosulphate solution (10 ml), and then water (3 × 300 ml). Each of these washings was acidic (pH 3) and contained suspended brown flocculent material. The dark brown methylene chloride solution was dried and filtered through a column of Kieselgel G (30 g) when much of the colour was retained. The eluate was evaporated and the residue was dissolved in ethyl acetate (100 ml), washed with water (2 × 200 ml) and evaporated to give the title ester as a brown foam (6.9 g, 64%), $[\alpha]_D$ + 59° (CHCl$_3$), $\lambda_{max}$ 265 nm ($\epsilon$ 6,800), $\nu_{max}$ (CHBr$_3$) 3430 (NH), 1790 (azetidin-2-one), 1745 (CO$_2$R) and 1700 and 1510 cm$^{-1}$ (CONH), $\tau$ (CDCl$_3$) 1.76 (1H,s; CHO), 3.29 (1H,d, J 9.5 Hz; NH), 4.09 (1H,dd, J 9.5,5 Hz; C$_7$-H), 4.97 (1H,d, J 5 Hz; C$_6$-H), 4.86, 5.16 (2H, Ab-q,J 14 Hz; C$_3$-CH$_2$OCOCH$_3$), 4.99, 5.25 (2H, AB-q, J 12 Hz; CH$_2$CCl$_3$), 6.36, 6.60 (2H, Ab-q, J 18 Hz; C$_2$-H$_2$), 7.91 (3H,s; OCOCH$_3$).

EXAMPLE D6 t-Butyl 3-Acetoxymethyl-7β-formamidoceph-3-em-4-carboxylate, 1β-Oxide

Potassium acetate (0.20 g, ca. 2 mmole) was added to a solution of t-butyl 3-bromomethyl-7β-formamidoceph-3-em-4-carboxylate, 1β-oxide (152 mg, 0.385 mmole) in N,N-dimethylformamide (6 ml) and glacial acetic acid (0.25 ml). The reaction mixture was stirred at ca. 20° for 1½ hours and diluted with water and methylene chloride. The aqueous phase was extracted (×2) with methylene chloride and the combined organic phases were washed (×3) with water, dried and evaporated. Trituration with a mixture of acetone and ether gave a gel, part of which was filtered off to give the title ester 1β-oxide as a cream solid (29 mg), $\lambda_{max}$ 267 nm ($\epsilon$ 8,900) $\tau$ 1.66 (1H,d, J 10 Hz; N$\underline{H}$), 1.84 (1H,s; C$\underline{H}$O), 4.05 (1H,dd, J 10, 5Hz; C$_7$-$\underline{H}$), 4.86, 5.43 (2H, AB-q, J 13 Hz; C$_3$-C$\underline{H}_2$OCOCH$_3$), 5.08 (1H,d, J 5 Hz; C$_6$-$\underline{H}$), 6.05, 6.42 (2H, AB-q, J 18 Hz; C$_2$-$\underline{H}_2$), 7.94 (3H,s; OCOC$\underline{H}_3$), 8.46 (9H,s; CO$_2$C(C$\underline{H}_3$)$_3$).

the filtrate from above was combined with the unfiltered portion of the gel and evaporated. Trifluoroacetic acid (2ml) was added; the resulting solution was kept for 5 minutes and re-evaporated. The residual pale yellow gum was treaed with acetone (ca. 4 ml) to give 3-acetoxymethyl-7β-formamidoceph-3-em-4-carboxylic acid, 1β-oxide as a white solid (52 mg), $\lambda_{max}$ (pH 6 0.1M phosphate) 257.5 nm ($\epsilon$ 10,200), $\nu_{max}$ 3595 and 3510 (OH), 3280 (bonded NH), ca. 2600 (bonded OH), 1780 (azetidin-2-one), 1740 (monomeric CO$_2$H), 1725 and 1240 (OAc), 1710 (dimeric CO$_2$H), 1660 and 1520 (CONH) and 990 cm$^{-1}$ (s→0), $\tau$ 1.66 (1H,d, J 9 Hz; N$\underline{H}$). 1.85 (1H,s; C$\underline{H}$O), 4.06 (1H,dd, J 9, 5.5 Hz; C$_6$-$\underline{H}$), 4.81, 5.39 (2H, AB-q, J 13 Hz; C$_3$-C$\underline{H}_2$OCOCH$_3$), 5.08 (1H,d, J 4.5 Hz; C$_6$-$\underline{H}$), 6.06, 6.41 (2H, AB-q, J 18 Hz; C$_2$-$\underline{H}_2$), 7.94 (3H,s; OCOC$\underline{H}_3$).

REACTIONS INVOLVING NITROGEN NUCLEOPHILES

EXAMPLE D7

(i) 2,2,2-Trichloroethyl N-(7β-phenylacetamidoceph-3-em-3-ylmethyl)-pyridinium bromide 4-carboxylate, 1β-oxide 2,2,2-Trichloroethyl 3-bromomethyl-7β-phenylacetamidoceph-3-em-4-carboxylate, 1β-oxide (1.50 g., 2.68 mmole) was dissolved in dry (distilled from potassium hydroxide pellets) pyridine (50 ml.). Almost immediately a fine solid separated from the green solution and after 15 min. The suspension was diluted with benzene - ether (1:1; 50 ml.) and stirred for a further 15 min. The pale-green solid was collected and dissolved in methylene chloride (75 ml.), and fltered, and ether (50 ml.) was added. The resulting precipitate was collected and dried to give the sulphoxide ester as a hygroscopic white powder (1.58 g., 92%), m.p. 154°-156°, [α]$_D$ + 43.0°, $\lambda_{max}$ 263 nm ($\epsilon$ 9,900), 275 nm (inflexion; $\epsilon$ 7,660), $\nu_{max}$ (CHBr$_3$) 3400 (NH), 1805 (azetidin-2-one), 1740 (CO$_2$CH$_2$CCl$_3$), 1685 and 1505 (CONH) and 1035 cm.$^{-1}$ (S→0), $\tau$ multiplets centred at 1.00 (2H), 1.31 (1H), and 1.77 (2H) (pyridinium o-, p- and m-protons respectively), 1.49 (1H,d, J 9 Hz; N$\underline{H}$), 2.70 (5H,s; C$_6$$\underline{H}_5$), 4.00 (1H,dd, J 5 and 9 Hz; C$_7$-$\underline{H}$), 4.29 (2H, broad s -C$\underline{H}_2$N$^+$), 4.78 and 5.00 (2H, AB-q,J 13 Hz; C$\underline{H}_2$CCl$_3$), 4.90 (1H,d, J 5 Hz; C$_6$-$\underline{H}$), 5.90 and 6.30 (2H, AB-q,J 18 Hz; C$_2$-$\underline{H}_2$) and 6.30 and 6.45 (2H, AB-q,J 11 Hz; C$_6$H$_5$C$\underline{H}_2$). Electrophoresis at pH1.9 showed a single spot migrating towards the cathode, R$_c$ 2.6, which gave a mauve colour with potassium iodoplatinate spray reagent.

Analytical data were obtained on a similarly prepard sample from a preliminary experiment, m.p. 153°-154°, $\lambda_{max}$ 264 nm (68 9,950), 275 nm (inflexion; $\epsilon$ 7,780) (Found: C, 41.5; H, 3,3; N, 6.2; S, 4.9; total halogen content, 3.8 equiv./mole of compound. C$_{23}$H$_{21}$BrCl$_3$N$_3$O$_5$S (637.8) requires: C, 43.3; H, 3.3; N, 5.6; S, 5.0%; total halogen content, 4.0 equiv. per 1 mole of compound).

(ii) Reduction of 2,2,2-trichloroethyl N-[7β-phenylacetamido-ceph-3-em-3-ylmethyl] pyridinium bromide 4-carboxylate 1β-oxide.

(a) With phosphorus trichloride.

Phosphorus trichloride (0.88 ml., 10 mmole) was added to a solution of the title sulphoxide ester (1.28 g., 2.0 mmole) in dry methylene chloride (50 ml.). After stirring at ca. 25° for 4 hr. the cloudy solution was evaporated in vacuo and the sticky yellow residue was triturated with acetone to provide a white crystalline solid. This was collected using additional cold acetone and dried to give 2,2,2-trichloroethyl N-[7β-phenylacetamidoceph-3-em-3-ylmethyl]pyridinium bromide 4-carboxylate as white prisms (525 mg., 42%), m.p. 142°-146°. [α]$_D$ − 3.5°, $\lambda_{max}$ 261 nm ($\epsilon$ 10,510), $\nu_{max}$ 1790 (azetidin-2-one), 1742 (CO$_2$CH$_2$CCl$_3$), 1692 and 1550 cm.$^{-1}$ (CONH), $\tau$ 0.83 (1H,d, J 9 Hz; CON$\underline{H}$), multiplets centred at 0.90 (2H),1.32 (1H) and 1.76 (2H) (pyridinium o-, p- and m-protons respectively), 2.73 (5H,s; C$_6$$\underline{H}_5$), 4.18 (1H,dd, J 5 and 9 Hz; C$_7$-$\underline{H}$), 4.25 (2H,s; C$\underline{H}_2$N$^+$), 4.78 (1H,d, J 5 Hz; C$_6$-$\underline{H}$), 4.80 and 5.00 (2H, AB-q,J 12 Hz; C$\underline{H}_2$CCl$_3$), 6.39 (2H,s; CH$_2$S) and 6.45 (2H,s; C$_6$H$_5$C$\underline{H}_2$). Electrophoresis at pH 1.9 showed a single spot migrating towards the cathode, R$_c$ 3.3, which gave a mauve colour with potassium iodoplatinate spray reagent. The filtrate upon dilution with an equal volume of ether provided an additional quantity o less pure ester (500 mg., 40%) as a pale yellow solid, m.p. 128°-130°, [α]$_D$ ±0°, $\lambda_{max}$ 261 nm ($\epsilon$ 9,200).

Recrystallisation of a portion of the first crop material from acetone - water (1:1) gave white prisms, m.p. 156°-159°, [α]$_D$ − 1.5°, $\lambda_{max}$ 258.5 nm ($\epsilon$ 10,260).

(b) With potassium iodide — acetyl chloride.

Potassium iodide (3.0 g.), followed by acetyl chloride (freshly distilled, 0.5 ml.), was added to a solution of the title sulphoxide (638 mg., 1 mmole) in glacial acetic acid (25 ml.). Iodine was immediately liberated. The reaction mixture was stirred for 5 min., then N-sodium thiosulphate solution (5 ml.) was added. The pale-yellow solution was diluted with water (100 ml.) and extracted with ether (2 × 50 ml.), and then ethyl acetate (2 × 50 ml.). The combined ethyl acetate extracts were washed with saturated brine (50 ml.), dried and evaporated to a buff foam (315 mg.) which was treated with ether (ca. 5 ml.) to give 2,2,2-trichloroethyl N-(7β-phenylacetamidoceph-3-em-3-ylmethyl) pyridinium bromide 4-carboxylate as an off-white solid (240 mg., 39%), m.p. 130°-132°, [α]$_D$ − 3.0° $\lambda_{max}$ 258 nm ($\epsilon$ 10,080), similar to the material described in (a).

Evaporation of thedried extracts gave a pale yellow solid which upon treatment with ether (ca. 5 ml.) provided impure startng sulphoxide ester as a pale yellow solid (140 mg., 22%), m.p. 121°–124°, $\lambda_{max.}$ 262 nm ($\epsilon$ 10,640), 275 nm (inflexion; $\epsilon$ 9,200).

(iii)
N-(7β-Phenylacetamidoceph-3-em-3-ylmethyl)-pyridinium-4-carboxylate hydronitrate.

2,2,2-Trichloroethyl N-(7β-phenylacetamidoceph-3-em-3-ylmethyl) pyridinium bromide 4-carboxylate (1.00 g., 1.61 mmole was dissolved in anhydrous formic acid - methylene chloride (2:1, 24 ml.) and the solution cooled to 0°–5° with stirring. Zinc dust (3.0 g., 28.5 g. equiv.) [freshly activated by washing with 2N-hydrochloric acid, then formic acid (10 ml. each)]was added, and the mixture stirred at 0°–5° for 24 hr. The mixture was filtered, the filter pad being washed with anhydrous formic acid - methylene chloride (2:1, 6 ml.). The filtrate and washings were concentrated in vacuo to remove the methylene chloride and the residual solution made up to 10 ml. with formic acid. Water (2.5 ml.) was added and the solution passed through an ion-exchange column consisting of De-acidite FF (Cl$^-$) over De-acidite FF (OAc$^-$) (10 ml. of each resin). The column was washed with formic acid — water (4:1, 100 ml.).
The eluate was evaporated in vacuo and the residue dissolved in glacial acetic acid (20 ml.) and re-evaporated. The residual oil was dissolved in water - acetic acid (4:1, 25 ml.) and extracted with ether (2 × 25 ml.). The ether extracts were each back-extracted with water - acetic acid (4:1, 5 ml.). The combined aqueous portions were evaporated to a foam (690 mg.) which was dissolved in water (10 ml.) - acetic acid (1.6 ml.). The solution was filtered and taken from pH 4.8 to pH 0.9 with concentrated nitric acid, then refrigerated. Scratching the walls of the vessel induced crystallisation of a white solid which was collected, washed with acetone (ca. 3 ml.) and dried to give the hydronitrate as white prisms (219 mg., 28%), m.p. 144°–148° (no depression on admixture with authentic material; see below), $[\alpha]_D$ − 11.2°, $\lambda_{max.}$ (0.1M-phosphate buffer at pH 6.0) 259 nm ($\epsilon$ 13,050), $\nu_{max.}$ 3310 (NH), 1770 (azetidin-2-one), 1690 (CO-OH), 1690 and 1540 (CONH) and 1380 cm.$^{-1}$ (NO$_3{}^-$), $\tau$ 0.82 (1H,d, J 9 Hz; —CONH), multiplets centred at 0.84 (2H), 1.21 (1H) and 1.72 (2H) (pyridinium o-, p- and m-protons respectively), 2.71 (5H,s; C$_6$H$_5$), 4.18 (1H,dd, J 5 and 9 Hz; C$_7$-H), 4.38 (2H,s; CH$_2$N$^+$), 4.80 (1H,d, J 5 Hz; C$_6$-H) and ca. 4.90 (broad envelope; -CO$_2$H and H$_2$O).

The above material showed a single spot on electrophoresis at pH 1.9 which migrated toward the cathode exactly as did a sample of the hydronitrate prepared by adding concentrated nitric acid to a 1% solution of pyridine in water containing N-(7β-phenylacetamidoceph-3-em-3-ylmethyl) pyridinium 4-carboxylate (obtained from sodium 7β-phenylacetamidocephalosporanate, with cephalosporin C as starting material), m.p. 146°–147.5°, $[\alpha]_D$ − 12.0°, $\lambda_{max.}$ (0.1M-phosphate buffer at pH 6.0) 258 nm ($\epsilon$ 13,540).

EXAMPLE D8

2,2,2-Trichloroethyl
N-(7β-phenylacetamidoceph-3-em-3-ylmethyl)
3-(hydroxymethylcarbamoyl)pyridinium bromide
4-carboxylate, 1β-oxide 3-Hydroxymethylcarbamoylpyridine (106 mg., 0.7 mmole) was dissolved in dry N,N-dimethylformamide (2 ml.) and added to a stirred solution of 2,2,2-trichloroethyl 3-bromomethyl-7β-phenylacetamidoceph-3-em-4-carboxylate 1β-oxide (390 mg., 0.7 mmole) in dry N,N-dimethylformamide (5 ml.). The solution was stirred at 20°–25° for 18 hr., then diluted with water (100 ml.) and washed with ether (25 ml.), then methylene chloride (50 ml.). The aqueous portion was evaporated in vacuo and the residual brown foam treated with acetone - ether (1:1; 10 ml.) to provide the sulphoxide ester as a buff hygroscopic powder (331 mg., 76%), m.p. 172°–175° (decomp.), $[\alpha]_D$ + 26.3°, $\lambda_{max.}$ 269 nm ($\epsilon$ 12,600), $\nu_{max.}$ 1800 (azetidin-2-one), 1740 (CO$_2$CH$_2$CCl$_3$), 1673 and 1530 (CONH), and 1042 cm.$^{-1}$ (S→O), $\tau$ 0.26 (1H,t, J 6 Hz; NHCH$_2$OH), 0.55 (1H,s; pyridinium C$_2$-H), multiplets centred at 0.95, 1.02 and 1.65 (each 1H; pyridinium C$_6$-H, C$_4$-H and C$_5$-H respectively), 1.48 (1H,d, J 9 Hz; C$_6$H$_5$CH$_2$CONH-), 2.72 (5H,s; C$_6$H$_5$), 4.02 (1H,dd, J 5 and 9 Hz; C$_7$-H), 4.22 (2H, broad s; CH$_2$N$^+$), 4.78 and 4.99 (2H, AB-q, J 12 Hz; CH$_2$CCl$_3$), 4.94 (1H,d, J 5 Hz; C$_6$-H), 5.22 (2H,d, J 6 Hz; NHCH$_2$OH), 5.89 (low-field branch of partly obscured AB-q J 18 Hz; C$_2$-H$_2$), ca. 6.1–6.4 (broad peak; H$_2$O and OH), 6.28 and 6.48 (AB-q J 14 Hz; C$_6$H$_5$CH$_2$). Electrophoresis at pH 1.9 showed a single spot migrating towards the cathode, R$_c$2.0, which gave a mauve colour with potassium iodoplatinate spray reagent.

EXAMPLE D9

(i) 2,2,2-Trichloroethyl
N-(7β-formamidoceph-3-em-3-ylmethyl)-pyridinium
bromide-4-carboxylate, 1β-oxide 2,2,2-Trichloroethyl 3-bromomethyl 7β-formamidoceph-3-em-4-carboxylate, 1β-oxide (1.17 g., 2.5 mmole) was treated with dry pyridine (10 ml.) to give a deep-green solution which almost immediately deposited a fine solid. After stirring for 30 min. at 25° the suspension was diluted with methylene chloride (10 ml.), and refrigerated (−16°) overnight. The pale-green solid was collected, then immediately suspended in dry methylene chloride (20 ml.) and stirred magnetically for a brief period. Filtration provided the sulphoxide ester as a pale green solid (1.09 g., 80%), m.p. 155°–156°, $[\alpha]_D$ + 75°, $\lambda_{max.}$ 263 nm ($\epsilon$ 9,640), 275 nm (inflexion; $\epsilon$ 7,500), $\nu_{max.}$ 3400 (NH and H$_2$O), 1790 (azetidin-2-one), 1734 (CO$_2$CH$_2$CCl$_3$), 1674 and 1472 (CONH) and 1030 cm.$^{-1}$ (S→O), $\tau$ multiplets centred at 1.00 (2H), 1.32 (1H) and 1.78 (2H) (pyridinium o-, p- and m-protons respectively), 1.52 (1H,d, J 9 Hz; -CONH), 1.83 (1H,s; CHO), 3.89 (1H,dd, J 5 and 9 Hz; C$_7$-H), 4.27 (2H,s; CH$_2$N$^+$), 4.80 and 4.99 (2H, AB-q, J 12 Hz; CH$_2$CCl$_3$), 4.86 (1H,d, J 5 Hz; C$_6$-H), 5.89 and 6.29 (2H, AB-q, J 18 Hz; C$_2$-H$_2$). The sulphoxide ester migrated towards the cathode as a single spot, R$_c$2.9, on electrophoresis at pH 1.9 and gave a mauve colour upon spraying with potassium iodoplatinate.

(ii) 2,2,2-Trichloroethyl
N-[7β-aminoceph-3-em-3-ylmethyl]pyridinium
bromide/chloride 4-carboxylate 1β-oxide
hydrochloride.

A solution of 2,2,2-trichloroethyl N-[7β-formamidoceph-3-em-3-ylmethyl] pyridinium bromide 4-carboxylate 1β-oxide (547 mg., 1 mmole) in dry methanol was cooled to 0°–5° with magnetic stirring. Phosphorus oxychloride (0.35 ml., 3.82 mmole) was added and the solution stirred at 0°–5° for 30 min., then refrigerated overnight at −16°. Dilution with ether (ca. 40 ml.) precipitated a buff solid which was extremely hygroscopic. This was collected using additional ether, and whilst still moist with ether, transferred to a drying pistol, then dried (ca. 25°/1 mm.) to give the title *hydrochloride* (457 mg.), m.p. > 210°, $[\alpha]_D + 33°$, $\lambda_{max.}$ (MeOH) 261 nm ($E_{1cm.}^{1\%}$ 153) and 275 nm (inflexion, $E_{1cm.}^{1\%}$ 91), $\nu_{max.}$ ca. 2600 (—N$^+$H$_3$), 1800 (azetidin-2-one), 1738 (—CO$_2$CH$_2$CCl$_3$), and 1020 cm.$^{-1}$ (S→O), $\tau$ multiplets centred at 0.92 (2H), 1.28 (1H) and 1.74 (2H) (pyridinium o-, p- and m-protons respectively), 4.07 and 4.26 (2H, AB-q, J 16 Hz; -CH$_2$N$^+$), 4.48 and 4.67 (two 2H, d, J 5 Hz; C$_6$-H and C$_7$-H), 4.74 and 4.92 (2H,AB-q, J 12 Hz; —CH$_2$CCl$_3$), ca. 4.0–5.5 broad envelope; —N$^+$H$_3$ and H$_2$0), 5.75 and 6.04 (2H,AB-q,J 18 Hz; C$_2$-H$_2$). Electrophoresis at pH 1.9 showed a single spot migrating towards the cathode, R$_c$ 4.0, which showed mauve, and the presence of some tailing, upon spraying with potassium iodoplatinate.

(iii) 2,2,2-Trichloroethyl N-[7β-(2-thienylacetamido)ceph-3-em-3-ylmethyl]-pyridinium bromide/chloride 4-carboxylate 1β-oxide A stirred suspension of 2,2,2-trichloroethyl N-[7β-aminoceph-3-em-3-ylmethyl] pyridinium bromide/chloride 4-carboxylate, 1β-oxide (394 mg.) in dry methylene chloride (10 ml.) was treated with 2-thienylacetyl chloride (0.105 ml., 0.85 mmole) followed by N,N-dimethylacetamide (10 ml.). The mixture was stirred at ca. 24° for 30 min., complete solution being obtained after ca. 10 min. The dark solution was refrigerated for 1 hr., then poured into water (25 ml.) and methylene chloride (15 ml.). The aqueous layer was separated and washed with further methylene chloride (25 ml.). The combined organic portions were back-extracted with water (10 ml.). The combined aqueous portions were saturated with sodium chloride, then successively extracted with ethyl acetate (2 × 25 ml.), then methylene chloride (4 × 25 ml.). Evaporation of the combined dried ethyl acetate extracts gave a brown gum (32 mg.) and similarly the methylene chloride extracts gave a brown gum (105 mg.). Examination by electrophoresis at pH 1.9 showed the gums to be similar, with a single spot, R$_c$ 2.3, migrating towards the cathode with identical mobility to the sulphoxide pyridinium ester previously described. The gums were bulked and upon treating with acetone (10 ml.) solidified to give the title ester as a pale brown solid (51 mg.), m.p. 151°–157° (decomp.), $\lambda_{max.}$ 235 nm ($E_{1cm.}^{1\%}$ 189), 261 nm ($E_{1cm.}^{1\%}$ 149) and 275 nm (inflexion; $E_{1cm.}^{1\%}$ 121). The sulphoxide ester showed identical IR and PMR spectra to the sample described in Example D11(c).

EXAMPLE D10

(i) t-Butyl N-[7β-formamidoceph-3-em-3-ylmethyl] pyridinium bromide 4-carboxylate 1β-oxide Dry pyridine (3 ml.) was added to t-butyl 3-bromomethyl-7β-formamidoceph-3-em-4-carboxylate 1β-oxide (1.18 g., 3 mmole) giving a brown gum which slowly went into solution, and a pale-brown solid came out of solution. When the gum had all dissolved (ca. 10 min.) the resulting suspension was stirred for a further 5 min., then refrigerated overnight. The solid was collected, washed with ether (ca. 20 ml.), then dried to give the sulphoxide ester as a pale brown powder (1.24 g., 87.2%), m.p. 160°–162°, $[\alpha]_D + 3.7°$ (c 0.27) $\lambda_{max.}$ 263 nm ($\epsilon$ 10,910) and 275 nm (inflexion, $\epsilon$ 7,750), $\nu_{max.}$ 3320 (NH), 1802 (azetidin-2-one), 1718 (CO$_2$C(CH$_3$)$_3$), 1688 and 1512 (CONH), and 1031 cm.$^{-1}$ (S→O), $\tau$ multiplets centred at 0.98 (2H), 1.30 (1H) and 1.70 (2H) (pyridinium o-, p- and m-protons respectively), 1.46 (1H,d, J 9 Hz; CONH), 1.80 (1H,s, -CHO), 3.90 (1H,dd, J 5 and 9 Hz; C$_7$-H), 4.39 (2H,s; CH$_2$N$^+$), 4.90 (1H,d, J 5 Hz; C$_6$-H), 6.00 and 6.31 (2H, AB-q J 18 Hz; -CH$_2$SO), 8.46 (9H,s; —C(CH$_3$)$_3$). Electrophoresis at pH 1.9 showed a single spot, R$_c$ 2.8, migrating towards the cathode and which sprayed up mauve with potassium iodoplatinate.

(ii) t-Butyl N-[7β-Aminoceph-3-em-3-ylmethyl] pyridinium bromide/chloride 4-carboxylate, 1β-Oxide Hydrochloride To a stirred suspension of t-butyl N-[7β-formamidoceph-3-em-3-ylmethyl] pyridinium bromide 4-carboxylate, 1β-oxide (472 mg., 1 mmole) in dry methanol - ether (1:1, 2.5 ml.) at 0°–5° was added phosphorus oxychloride (0.23 ml., 2.5 mmole) dropwise at such a rate that the temperature of the mixture did not rise above 10°. The resulting solution was stirred at ca. 25° for 2 hr., during which time an oil was deposited. Ether (10 ml.) was then added to the mixture, causing the oil to solidify. The brown hygroscopic powder was collected and washed with additional ether, then dried to give the title hydrochloride (349 mg.), m.p. > 200°, $[\alpha]_D - 6°$, $\lambda_{max.}$ (MeOH) 259 nm ($E_{1cm.}^{1\%}$ 192), 275 nm (inflexion, $E_{1cm.}^{1\%}$ 117), $\nu_{max.}$ ca. 2600 (—N$^+$N$_3$), 1800 (azetidin-2-one), 1720 (—CO$_2$C(CH$_3$)$_3$), and 1030 cm.$^{-1}$ (S→O), $\tau$ multiplets centred at 0.94 (2H), 1.30 (1H) and 1.73 (2H) (pyridinium o-, p- and m-protons respectively), 4.40 (broad singlet; -CH$_2$N$^+$), 4.61 and 4.82 (two 1H,d, J 5 Hz; C$_6$-H and C$_7$-H), ca. 4.0 to 5.5 (broad envelope; -N$^+$H$_3$ and H$_2$O), 5.98 (2H,s; -CH$_2$SO), and 8.49 (9H,s; -C(CH$_3$)$_3$); there were also resonances centred at 6.60 and 8.88 $\tau$ attributed to the presence of ether (0.5 mole equiv.). Electrophoresis at pH 1.9 showed a spot migrating towards the cathode, R$_c$ 4.3, which gave a mauve color upon spraying with potassium iodoplatinate; some streaking of the spot became evident upon spraying.

Example D11

Preparation of N-[7β-(2-thienylacetamido)ceph-3-em-3-ylmethyl] pyridinium-4-carboxylate hydronitrate In the parts of this Example the end products and subsequent starting materials are designated as 3-bromomethyl compounds and salts with bromide anions. Owing to the incidence of chloride anion in the reactions, products are obtained which are mixed bromide/chloride materials. Equivalent weights and physical properties are calculated on the basis of the name given. The exchange of halogen may be estimated by chemical analysis or by UV absorption. Exchange of chlorine for bromine at the 3-methylene position is accompanied by a bathochromic shift in $\lambda_{max}$ (ethanol) of ~8nm.

(a) 2,2,2-Trichloroethyl 7β-Amino-3-bromomethylceph-3-em-4-carboxylate, 1β-Oxide An ice-cold mixture of tetrahydrofuran (20 ml) and concentrated hydrochloric acid (5 ml) was added, with magnetic stirring, to 2,2,2-trichloroethyl 3-bromomethyl-7β-formamidoceph-3-em-4-carboxylate, 1β-oxide (2.43 g, 5.2 mmole). The mixture was stirred for 30 min. to ensure complete solution, then refrigerated (ca. −16°) for 7 days during which time some white solid and a pale yellow gel were deposted. The mixture was distributed between ethyl acetate (75 ml) and water (150 ml), and the phases separated. The ethyl acetate layer was extracted with 2N-hydrochloric acid (3 × 30 ml). The combined aqueous portions were washed with ethyl acetate (2 × 30 ml), then mixed with ethyl acetate (250 ml) and taken to pH 7.0 with solid sodium hydrogen carbonate. The layers were separated and the aqueous phase extracted with further ethyl acetate (3 × 50 ml). The combined organic portions were washed with water (2 × 50 ml), dried and evaporated. The residue was treated with ether (ca. 50 ml) and re-evaporated, leaving the amino-ester (1.15 g; 50.3%) as a pale yellow solid, m.p. > 250°; $[\alpha]_D$ + 20°, $\lambda_{max}$ (MeOH) 277.5 nm ($\epsilon$ 8,680), $\nu_{max}$ (CHBr$_3$) 3410 and 3330 (NH$_2$), 1790 (azetidin-2-one), 1745 (CO$_2$CH$_2$CCl$_3$), and 1045 cm$^{-1}$ (S→O); $\tau$ 4.81 and 4.98 (2H, AB-q J 12 Hz; CH$_2$CCl$_3$), 4.99 and 5.08 (2H,d, J 5 Hz; C$_6$-H and C$_7$-H), 5.33 and 5.47 (2H, AB-q J 13 Hz; -CH$_2$Br), 5.97 and 6.24 (2H, AB-q J 18 Hz; —CH$_2$Br). TLC (CH$_2$Cl$_2$-Me$_2$CO (1:1)) revealed only one spot, R$_F$ 0.48, and the material was used directly for the next stage.

TLC of the ethyl acetate extract at pH ca. 0 revealed the presence of unchanged N-formylated material and also a further quantity of the title amine. Further extraction with 2N-hydrochloric acid (3 × 50 ml), followed by basification and extraction essentially as described above, provided an additional amount of less pure amine ester (315 mg, 13.7%) as a yellow solid, $\lambda_{max}$ (MeOH) 275 nm ($\epsilon$ 6,830).

(b) 2,2,2-Trichloroethyl 3-Bromomethyl-7β-(2-thienylacetamido) ceph-3-em-4-carboxylate, 1β-oxide A solution of 2,2,2-trichloroethyl 7β-amino-3-bromomethylceph-3-em-4-carboxylate, 1β-oxide (1.36 g; 3.08 mmole) in dry methylene chloride (25 ml) was treated with a solution of N,N'-dicyclohexylcarbodiimide (0.67 g; 3.23 mmole) in methylene chloride (13 ml, with 12 ml. washings) followed by 2-thienylacetic acid (0.46 g; 3.23 mmole) in methylene chloride (7 ml + 7 ml washings). The mixture quickly became cloudy and a white solid was precipitated. After stirring for 3 hr. at room temperature the mixture was refrigerated for 30 min. and the white solid (probably N,N'-dicyclohexylurea) collected by filtration (0.57 g, 78%). The filtrate was evaporated in vacuo, the residue was dissolved in ethyl acetate (125 ml) and washed successively with 3% aqueous sodium hydrogen carbonate, 2N-hydrochloric acid, 3% aqueous sodium hydrogen carbonate, and saturated brine (50 ml each). The dried solution was evaporated, treated with ether (ca. 50 ml) and re-evaporated to provide the sulphoxide ester as a yellow solid (1.74 g; ca. 100%), m.p. 159°–160°, $[\alpha]_D$ + 57° (c 0.26), $\lambda_{max}$ 233.5nm ($\epsilon$ 11,100) and 275.5 nm ($\epsilon$ 7,510), $\nu_{max}$ 3300 (NH), 1780 (azetidin-2-one), 1738 (CO$_2$CH$_2$CCl$_3$), 1658 and 1531 (CONH), and 1032 (S→O), $\tau$ 1.58 (1H,d, J 9 Hz; -NH), 2.65 (1H,t, J 3.5 Hz; =CH-S), 3.06 (2H,d, J 3.5 Hz; =CH-CH=), 4.10 (1H,dd, J 5 and 9 Hz; C$_7$—H), 4.79 and 4.95 (2H, AB-q, J 12 Hz; CH$_2$CCl$_3$). 4.98 (1H,d, J 5 Hz; C$_6$-H), 5.38 and 5.42 (2H, AB-q, J 11 Hz; CH$_2$Br), 5.98 and 6.26 (2H, AB-q J 18 Hz; C$_2$-H$_2$), and 6.05 and 6.25 (2H, AB-q, J 16 Hz; —CH$_2$CONH). TLC (CH$_2$Cl$_2$:Me$_2$CO (4:1)) showed one major spot (R$_F$0.64), together with trace impurities at R$_F$0.00 and R$_F$0.90. The material was carried through to the next stage without further purification.

(c) 2,2,2-Trichloroethyl N-[7β-(2-Thienylacetamido)ceph-3-em-3-ylmethyl] pyridinium bromide 4-carboxylate, 1β-Oxide A solution of 2,2,2-trichloroethyl 3-bromomethyl-7β-(2-thienylacetamido)ceph-3-em-4-carboxylate, 1β-oxide (1.50 g; 2.66 mmole) in dry (distilled from potassium hydroxide pellets) pyridine (11.5 ml) was stirred at room temperature for 3$^3$/4hr. A solid came out of solution after approximately 2$^3$/4 hr. stirring. The mixture was refrigerated (ca. 6°) for 30 min., and the solid collected with the aid of ether. The solid was suspended in ether (100 ml) and stirred for 45 min. then filtered and dried to give the sulphoxide ester as a pale brown hygroscopic solid (1.12 g; 66%), m.p. 156°–160°, $[\alpha]_D$ +33.5° (c 0.20), $\lambda_{max}$ 236 nm ($\epsilon$ 11,990), 262 nm ($\epsilon$ 10,420), and 274 nm (inflexion; $\epsilon$ 8,160), $\nu_{max}$3350 (NH), 1790 (azetidin-2-one), 1730 (CO$_2$CH$_2$CCl$_3$), 1660 and 1510 (CONH), and 1035 cm$^{-1}$ (S→O), $\tau$ multiplets centred at 0.91 (2H), 1.26 (1H) and 1.71 (2H) (pyridinium; o-, p and m-protons respectively, 1.42 (1H,d, J 9 Hz; NH), 2.57 (1H,t, J 3.5 Hz; =CH-S), 3.00 (2H,d, J 3.5 Hz; =CH-CH=), 3.94 (1H,dd, J 5 and 9 Hz; C$_7$-H), 4.19 (2H, broad s; CH$_2$N$^+$), 4.72 and 4.92 (2H, AB-q, J 12 Hz; CH$_2$CCl$_3$), 4.80 (1H,d, J 5 Hz; C$_6$-H), 5.84 and 6.21 (2H, AB-q, J 18 Hz; C$_2$-H$_2$), 6.04 and 6.23 (2H, AB-q, J 6 Hz; CH$_2$CONH) (Found: C, 40.1, H, 3.3; N, 6.5; S, 10.5; total halogen content, 4.2 equiv./mole compound C$_{21}$H$_{19}$BrCl$_3$N$_3$O$_5$S$_2$ (643.8) requires: C, 39.2; H 3.0; N, 6.5; S, 10.0%; total halogen content, 4.0 equiv./mole compound). The sulphoxide ester migrated towards the cathode as a single spot, R$_c$2.3, on electrophoresis at pH 1.9 and gave a mauve colour upon spraying with potassium iodoplatinate.

(d) N-[7β-(2-Thienylacetamido)ceph-3-em-3-ylmethyl] pyridinium-4-carboxylate hydronitrate 2,2,2-Trichloroethyl N-[7β-(2-thienylacetamido)-ceph-3-em-3-ylmethyl]pyridinium bromide 4-carboxylate, 1β-oxide (3.85 g; 5.95 mmole) was suspended in dry methylene chloride (76 ml), dry N,N-dimethylformamide (2 ml) was added and the resulting solution treated with phosphorus trichloride (5 equiv.). The solution was stirred at room temperature for 1½ hr. during which time a solid was precipitated. After refrigration for 30 min. the solid was collected, washed well with dry methylene chloride and dried to give 2,2,2-trichloroethyl N-[7β-(2-thienylacetamido)ceph-3-em-3-ylmethyl]pyridinium bromide 4-carboxylate as a hygroscopic white powder (2.42 g.; 65%), m.p. 147°–151°, $[\alpha]_D$−16° (c 0.25), $\lambda_{max.}$ 238 nm ($\epsilon$ 11,100) and 260 nm (10,670).

Zinc chloride (20 mg.), zinc dust (2.0 g.) and a solution of a portion of the above ester (2.0 g., 3.19 mmole) dissolved in anhydrous formic acid (40 ml.) were added in succession to anhydrous formic acid (40 ml.) stirred at 0°–5°. The cooling bath was withdrawn and the mixture stirred at 22° for 2 hr., then filtered. The combined filtrate and filter pad washings (formic acid, ca. 5 ml.) were evaporated in vacuo and the residual oil dissolved in formic acid — water (4:1, 10 ml.). This solution was passed through an ion-exchange column consisting of De-acidite FF (Cl$^-$) over De-acidite FF (OAc$^-$) (20 ml. of each resin). The column was washed with formic acid - water (4:1, 80 ml.). The first 50 ml. of eluate showed optical activity and was evaporated in vacuo. The residue was dissolved in water (40 ml.) - glacial acetic acid (3 ml.), and washed with ether (2 × 40 ml.).

The combined ether washings were back-extracted with water (40 ml.). The combined aqueous portions were filtered, degassed by brief rotary-evaporation, then freeze-dried to provide a pale brown granular solid (1.145 g.). A portion of this material (500 mg.) was dissolved in water (2.5 ml.) and concentrated nitric acid was added dropwise until crystallisation took place. The mixture was refrigerated briefly, and then filtered to give the hydronitrate as off-white prisms (360 mg., 54%), m.p. 135°–136°, $[\alpha]_D - 6°$ (Me$_2$CO-H$_2$O (1:1)), $\lambda_{max.}$ (H$_2$O) 238 nm (E$_{1cm.}$$^{1\%}$ 287) and 255 nm. (inflexion; E$_{1cm.}$$^{1\%}$ 250; R° 1.15. [R° = Ratio of E$_{1cm.}$$^{1\%}$ values at 238 nm. and 255 nm]).

The above material showed a single spot on electrophoresis which migrated towards the cathode exactly as did a sample of hydronitrate prepared by adding concentrated nitric acid to aqueous acetic acid (4:1) solution of N-[7β-(2-thienylacetamido)ceph-3-em-3-ylmethyl]pyridinium 4-carboxylate (cephaloridine) obtained by a route using cephalosporin (as starting material), m.p. 145°–146°, $[\alpha]_D$ −20.7° (Me$_2$CO-H$_2$O (1:1)), $\lambda_{max.}$ (H$_2$O) 235 nm (ε 14,640), 255 nm (inflexion; ε 13,300).

EXAMPLE D12

Preparation of
N-[7β-(2-thienylacetamido)ceph-3-em-3-ylmethyl]-pyridinium-4-carboxylate hydronitrate (a) t-Butyl
7β-Amino-3-bromomethylceph-3-em-4-carboxylate, 1β-Oxide Hydrochloride To a suspension of t-butyl 3-bromomethyl-7β-formamidoceph-3-em-4-carboxylate 1β-oxide (982 mg., 2.5 mmole) in dry methanol- ether (1:1; 20 ml.) stirred at 0°–5° was added phosphorus oxychloride (0.575 ml., 6.3 mmole) at such a rate that the temperature of the mixture did not rise above 10°. The addition took place over ca. 10 min. and during this time the starting material went into solution and almost immediately a new crystalline solid was deposited. The mixture was stirred for 30 min. then refrigerated for 30 min. and the white crystalline solid collected, using ether to give the hydrochloride (800 mg., 87.7%), m.p. >200°, $[\alpha]_D$ + 23°, $\lambda_{max.}$ (MeOH) 276.5 nm (ε 8,680), $\nu_{max.}$ ca. 2550 (—N$^+$H$_3$), 1796 (azetidin-2-one), 1712 (CO$_2$CH$_2$CCl$_3$), and 1005 cm.$^{-1}$ (S→0), τ 4.62 (1H,d, J 5 Hz; C$_7$-H), 4.85 (1H,d, J 5 Hz; C$_6$—H), 5.36 and 5.01 (2H, Ab-q J 12 Hz; -CH$_2$Br), 5.99 (2H,s; C$_2$-H$_2$), ca. 4.0-6.0 (broad hump; —N$^+$H$_3$ and H$_2$O) and 8.45 (9H,s; —C(CH$_3$)$_3$). TLC (CH$_2$Cl; Me$_2$Co (1:1)) showed a single spot, R$_F$ 0.25.

(b) N-[7β-(2-Thienylacetamido)ceph-3-em-3-ylmethyl] pyridinium-4-carboxylate hydronitrate.

A stirred suspension of t-butyl 7β-amino-3-bromomethylceph-3-em-4-carboxylate 1β-oxide hydrochloride (1.325 g., 3.3 mmol) in dry methylene chloride (33 ml.) was cooled to 0°–5° and treated with a solution of 2-thienylacetyl chloride (0.58 g., 3.6 mmole) in methylene chloride (5 ml., with 5 ml. washings). N,N-dimethylacetamide (40 ml.) was added dropwise over 30 min. and the resulting solution stirred for a further 15 min., then poured into water (100 ml.) and the layers separated. The organic layer was successively washed with water (100 ml.), 3% aqueous sodium hydrogen carbonate and saturated brine (50 ml. each), then dried by filtration through magnesium sulphate; and evaporated to a brown gel (1.57 g.), $\lambda_{max.}$ 235 nm (E$_{1cm.}$$^{1\%}$ 219), 273.5 nm (E$_{1cm.}$$^{1\%}$ 190).

The above gel was dissolved in dry pyridine (10 ml.) and stirred for 3 hr. Ether (60 ml.) was added to precipitate a brown solid, which after refrigeration for 1 hr., was collected using ether (1.59 g.), m.p. ca. 157° (decomp), $[\alpha]_D$ + 9.9° $\lambda_{max.}$ 238 nm (E$_{1cm.}$$^{1\%}$ 199), 262 nm (E$_{1cm.}$$^{1\%}$ 203) and 275 nm (inflexion: E$_{1cm.}$$^{1\%}$ 132), $\nu_{max.}$ 1792 (azetidin-2-one), 1710 (CO$_2$C(CH$_3$)$_3$), 1675 and 1510 (CONH) and 1030 cm.$^{-1}$ (S→0), τ multiplets centred at 0.99 (2H), 1.32 (1H) and 1.78 (2H) pyridinium o-, p and m-protons respectively), 1.57 (1H,d, J 9 Hz; —NH), 2.63 (1H,t, J 3.5 Hz; —CH—S), 3.05 (2H,d, J 3.5 Hz; —CH-CH=), 4.04 (1H,dd, J 5 and 9 Hz; C$_7$-H) 4.42 (2Hz; -CH$_2$N)$^+$, 4.91 (1H,d, J 5 Hz; C$_6$-H), 6.02 and 6.29 (2H, Ab-q J 18 Hz; —CH$_2$SO), 6.07 and 6.23 (2H,AB-q J 16 Hz; —CH$_2$CONH), and 8.48 (9H,s -C(CH$_3$)$_3$). Electrophoresis showed a single spot, R$_c$ 2.7, migrating towards the cathode and which gave a mauve colour with potassium iodoplatinate spray reagent.

The foregoing sulphoxide ester (1.45 g.) was dissolved in methylene chloride (25 ml.) and phosphorus trichloride (0.89 ml., 10.2 mmole) was added. The mixture was stirred for 2 hr., then refrigerated for 1 hr. before evaporation in vacuo to dryness. The residue was treated with acetone (15 ml.) - water (1 ml.) and after brief refrigeration the pale-yellow crystalline solid was collected (274 mg.), m.p. 142°–144°, $[\alpha]_D$−1° $\lambda_{max.}$ 240 nm (E$_{1cm.}$$^{1\%}$ 202) and 259 nm (E$_{1cm.}$$^{1\%}$ 194), $\lambda_{max.}$ 3200 (NH), 1785 (azetidin-2-one), 1725 (CO$_2$C(CH$_3$)$_3$), 1690 and 1540 cm.$^{-1}$ (CONH), τ 0.86 (1H,d, J 9 Hz; -NH), multiplets centred at 0.95 (2H, 1.32 (1H) and 1.76 (2H) (pyridinium o-, p and m-protons respectively), 2.64 (1H,m; —CH-S), 3.08 (2H,m; —CH—CH=), 4.20 (1H,dd J 5 and 9 Hz; C$_7$-H) 4.42 (broad singlet on top of envelope; —CH$_2$N$^+$ and H$_2$O), 4.81 (1H,d J 5 Hz; C$_6$—H), 6.23 (2H,s, -CH$_2$CONH), 6.37 and 6.55 (2H, Ab-q J 18 Hz; —CH$_2$S), 8.08 (9H,s, -C(CH$_3$)$_3$). Electrophoresis showed one spot, R$_c$ 2.5, migrating towards the cathode which sprayed up mauve with potassium iodoplatinate reagent. The filtrate was evaporated to dryness and the residue treated with ether (150 ml.) to give a yellow powder (928 mg.), m.p. 95°, $[\alpha]_D$ − 10° $\lambda_{max.}$ 240 nm (E$_{1cm.}$$^{1\%}$ 188) and 257 nm (E$_{1cm.}$$^{1\%}$ 173). Electrophoresis showed a major spot, R$_c$ 2.5, and a minor spot, R$_c$ 0.0, both of which migrated towards the cathode and gave a mauve colour upon spraying with potassium iodoplatinate.

A portion of the second-crop material obtained above (500 mg.) was dissolved in ice-cold trifluoroacetic acid (5 ml.) and the resulting solution stirred for 2 hr. at 0°–5°, then evaporated in vacuo. The residue was treated with acetic acid (ca. 5 ml.), and re-evaporated. The residue yellow oil was suspended in water and the pH adjusted to 4.0 with concentrated ammonia solution. The resulting solution was passed through a De-acidite FF (OAc$^-$) ion-exchange column (5 ml.), the column being washed through with water (50 ml.). The first 40 ml. of eluate showed optical activity and after de-gassing by brief rotary-evaporation was freeze-dried to give a gummy solid. This was dissolved in water (4 ml.) and the pH of the solution taken from pH 4.5 to pH 1.4 with concentrated nitric acid. A beige solid was immediately deposited and after refrigeration (1 hr.) was collected and washed with water (1 ml.) to give the hydronitrate (101 mg., 17.4%), m.p. 140°–142°, $[\alpha]_D$−9° (c 1.00; Me$_2$CO-H$_2$O (1:1)) $\lambda_{max.}$ (H$_2$O) 238 nm (E$_{1cm}$$^{1\%}$ 294) and 255 nm (inflexion; E$_{1cm.}$$^{1\%}$ 271); R°1.085; the material was identical on electrophoresis to the hydronitrate described in Example D11 (d).

EXAMPLE D13

Preparation of 2,2,2-Trichloroethyl N-[7β-(2-thienylactamido)ceph-3-em-3-ylmethyl] pyridinium bromide-4-carboxylate 1β-oxide 2-Thienylacetyl chloride (1.51 g., 9.405 mmole) dissolved in methylene chloride (20 ml.) was added to a stirred suspension of 2,2,2-trichloroethyl 7β-amino-3-bromomethylceph-3-em-4-carboxylate, 1β-oxide hydrochloride (4.08 g., 8.55 mmole) in methylene chloride (80 ml.) at 0°–5°. N,N-Dimethylacetamide (10 ml.) was added dropwise until complete solution was obtained (during this addition the temperature rose to ca. 10°). After stirring for a further 20 min. at 0°–5° the dark solution was poured into ice-cold water (200 ml.) and the layers separated. The aqueous layer was extracted with additional methylene chloride (20 ml.). A small amount of an insoluble white solid separated at the interfaces during these extractions and was shown by TLC ($CH_2Cl_2$-$Me_2CO$ (1:1)) to be largely the starting ester ($R_F$ 0.37) together with two minor components ($R_F$ 0.81 and 0.89). The combined organic extracts were washed with 3% aqueous sodium hydrogen carbonate (100 ml.) and water (200 ml.), then dried ($MgSO_4$) and evaporated in vacuo. The residual gel was treated with ether (50 ml.), which caused it to partly solidify. The ether was decanted to leave a pale-yellow solid (4.55 g.), $\lambda_{max.}$ 233 nm. ($E_{1cm}^{1\%}$ 188) and 278 nm ($E_{1cm}^{1\%}$ 139). This was dissolved in dry pyridine (30 ml.) with magnetic stirring and almost immediately a fine-green solid came out of solution. After stirring for 30 min. at ca. 23° the suspension was diluted with ether (100 ml.), and stirred for an additional 1 hr., then filtered to give the sulphoxide ester as a pale-green hygroscopic solid (3.85 g., 69.5%), m.p. 150°–151°, $\lambda_{max}$ 237.5 nm ($\epsilon$ 11,590), 262 nm ($\epsilon$ 10,430), and 275 nm (inflexion; $\epsilon$ 7,600); and with identical mobility on electrophoresis to a sample of the sulphoxide ester described in Example D11(c).

EXAMPLE D14

Preparation of N-[7β-formamidoceph-3-em-3-ylmethyl]pyridinium-4-carboxylate, 1β-oxide (a) from the product of Example B4

(b) from the free acid of the product of Example B4

(c) from 7β-formamido-3-methylceph-3-em-4-carboxylic acid, 1β-oxide (a) A solution of t-butyl 3-bromomethyl-7β-formamidoceph-3-em-4-carboxylate, 1β-oxide (393 mg, 1 mmole) in dry pyridine (5 ml) was kept at ca. 20° for 30 minutes when a white solid had separated. Water (20 ml) was added and the solvents were removed in vacuo, the last traces of water being removed by addition of industrial methylated spirits and re-evaporation. The residual crude t-butyl N-[7β-formamidoceph-3-em-3-ylmethyl]pyridinium bromide 4-carboxylate 1β-oxide, obtained as an orange solid, was dissolved in trifluoroacetic acid (5 ml) and left at ca. 20° for 30 minutes. Evaporation gave an oil which stll contained unchanged betaine ester on electrophoresis at pH 1.9. The oil was re-treated with trifouoroacetic acid (5 ml) for a further 15 minutes and re-evaporated. The residual oil was dissolved in water (20 ml), and the solution was washed with ether (25 ml), and passed through a column (5 × 1cm) of Deacidite FF ion-exchange resin (OAc⁻ form), eluting with water. The eluate with a positive optical rotation was freeze-dried to give the title betaine 1β-oxide (288 mg, 86% for anhydrous), $\lambda_{max}$ (pH 6 0.1 M phosphate) 257 nm ($E_{1cm}^{1\%}$ 331), $\nu_{max.}$ 1776 (azetidin-2-one), 1672 (CONH), 1610 ($CO_2^-$) and 1020 cm⁻¹ (S→O), $\tau$ 0.68 (2H, d, J 5.5 Hz; $N^+$=C$\underline{H}$-), 1.41 (1H,m; $N^+$=CH-CH=C$\underline{H}$), 1.69 (1H,d, J 9 Hz; N$\underline{H}$), 1.81 (2H,m; $N^+$=CH-C$\underline{H}$), 1.84 (1H,s; C$\underline{H}$O), 4.18 (1H,dd, J 9,4.5 Hz; $C_7$-$\underline{H}$), 4.27, 4.75 (2H, Ab-q, J 14 Hz; $C_3$-C$\underline{H}_2$$N^+$), 5.12 (1H,d, J 4.5 Hz; $C_6$-$\underline{H}$), 6.47 (broad s; $C_2$-$\underline{H}_2$) and $\underline{H}_2$O), 8.08 (1H,s; ca. 0.3 M C$\underline{H}_3$$CO_2$H).

(b) 3-Bromomethyl-7β-formamidoceph-3-em-4-carboxylic acid.

(i) 3-Bromomethyl-7β-formamidoceph-3em-4-carboxylic Acid, 1β-Oxide

A solution of t-butyl 3-bromomethyl-7β-formamidoceph-3-em-4-carboxylate, 1β-oxide (393 mg, 1 mmole) in trifuoroacetic acid (2 ml) was kept at ca. 20° for 10 minutes and evaporated. The pale orange solid residue was triturated with ether and re-extracted to give the title acid 1β-oxide (330 mg, 98%), m.p. > 200° C, $[\alpha]_D$ + 52°, $\lambda_{max}$ (dissolved in a few drops of dimethylformamide and diluted with methanol) 266.5 nm ($\epsilon$ 6,050), $\nu_{max}$ 3290 (NH), ca. 2600 and 1781 ($CO_2$H), 1783 (azetidin-2-one), 1650 and 1530 (CONH) and 992 cm⁻¹ (S→O), $\tau$ 1.66 (1H,d, J 9.5 Hz; N$\underline{H}$), 1.88 (1H,s; C$\underline{H}$O), 4.06 (1H,dd, J 9.5,5 Hz; $C_7$—$\underline{H}$), 5.04 (1H,d, J 5Hz; $C_6$—$\underline{H}$), 5.29, 5.58 (2H, AB-q, J 10 Hz; $C_3$-C$\underline{H}_2$Br), 6.06, 6.29 (2H, Ab-q, J 18 Hz; $C_2$—$\underline{H}_2$) (Found: Br, 22.8. $C_9H_9BrN_2O_5S$ (337.2) requires Br, 23.7%

(ii) 3-Bromomethyl-7β-formamidoceph-3-em-4-carboxylic acid, 1β-oxide was suspended in dry pyridine; the solid went into solution on keeping overnight. An aliquot of this solution was examined by electrophoresis at pH 1.9 : it showed one major spot migrating towards the cathode with the same mobility as material prepared as in (a) above, and giving the same dark blue-mauve colour on spraying with iodoplatinate reagent.

(c) A suspension of 7β1 -formamido-3-methylceph-3-em-4-carboxylic acid, 1β-oxide (1.29 g, 5 mmole) in dry 1,2-dichloroethane (40 ml) was heated under reflux with hexamethyl disilazane (1.55 ml, ca. 8 mmole) to give a clear pale orange solution. The solution was evaporated to a gelatinous solid which was dried at 1 mm. overnight and redissolved in dry 1,2-dichloroethane (200 ml). Dry nitrogen was passed through the solution for 15 minutes and N-bromosuccinimide (1.335 g, 7.5 mmole) was added. The solution was cooled to 0° and irradiated for 3½ hours with a Hanovia 125-watt medium pressure mercury arc with a Pyrex-filter, the temperature being kept at 0°. Pyridine (20 ml) was added, the mixture was stirred for 30 minutes, and water (100 ml) was added. The aqueous phase was washed with ethyl acetate (100 ml), concentrated to ca 20 ml and passed through a column (i.d. 2 cm) of acidic alumina (5 cm) and Deacidite FF ion-exchange resin (OAc⁻ form; 5 cm), eluting with water. The eluate with a positive optical rotation was freeze-dried and the residual solid was stirred with acetone (50 ml) to give the title betaine 1β-oxide (1.08 g, 49%), $\lambda_{max}$ (ph 6 0.1 M phosphate) 258.5 nm ($E_{1cm}^{1\%}$ 320), $\tau$ 7.41 (ca. 2H,s; ca. 0.5 M succinimide) otherwise resembling that in (a) above (Found C, 43.7, 43.7; H, 3.9, 3.85; N, 11.4, 11.6; S, 7.7. $C_{14}H_{13}N_3O_5S$. $3H_2O$. 0.5 M $C_4H_5NO_2$(438.9) requires C, 43.8; H, 4.9; N, 11.2; S, 7.3%).

The product of this example may be deformylated by the following method.

N-[7β-Aminoceph-3-em-3-ylmethyl]pyridinium Chloride 4-Carboxylic Acid, 1β-Oxide, Hydrochloride A suspension of N-(7β-formamidoceph-3-em-3-ylmethyl) pyridinium 4-carboxylate, 1β-oxide (336 mg) in methanol-ether (1:1; 10 ml) was cooled in an ice-bath and phosphorus oxychloride (0.23 ml, 2.5 mmole) was added dropwise with stirring. The resulting yellow solution was stirred at 0° to 5° for 1 hour and ether (10 ml) was added to precipitate the title compound as a pale yellow hygroscopic solid (220 mg), $\lambda_{max}$ (pH 6 0.1M phosphate) 258.5 nm ($E_{1cm}^{1\%}$ 287 (Found: Cl, 16.4. $C_{13}H_{15}Cl_2N_3O_4S$ (380.3) requires Cl, 18.65%), one major spot migrating towards the cathode on electrophoresis at pH 2.2 which gave a slowly developing blue colour on spraying with iodoplatinate reagent.

REACTIONS INVOLVING SULPHUR NUCLEOPHILES

EXAMPLE D15

(i) 2,2,2-Trichloroethyl 3-Methylthiomethyl-7β-phenylacetamidoceph-3-em-4-carboxylate, 1β-Oxide.

Methanethiol was bubbled into a solution of 2,2,2-trichloroethyl 3-bromomethyl-7β-phenylacetamidoceph-3-em-4-carboxylate 1β-oxide (0.559 g, 1 mmole) and triethylamine (0.14 ml, 1 mmole) in N,N-dimethylformamide (20 ml) for 2 minutes. The solution was left at 20° for 30 minutes, when dilution of an aliquot with ethanol gave a solution with $\lambda_{max.}$ 274 nm. Nitrogen was passed for 45 minutes through the dimethylformamide solution which was then diluted with water and methylene chloride (25 ml of each). The aqueous phase was separated and extracted with methylene chloride (25 ml). The methylene chloride layers were combined and washed with water (3 × 25 ml), 2N-hydrochloric acid (25 ml), and water (25 ml), dried and evaporated to give a yellow oil (0.64 g). This oil was dissolved in acetone (10 ml) and the solution was diluted with light petroleum (b.p. 40° to 60° 20 ml) to give a pale-orange gelatinous solid which was filtered off, washed with acetone-light petroleum (1:2), and dried (0.403g, 77%), $\lambda_{max.}$ 273.5nm ($E_{1cm}^{1\%}$ 155). Part (0.23g) of this solid was crystallised from ethanol to give the ester 1β-oxide (0.13g,) m.p. 141° to 143°, $[\alpha]_D$ +73°, $\lambda_{max.}$ 274 nm ($\epsilon$ 7,900), $\nu_{max.}$ (CHBr$_3$) 3384 (NH), 1790 (azetidin-2-one), 1736 (CO$_2$R), 1680 and 1500 (CONH), and 1042 cm.$^{-1}$ (S→O), $\tau$ 1.63 (1H, d, J 9 Hz; N$\underline{H}$), 2.71 (5H, s, C$_6\underline{H}_5$), 4.19 (1H, dd, J 9 and 5 Hz; C$_7$-$\underline{H}$), 4.80 and 5.00 (2H, AB-q; J 12 Hz; C$\underline{H}_2$CCl$_3$), 5.00 (1H, d; J 5 Hz; C$_6$-$\underline{H}$), 5.91 and 6.30 (2H, AB-q, J 18 Hz; C$_2$-$\underline{H}_2$), 6.28 and 6.49 (2H, AB-q; J 14 Hz; C$_3$-C$\underline{H}_2$S), 6.36 (2H, s, PhC$\underline{H}_2$), 8.00 (3H, s, SC$\underline{H}_3$) (Found: C, 42.7 H, 3.6; Cl 19.7; N, 5.4; S, 12.0. $C_{19}H_{19}Cl_3N_2O_5S_2$ (525.9) requires C, 43.4; H, 3.6; Cl, 20.2; N, 5.3; S, 12.2%).

(ii) 2,2,2,Trichloroethyl 3-Methylthiomethyl-7β-phenylacetamidoceph-3-em-4-carboxylate.

A solution of impure 2,2,2-trichloroethyl 3-methylthiomethyl-7β-phenylacetamidoceph-3-em-4-carboxylate, 1β-oxide (266 mg, ca. 0.5 mmole) and phosphorus trichloride (0.10 ml, ca. 5 equiv.) was stirred at 20° for 2.5 hours, stored at 0° for 64 hours and then heated under reflux for 1 hour, when t.l.c. (acetone-methylene chloride; 1:25) showed only a trace of starting material remaining. The solvent was evaporated and the residual oil was purified by preparative layer chromatography on Kieselgel (PF$_{254+366}$), eluting with acetone-methylene chloride (1:25), to give the title ester as a pale-orange gelatinous solid (42 mg) $\lambda_{max}$ 267 nm ($E_{1cm}^{1\%}$ 126), $\tau$ (CDCl$_3$), 2.72 (5H, s, C$_6\underline{H}_5$), 3.87 (1H, d, J 9 Hz; N$\underline{H}$), 4.23 (1H, dd, J 9 and 5 Hz; C$_7$-$\underline{H}$), 5.02 (1H, d, J 5 Hz; C$_6$-$\underline{H}$), 5.04 and 5.31 (2H, AB-q, J 12 Hz; C$\underline{H}_2$CCl$_3$) 6.24 and 6.60 (2H, AB-q, J 14 Hz; C$_3$-C$\underline{H}_2$S), 6.39 (2H, s, PhC$\underline{H}_2$), 6.45 (2H, s, C$_2$-$\underline{H}_2$) and 7.97 (3H, s, SC$\underline{H}_3$):

(iii) 3-Methylthiomethyl-7β-phenylacetamidoceph-3-em-4-carboxylic Acid.

A solution of 2,2,2-trichloroethyl 3-methylthiomethyl-7β-phenylacetamidoceph-3-em-4-carboxylate (ca. 2.7g, 5 mmole) in methylene chloride (20 ml) was cooled to 0 and formic acid (40 ml) was added. Zinc powder (4g, activated by washing with 2N-hydrochloric acid) was added and the reaction mixture was kept at 0° for 1 hour when t.l.c. (acetone-methylene chloride; 1:15) showed that little reaction had occurred.

The reaction mixture was stirred at 20° for 5 hours when t.l.c. indicated that only 5 to 10% of the starting material remained. The reaction mixture was filtered and the filtrate was evaporated in vacuo. The residual oil was dissolved in ethyl acetate (100 ml) and extracted with 3%-sodium hydrogen carbonate solution. (2 × 100 ml). The aqueous extracts were washed with ethyl acetate (50 ml), acidified to pH 2.3 with 10N-hydrochloric acid under a layer of ethyl acetate (75 ml). The aqueous phase was re-extracted with ethyl acetate (2 × 50 ml), and the combined ethyl acetate extracts were washed with water (100 ml), dried and evaporated in vacuo to give the title acid as a pale yellow foam. (1.54g, 81.5%), $\lambda_{max.}$ (pH 6 phosphate) 263.5 nm ($\epsilon$ 8,470), $\tau$ (D$_2$O,NaHCO$_3$) 2.66 (5H, s, C$_6\underline{H}_6$), 4.49 (1H, d, J 5 Hz; C$_7$-$\underline{H}$), 4.98 (1H, d, J 5 Hz; C$_6$-$\underline{H}$), 6.33 and 6.73 (2H, AB-q, J 14 Hz; C$_3$—C$\underline{H}_2$S), 6.35 and 6.75 (2H, AB-q, J 18 Hz; C$_2$—$\underline{H}_2$), 6.36 (2H, s, PhC$\underline{H}_2$), 8.01 (3H, s, SC$\underline{H}_3$).

(iv) 7β-Amino-3-methylthiomethylceph-3-3m-4-carboxylic acid

Trimethylsilyl chloride (3.27 ml, 27.65 mmole) was added to a solution of 3-methylthiomethyl-7β-phenylacetamidoceph-3-em-4-carboxylic acid (1.325 g, 3.5 mmole) and pyridine (2.11 ml, 26.25 mmole) in dry methylene chloride (130 ml). The reaction mixture was stirred at ca.30° for 1.75 hours and then cooled to −12°. Pyridine (4.09 ml, 55 mmole) and phosphorus pentachloride (2.865 g, 13.8 mmole) in dry methylene chloride (20 ml) were added, and the mixture was stirred at −123° for 40 minutes when cold methanol (55 ml) was added slowly so that the temperature did not exceed −10°. The mixture was stirred at −10° for 30 minutes when the cooling-bath was removed and stirring was continued for a further hour. The reaction solution was added to aqueous formic acid (50% 7.5 ml) and the pH was adjusted to 2.0 with triethylamine. A fine solid separated from the solution on stirring at this pH for 45 minutes. This solid was filtered off and dried to give the title amino acid (140 mg, 15%), $\lambda_{max.}$ (pH6 phosphate) 265 nm ($E_{1cm}^{1\%}$ 303), $\tau$ (D$_2$O, NaHCO$_3$), 6.80, 8.74 (typical signals for HN$^+$(C$_2$H$_5$)$_3$; 1/6 mole) contaminated with, presumably, triethylamine hydrochloride. The pH of the filtrate was adjusted to 3.5 with triethylamine when more solid began to separate. The mixture was kept at 4° overnight, when the solid was filtered off, washed with methylene chloride and dried to give a second crop of the amino acid (98 mg, 11%), $\lambda_{max.}$ (pH 6 phosphate) 266.5 nm ($\epsilon$ 9,500).

(v) 2,2,2-Trichloroethyl 7β-Amino-3-methylthiomethylceph-3-em-4-carboxylate, Hydrogen p-Toluenesulphonate and Hydrochloride.

A solution of 2,2,2-trichloroethyl 3-methylthiomethyl-7β-phenylacetamidoceph-3-em-4-carboxylate (ca.2.7g, 5 mmole) in methylene chloride (25 ml) was cooled to 0°, and pyridine (593 mg, 7.5 mmole) and phosphorus pentachloride (1.56 g, 7.5 mmole) were added. The reaction mixture was allowed to warm to 20° over 15 minutes and then stirred at this temperature for 2 hours. This solution was added dropwise over a period of 15 minutes to dry methanol (12 ml) cooled to −25° so that this temperature was maintained throughout the addition. Stirring was continued for 15 minutes at −20° to −25°, and the solvents were evaporated in vacuo. The residual oil was distributed between ethyl acetate and water (25 ml of each). The aqueous layer was separated and re-extracted with ethyl acetate (25 ml). The combined ethyl acetate layers were washed with water and 0.5N-hydrochloric acid (25 ml of each). The combined aqueous layers were concentraed in vacuo to ca. 50 ml and adjusted from pH 0.5 to 5.8 with N-sodium hydroxide solution under a layer of ethyl acetate (25 ml). The aqueous phase was re-extracted with ethyl acetate (25 ml) and the combined ethyl acetate layers were washed with water (25 ml), dried, concentrated in vacuo to ca.25 ml and treated with a solution of p-toluenesulphonic acid monohydrate (0.95 g, 5 mmole) in ethyl acetate (25 ml). An orange oil separated immediately, followed by a white solid; the oil solidified on keeping at 4° overnight. The solid was filtered off, washed with cold ethyl acetate and dried to give the title hydrogen-p-toluenesulphonate (196 mg, 7.0%), m.p. 195° to 196° (dec.) $[\alpha]_D$ + 1.2° $\lambda_{max.}$ (MeOH) 272 nm ($\epsilon$ 6,370).

A solid separated in two crops from the combined ethyl acetate layers from the initial separation. These crops were filtered off and dried to give the title hydrochloride: (i) (84 mg, 3.9%), m.p. 155° to 157° (dec.) $\lambda_{max.}$ (MeOH) 275 nm ($E_{1cm}^{1\%}$ 153); (ii) (58 mg, 2.7%), m.p. 173°–178° (dec.) $\lambda_{max.}$ (MeOH) 275 nm ($E_{1cm}^{1\%}$ 151).

EXAMPLE D16

2,2,2-Trichloroethyl 7β-phenylacetamido-3-n-propylthiomethylceph-3-em-4-carboxylate, 1β-oxide.

A solution of 2,2,2-trichloroethyl 3-bromomethyl-7β-phenylacetamidoceph-3-em-4-carboxylate, 1β-oxide (56 mg, 0.1 mmole) n-propanethiol (0.18 ml, 2 mmole) and triethylamine (0.01 ml, ca. 0.1 mmole) in N,N-dimethylformamide (1 ml.) was kept at ca.25° for 45 minutes, diluted with ethyl acetate (30 ml.), washed with brine (6 × 30 ml.) and evaporated. Ethyl acetate (3 × 30 ml.) was added to the residue and evaporated after each addition to remove traces of thiol. The residual oil (61.5 mg) was purified by preparative layer chromatography using acetone-methylene chloride (1:9) as eluant to give the title ester 1β-oxide (25 mg, 42%), $\lambda_{max.}$ 275 nm ($\epsilon$ 7,650), τ 1.63 (1H,d, J 9 Hz; N$\underline{H}$), 2.70 (5H, s, C$_6\underline{H}_5$), 4.20 (1H,dd, J 9,5 Hz; C7-$\underline{H}$) 4.81, 5.04 (2H, AB-quartet, J 12 Hz; C$\underline{H}_2$CCl$_3$), 5.02 (1H,d,J 5Hz; C$_6$-$\underline{H}$), 5.92, 6.29 (2H, AB-quartet, J 18 Hz; C$_2$-$\underline{H}_2$), 6.29, 6.49 (2H, AB-quartet, J 14 Hz; C$_3$-C$\underline{H}_2$S), 6.36 (2H, s; C$_6$H$_5$C$\underline{H}_2$), 7.56 (2H, t; SC$\underline{H}_2$CH$_2$), 8.5 (2H; m; SCH$_2$C$\underline{H}_2$CH$_3$), 9.10 (3H, t; CH$_2$C$\underline{H}_3$).

EXAMPLE D17

(i) 2,2,2-Trichloroethyl 7β-Formamido-3-methylthiomethylceph-3-em-4-carboxylate, 1β-oxide.

A solution of 2,2,2-trichloroethyl 3-bromomethyl-7β-formamidoceph-3-em-4carboxylate, 1β-oxide (14.06 g, 30 mmole) in N,N-dimethylformamide (200 ml) was cooled to −20° and treated with a solution of methanethiol (2.2 ml, 41 mmole) in cold (ca. −20°) N,N-dimethylformamide (50 ml). Triethylamine (4.2 ml, 30 mmole) was added and the cooling bath was withdrawn. The stirred solution reached 17° over 1 hr. and was then flushed with a rapid stream of nitrogen overnight to remove excess methanethiol. The solution was then divided into two equal portions, one of which was used directly for reduction of the 1β-oxide function [cf. B5(i) ], the other being worked up as follows. The solution was poured into water (600 ml) and extracted with methylene chloride (1 × 200 ml, 2 × 100 ml.). The combined extracts were washed with 2N-hydrochloric acid and water (200 ml of each), dried, and evaporated to give a pale yellow waxy solid. Crystallisation from methanol (20 ml) provided white needles which were collected using additional cold methanol (20 ml) to give the sulphoxide ester (5.25 g; 80.4%), m.p. 178° to 179°, $[\alpha]_D$ + 36.3° $\lambda_{max.}$ 274 nm ($\epsilon$ 8,250), $\nu_{max.}$ 3358 (NH), 1756 (azetidin-2-one), 1727 (CO$_2$CH$_2$CCl$_3$), 1690 and 1492 (CONH) and 1010 cm$^{-1}$(S→O), τ 1.60 (1H,d, J 9 Hz; N$\underline{H}$), 1.84 (1H, s; C$\underline{H}$O), 4.03 (1H, dd, J 5 and 9 Hz; C$_7$-$\underline{H}$), 4.78 and 4.99 (2H AB-q,J 12 Hz; C$\underline{H}_2$CCl$_3$), 4.92 (1H,d, J 5 Hz; C$_6$-$\underline{H}$), 5.86 and 6.23 (2H, AB-q,J b 18 Hz; C$_2$-$\underline{H}_2$), 6.32 (2H, s; C$\underline{H}_2$SCH$_3$), and 8.01 (3H, s; SC$\underline{H}_3$). Evaporation of the liquors, followed by crystallisation of the residue from methanol (10 ml), gave a second crop of similar material (0.32 g; 4.9%), m.p. 175° to 176°.

Analytical data was obtained on a recrystallised sample from a preliminary small-scale experiment, white needles (from methanol), m.p. 176° to 177°, $[\alpha]_D$ + 41.0° $\lambda_{max.}$ 275 nm ($\epsilon$ 8,600) (Found: C, 33.3; H, 3.0; Cl, 24.1; N, 6.6; S, 14.4. C$_{12}$H$_{13}$Cl$_3$N$_2$O$_5$S$_2$ (435.7) requires C, 33.1; H, 3.0; Cl, 24,4; N, 6.4; S, 14.7%).

(ii) 2,2,2-Trichloroethyl 7β-Formamido-3-methylthiomethylceph-3-em-4-carboxylate.

(a) 2,2,2-Trichloroethyl 7β-formamido-3-methylthiomethylceph-3-em-4-carboxylate, 1β-oxide (2.18g 5 mmole) was dissolved in glacial acetic acid (100 ml), and potassiumiodide (15.0g, 90 mmole) was added, followed by acetyl chloride (2.5 ml, 35 mmole), Iodine was liberated immediately. The mixtiure was stirred at ca.20° for 10 min., cooled in an ice-water bath and treated with aqueous 0.5M-sodium thiosulphate to destroy the iodine. The clear pale-yellow solution was concentrated in vacuo to remove the bulk of the acetic acid and the residue was partitioned between methylene chloride (250 ml) and water (250 ml).

The aqueous portion was extracted with methylene chloride (2 × 100 ml) and the combined organic extracts were washed with 3% aqueous sodium hydorgen carbonate (2 × 100 ml) and water (200 ml), dried and evaporated to give a white foam. Treatment with acetone (50 ml) left an insoluble yellow solid (sulphur) which was removed by filtration. The filtrate was evaporated and crystallised from methanol-water (10:1; 16.5 ml). The resulting fine white needles were collected, washed with methanol-water (10:1; 11 ml) and ether (5 ml), and dried to give the title ester (1.16g, 55.2%), m.p. 100° to 102°, $[\alpha]_D + 30.0°$, $\lambda_{max.}$ 270.5nm ($\epsilon$ 7,650), $\nu_{max.}$ 3290 (NH), 1770 (azetidin-2-one), 1715 ($CO_2CH_2CCl_3$), 1660 and 1505cm$^{-1}$(CONH) $\tau$ 0.95 (1H,d, J 9 Hz; N$\underline{H}$), 1.86 (1H,s; NC$\underline{H}$O), 4.24 (1H,dd, J 5 and 9 Hz; $C_7$-$\underline{H}$), 4.75 (1H,d,J 5 Hz; $C_6$-$\underline{H}$), 4.85 and 5.05 (2H,AB-q,J 12 Hz; $C\underline{H}_2CCl_3$), 6.26 and 6.46 (2H,AB-q, J 15 Hz; $C\underline{H}_2SCH_3$), 6.29 (2H,s; $C_2$—$C\underline{H}_2$), 7.96 (3H,s; —S$C\underline{H}_3$) (Found: C, 34.3; H, 3.1; Cl, 25.0; N, 6.6; S, 15.6. $C_{12}H_{13}Cl_3N_2O_4S_2$ (419.7) requires C, 34.3; H, 3.2; Cl, 25.3; N, 6.7; S, 15.3%). Evaporation of the combined filtrate and washings gave a residue, which after being dissolved in methanol-water (10:1; 5.5 ml) and brief refrigeration gave a second crop of crystals (117 mg; 5.6%), m.p. 97° to 98°, $[\alpha]_D + 30.0°$, $\lambda_{max.}$ 270.5nm ($\epsilon$ 7,650).

(b) Phosphorus trichloride (2.75 ml, 31.5 mmole) was added dropwise over 4 min. to a magnetically stirred solution of 2,2,2-trichloroethyl 7$\beta$-formamido-3-methylthiomethylceph-3-em-4-carboxylate, 1$\beta$-oxide (2.59g, 5.95 mmole) in dry methylene chloride (90 ml)-dry tetrahydrofuran (10 ml). The pale yellow solution was stirred at ca. 22° for 5 hr. during which time it became increasingly dark and cloudy. After refrigeration overnight ($-16°$) the solution was poured into water (200 ml) and the layers separated. The aqueous portion was extracted with methylene chloride (2 $\times$ 50 ml). The combined extracts were successively washed with water. 2N-hydrochloric acid, water, 3% aqueous sodium hydrogen carbonate and water (100 ml of each), dried, and divided into two equal portions. One portion was evaporated and the dark oily residue was dissolved in methanol (10 ml)-water (1 ml) and refrigerated. A gummy brown solid was deposited; this was collected and stirred with ether (20 ml) to give the title ester as pale-brown prisms (117 mg; 9.4%), m.p. 95° to 98°, $[\alpha]_D + 22.7°$, $\lambda_{max.}$ 270nm ($\epsilon$ 7,250). Evaporation of the aqueous methanol liquors gave a partially crystalline residue, which was triturated with aqueous methanol (1:1, 2 ml) to give a second crop of pale brown prisms (366 mg; 29.3%) m.p. 95° to 101°, $[\alpha]_D + 22.0°$, $\lambda_{max.}$ 270nm ($\epsilon$ 7,250).

(iii) 2,2,2-Trichloroethyl 7$\beta$-Amino-3-methylthiomethylceph-3-em-4-carboxylate. Hydrochloride.

Phosphorus oxychloride (0.5 ml. 5.47 mmole) was added dropwise over 3 min. to a stirred suspension of 2,2,2-trichloroethyl 7$\beta$-formamido-3-methylthiomethylceph-3-em-4-carboxylate (1.05 g., 2.5 mmole) in dry methanol (10 ml.). During the addition the starting material went into solution and the temperature of the mixture reached a maximum of ca.45°. After 1 min. a white solid came out of solution and the mixture rapidly set solid. The mixture was diluted with ether (10 ml.), stirred briefly and the product collected, washed with ether (ca. 25 ml.) and dried to furnish the title hydrochloride as a feathery white solid (941 mg., 88%), m.p. 169° to 172° (dec.) $[\alpha]_D + 5.25°$, $\lambda_{max.}$(MeOH) 272.5 nm. ($\epsilon$ 6,640), $\nu_{max.}$ ca. 2600 (N$^+$H$_3$), 1775 (azetidin-2-one) and 1720 cm$^{-1}$ ($CO_2CH_2CCl_3$), $\tau$ 4.69 (1H,d, J 5 Hz; $C_7$-$\underline{H}$), 4.88 and 5.01 (2H,AB-q, J 12 Hz; $C\underline{H}_2CCl_3$), 4.90 (1H,d, J 5 Hz; $C_6$-$\underline{H}$), 6.14 and 6.39 (2H,AB-q,J17 Hz $C_2$-$C\underline{H}_2$), 6.23 (2H,s; $C\underline{H}_2SCH_3$) and 7.97 (3H,s; S$C\underline{H}_3$) (Found: C, 31.2; H, 3.3; Cl, 33.0; N, 6.6; S, 15.0. $C_{11}H_{14}Cl_4N_2O_3S_2$ (428.2) requires C, 30.85, H, 3.3; Cl, 33.1; N, 6.55; S, 15.0%). Electrophoresis showed a single sot, $R_X$ 1.56 (X=cephalexin) which migrated towards the cathode and which gave a mauve colour upon spraying with 0.5% (W/V) ninhydrin in ethanol.

(iv) 2,2,2-Trichloroethyl 3-Methylthiomethyl-7$\beta$-[D-2-phenyl-2-(2,2,2-trichloroethoxycarbonylaminoacetamido] ceph-3-em-4-carboxylate.

To a suspension of 2,2,2-trichloroethyl 7$\beta$-amino-3-methylthiomethylceph-3-em-4-carboxylate, hydrochloride (1.60 g, 3.735 mmole) in methylene chloride (30 ml) was added a solution of sodium hydrogen carbonate (0.63g, 7.5 mmole) in water (30 ml). The mixture was stirred until solution was complete. The layers were separated and the aqueous portion was back-extracted with methylene chloride (15 ml). The combined organic extracts were washed with water (15 ml), dried and concentrated to ca.20 ml. The stirred solution was cooled in an ice-water bath and a solution of ethylene oxide (2 ml) in methylene chloride (3 ml) was added followed by a solution of D(—)-(N-2,2,2-trichloroethoxycarbonyl)-2-amino-2-phenylacetyl chloride (1.42 g, 4.11 mmole) in methylene chloride (10 ml + 10 ml ashings). The mixture set to a gel immediately which almost completely redissolved during 30 min. stirring at this temperature. The cooling bath was then withdrawn and isobutyl methyl ketone (25 ml) was added. After 30 min. stirring at ca. 25° the clear-yellow solution was washed with N-hydrochloric acid (50 ml), which was in turn back-extracted with methylene chloride (2 $\times$ 15 ml). The combined methylene chloride extracts were successively washed with water, 3% aqueous sodium hydrogen carbonate and water (50 ml. of each), then dried and evaporated to a yellow foam. Treatment with light petroleum (b.p. 60° to 80°) (30 ml) - ether (10 ml) provided the title ester as a pale yellow microcrystalline solid (2.54g, 97%), $[\alpha]_D - 30.3°$ (CHCl$_3$), $\lambda_{max.}$ 268.5 nm ($\epsilon$ 7,070) $\nu_{max.}$ (CHBr$_3$) 3436 (NH), 1781 (azetidin-2-one), 1736 ($CO_2CH_2CCl_3$), 1693 and 1510cm.$^{-1}$ (CONH), $\tau$ 0.66 (1H,d, J 9 Hz; $C_7$—N$\underline{H}$), 1.52 (1H,d, J 9 Hz; —OCO.N$\underline{H}$), 2.3 to 2.7 (5H,m, $C_6\underline{H}_5$), 4.24 (1H,dd, J 5 and 9 Hz; $C_7$—$\underline{H}$) 4.50 (1H,d, J 9 Hz; $C_6H_5C\underline{H}$-), 4.79 and 5.02 (2H,AB-q, J 13 Hz; $C_4$-$CO_2C\underline{H}_2CCl_3$), 4.81 (1H,d, J 5 Hz; $C_6$-$\underline{H}$), 5.16 (2H,s, NH.CO.OC$\underline{H}_2$CCl$_3$), 6.24 and 6.49 (2H,AB-q, J 14 Hz $C\underline{H}_2SCH_3$), 6.38 (2H,s; $C_2$-$C\underline{H}_2$), 7.99 (3H,s; SC$\underline{H}_3$), 8.7 and 9.1 (multiplets; light petroleum), TLC (2$\frac{1}{2}$% Me$_2$CO in CH$_2$Cl$_2$) showed a single spot, $R_F$ 0.44.

(v) 7$\beta$-(D-2-Amino-2-phenylacetamido)-3-methylthiomethylceph-3-em-4-carboxylic acid.

A solution of 2,2,2-trichloroethyl-3-methylthiomethyl-7$\beta$-[D-2-phenyl-2-(2,2,2-trichloroethoxycarbonylamino)acetamido] ceph-3-em-4-carboxylate (3.39g, 4.84 mmole) in 99% formic acid (66 ml) was cooled in an ice-water bath and zinc dust (3.39g,) was added, with stirring. The cooling bath was withdrawn and the mixture stirred at ca. 25° for 90 min., then filtered through a Celite pad. The pad was washed with 90% formic acid (25 ml) and the combined filtrate and washings placed on a De-acidite FF(Cl$^-$) ion-exchange column (50 ml; washed through with water (250 ml) and 90% formic acid (70 ml) before use). The column was eluted with 90% formic acid (150 ml). The filtrate was concentrated to ca. 5 ml and diluted with ether (10 ml) then added dropwise to magnetically stirred ether (200 ml) over 5-10 min.

The precipitated solid was collected, washed with ether and dried to give the title amino-acid as a fine white solid (1.48g; 77%), $[\alpha]_D$ + 87.5° ($CF_3CO_2H$). Most of this material (1.42g) was further purified by dissolving it in a mixture of 2N-hydrochloric acid (2.5 ml) and 50% aqueous acetone (20 ml) and adjusting the pH of the cooled (ice-water bath) solution from ca.1 to 5.5 with triethylamine. The mixture immediately set solid, and acetone (10 ml) was added. After refrigeration for 1 hr. the white solid was collected, washed with cold acetone (10 ml) and dried (951mg; 52%), $[\alpha]_D$ + 92.0° ($CF_3CO_2H$), $\lambda_{max.}$ (0.1M pH6 phosphate buffer) 263 nm ($E_{1cm}^{1\%}$ 200). Both p.m.r. spectroscopy and electrophoresis showed the presence of some cephalexin (ca. 7%), whilst the former showed the material to contain ca.10% by weight of triethylamine hydrochloride.

EXAMPLE D18

(i) 2,2,2-Trichloroethyl 3-Methylthiomethyl-7β-phenoxyacetamidoceph-3-em-4-carboxylate, 1β-Oxide.

Methanethiol (0.60 ml, 11.15 mmole) in N,N-dimethylformamide (5 ml) at −20° was added with stirring to a solution of 2,2,2-trichloroethyl 3-bromomethyl-7β-phenoxyacetamidoceph-3-em-4-carboxylate, 1β-oxide (5.48 g, 9.5 mmole) in N,N-dimethylformamide (50 ml) also at −20°. Triethylamine (1.42 ml, 10.2 mmole; 1.07 eq.) was added, causing a brown colouration which slowly lightened to a pale-yellow as the mixture was stirred and allowed to warm to 25° over 1 hr. Methylene chloride (100 ml) was added and the mixture was extracted with water (6 × 50 ml), dried, and evaporated to a brown solid which was triturated with ether-methanol (30 ml; 6:1) to give the *title compound* as an off-white solid (3.18g 61.8%), m.p. 175° to 183°, $[\alpha]_D$ + 0° (C.0.75), $\lambda_{max.}$ 269 nm ($E_{1cm}^{1\%}$ 172), inflexion at 264 nm ($E_{1cm}^{1\%}$ 150). A small sample was recrystallised from methanol to provide an analytical sample m.p. 178° to 182°, $[\alpha]_D$ + 0.2° (c, 0.065); $\lambda_{max.}$ 269 nm (ε 9,250) and 275 nm (ε 9,350), inflexion at 264 nm (ε 8,250), $\nu_{max.}$ 3387 (NH), 1770 (azetidin-2-one), 1738 ($CO_2R$), 1698 and 1522 (CONH), 1024 cm.$^{-1}$ (S→0), τ 1.84 (1H,d, J 9 Hz; N$\underline{H}$), 2.60 to 3.10 (5H, m; $C_6\underline{H}_5$), 3.94 (1H,dd, J9 Hz; and 4.5 Hz; $C_7$-$\underline{H}$), 4.77 and 4.97 (2H, AB-q,) J 12 Hz; $C\underline{H}_2CCl_3$), 4.87 (1H,d, J 4.5 Hz; $C_6$-$\underline{H}$), 5.30 (2H,s; $C_6H_5OC\underline{H}_2$), 5.82 and 6.21 (2H, AB-q, J 18 Hz; $C_2$-$\underline{H}_2$), 6.24 and 6.42 (2H, AB-q, J 12 Hz; $C\underline{H}_2SCH_3$), 7.99 (3H, s; $CH_2$—$SC\underline{H}_3$). (Found: C, 42.1; H, 3.5; Cl, 19.6; N, 5.2; S, 11.8. $C_{19}H_{19}Cl_3N_2O_6S_2$ (541.9) requires C, 42.1; H, 3.5; Cl, 19.7; N, 5.2; S, 11.8%).

(ii) 2,2,2-Trichloroethyl 3-Methylthiomethyl-7β-phenoxyacetamidoceph-3-em-4-carboxylate.

A solution of 2,2,2-trichloroethyl 3-methylthiomethyl-7β-phenoxyacetamidoceph-3-em-4-carboxylate, 1β-oxide (1.08 g, 2 mmole) in N,N-dimethylformamide (10 ml) was stirred at 26° with potassium iodide (2g, 12 mmole) and acetyl chloride (1 ml., 14 mmole). The brown colour of iodine soon appeared. After 10 minutes a solution of sodium metabisulphite in aqueous N,N-dimethylformamide was added to the reaction mixture until the colour was very pale-yellow. The reaction mixture was partitioned between water (50 ml.) and methylene chloride (100 ml.). The aqueous layer was extracted with methylene chloride (10 ml) and the combined organic layers were washed with water (3 × 50 ml), dried, and evaporated. The residual oil was dissolved in ether (25 ml) and washed with water (3 × 10 ml), dried, and evaporated to give the title compound as a pale-yellow foam (1.00 g, 95%), $[\alpha]_D$ + 37.5° $\lambda_{max.}$ 269 nm (ε 8,300) and 275 nm (ε 8,050), inflexion at 264 nm (ε 7,600) $\nu_{max.}$ ($CHBr_3$) 3460 (NH), 1790 (azetidin-2-one), 1740 ($CO_2R$), 1695 and 1525 cm.$^{-1}$ (CONH) τ 0.85 (1H,d, J 8 Hz; N$\underline{H}$), 2.60 to 3.14 (5H,m; $C_6\underline{H}_5$), 4.26 (1H,dd, J 8 and 4.5 Hz; $C_7$-$\underline{H}$), 4.72 (1H,d, J 4.5 Hz; $C_6$-$\underline{H}$), 4.80 and 5.00 (2H, AB-q, J 13 Hz; $C\underline{H}_2CCl_3$), 5.38 (2H,s; $C_6H_5OC\underline{H}_2$), 6.20 and 6.42 (2H, AB-q J 13 Hz; $C\underline{H}_2SCH_3$), 6.24 (2H, s; $C_2$-$\underline{H}_2$), 7.97 (3H, s; $CH_2SC\underline{H}_3$) (Found: C, 43.6; H, 3.7; Cl, 19.9; N, 5.1; S, 12.2 $C_{19}H_{19}Cl_3N_2O_5S_2$(525.8) requires C, 43.4; H, 3.6; Cl, 20.2; N, 5.3; S, 12.2%).

(iii) 2,2,2-Trichloroethyl 7β-Amino 3-methylthiomethylceph-3-em-4-carboxylate. Hydrogen-p-toluene sulphonate A solution of 2,2,2-trichloroethyl 3-methylthiomethyl-7β-phenoxyacetamidoceph-3-em-4-carboxylate (3.72 g, from example D21 in dry methylene chloride (20 ml) was added to a suspension of phosphorus pentachloride (2.36 g, 11.3 mmole; ca. 1.60 eq.) in pyridine (0.92 ml; 11.5 mmole, ca. 1.6 eq.) at −20° and stirred at −20° for 2 hours, then at 0° for 1 hour, then at 18° for 2 hours. The mixture was added to methanol (50 ml) and stirred for 10 minutes. Water (100 ml.) and ethyl acetate (150 ml.) were added and the pH adjusted to 7.1 with solid sodium bicarbonate. The organic layer was washed with water, dried, and evaporated, and the residue was dissolved in methanol-ether (10 ml, 2:1). To this solution was added a solution of p-toluenesulphonic acid monohydrate (2g, 10.5 mmole) in methanol (15 ml.) and ether (5 ml.). Seeding the solution with a crystal of authentic material caused immediate crystallisation of the title compound. The mixture was chilled at −15° for 2 hours filtered and the solid dried in vacuo to provide the product as off-white crystals (1.83g, 47%) m.p. 184° to 187° (dec.), $[\alpha]_D$ + 3.4° $\lambda_{max.}$ (MeOH) 268 nm ($E_{1cm}^{1\%}$ 120). A second crop of the title compound was obtained by evaporation of the mother-liquors and recrystallisation of the residue from methanol-ether. The solid was isolated and dried to give off-white crystals (0.95g, 25%), m.p. 186° to 188° (dec,), $[\alpha]_D$ + 7.1° $\lambda_{max}$ (MeOH) 268 nm ($E_{1cm}^{1\%}$ 116). τ 2.50 and 2.90 (two 1H,d, J 8 Hz; $CH_3C_6H_4SO_3$-), 4.68 and 4.80 (2H, AB-q, J 5 Hz; $C_6$-$\underline{H}$ and $C_7$-$\underline{H}$), 4.85 and 5.00 (2H, AB-q, J 13 Hz; $C\underline{H}_2CCl_3$), 6.18 and 6.23 (2H, AB-q, J 13 Hz; $C\underline{H}_2SCH_3$), 6.24 (2H,s, $C_2$-$\underline{H}_2$), 7.69 (3H,s, $C\underline{H}_3C_6H_4$), and 7.95 (3H,s, $CH_2SC\underline{H}_3$). The P.M.R. spectra of the two samples of product identified the title compound.

EXAMPLE D19

Preparation of 2,2,2-trichloroethyl 7β-amino-3-methylthiomethylceph-3-em-4-carboxylate hydrochloride from the product of Example B3 without isolation of intermediates.

A solution of 2,2,2-trichloroethyl 3-bromomethyl-7β-formamidoceph-3-em-4-carboxylate, 1β-oxide (23.43 g, 50 mmole) in N,N-dimethylformamide (300 ml) was cooled to −5°, and condensed methanethiol (3.0 ml; ca. 56 mmole) was washed using precooled (−20°) N,N- dimethylformamide (50 ml). Triethylamine (7.0 ml, 50 mmole) was added and the solution was allowed to reach 15° over 30 min., then degassed at 15 nm. for a further 30 min. A small amount of crystallisation had taken place, so additional N,N-dimethylformamide (50 ml) was added and the resulting solution was cooled to −5°. Potassium iodide (16.6g, 100 mmole) was added, followed by acetyl chloride (7.2 ml, 100 mmole) over a period of 2 min. After ca. 2 min iodine was liberated. The cooling bath was withdrawn, and the solution stirred for 1 hr. and then refrigerated overnight at −17°. The solution was warmed to room temperature over 1 hr. and a solution of sodium metabisulphite (16.6g; ca. 75 mmole) in water (80 ml) was added. The pale-orange solution was poured into water (1500 ml) and extracted with methylene chloride (1000 ml, 500 ml, 250 ml). The combined extracts were washed successively with water, 2N-hydrochloric acid, water, 3% aqueous sodium hydrogen carbonate (100 ml. of each), dried, and evaporated to give an amber gum. This was dissolved in dry methanol (160 ml) and the solution was cooled in an ice-water bath. Phosphorus oxychloride (4.6 ml; 50 mmole) was added over 4 min. and after stirring for ca. 30 min. crystallisation of a white fluffy solid commenced. After a further 15 min. the mixture had set solid and was diluted with ether (75 ml), refrigerated for 1 hr. and the solid collected, washed with ether (100 ml) and dried to give the title hydrochloride (13.49g, 63.2%), m.p. 170°–172° (dec.) $[\alpha]_D$ + 7.0° $\lambda_{max.}$ (MeOH) 272.5 nm ($\epsilon$ 6,630). Progressive concentration of the liquors provided three additional crops of an identical solid (1.87g, 1.82g, 0.19g; total 18.15%). All crops showed identical mobility on electrophoresis to that for the product described under Example D17 (iii).

EXAMPLE D20

Preparation of 2,2,2-trichloroethyl 3-methylthiomethyl-7β-phenylacetamidoceph-3-em-4-carboxylate from the product of Example B2 without isolation of intermediate.

Triethylamine (0.70 ml, 5 mmole) and a solution of methanethiol (2.8 ml, ca. 10 equiv.) in dimethylformamide (10 ml,), previously cooled to −30°, were added to a solution of 2,2,2-trichloroethyl-3-bromomethyl-7β-phenylacetamidoceph-3-em-4-carboxylate, 1β-oxide (2.79 g, 5 mmole) in dimethylformamide (40 ml) cooled to −30°. The reaction solution was allowed to warm to 20° and then stirred at this temperature for 30 minutes then dilution of an aliquot with ethanol gave a solution with $\lambda_{max.}$ 274 nm. Nitrogen was passed through the dimethylformamide solution for 45 minutes to remove the excess of thiol and potassium iodide (5 g.) and acetyl chloride (5 ml.) were added. After 4 hours at 20°, t.l.c. (acetone-methylene chloride, 1:15) showed that reduction was complete. The solution was cooled in an ice-bath, and 0.1 N-sodium thiosulphate solution was added until the solution became pale-yellow. Methylene chloride and water (80 ml of each) were added and the aqueous layer was separated and reextracted with methylene chloride (100 ml.). The combined methylene chloride layers were washed with water (3 × 100 ml.), dried and evaporated to give the title ester as a solvated yellow gelatinous solid (2.76 g), $\lambda_{max.}$ 268 nm ($E_{1cm}^{1\%}$ 133).

EXAMPLE D21

Preparation of 2,2,2-trichloroethyl 3-methylthiomethyl-7β-phenoxyacetamidoceph-3-em-4-carboxylate from the product of Example B5 without isolation of intermediate 2,2,2-Trichloroethyl 3-bromomethyl-7β-phenoxyacetamidoceph-3-em-4-carboxylate, 1β-oxide (11.48g, 20 mmole) was reacted with methanethiol as in Example D18(i) and the resulting solution in N,N-dimethylformamide used directly in a reduction step as described in Example D18(ii) to provide the solvated title compound as a pale-yellow foam (10.90 g,), $[\alpha]_D$ + 37.5° (c, 1.25) $\lambda_{max.}$ 269 nm ($E_{1cm}^{1\%}$ 165) and 276 nm. ($E_{1cm}^{1\%}$ 160) inflexion at 263 nm ($E_{1cm}^{1\%}$ 151). The P.M.R. spectrum of this product closely resembled that of the product from Example D18(ii)

EXAMPLE D22

Preparation of 7β-(D-2-amino-2-phenylacetamido)-3-methylthiomethylceph-3-em-4-carboxylic acid from the product of Example B6

(a) 2,2,2-Trichloroethyl 3-methylthiomethyl-7β-[D-2-(2,2,2-trichloroethoxycarbonylamino)-2-phenylacetamido]ceph-3-em-4-carboxylate A solution of methanethiol (0.28 ml, ca. 5 equiv.) in dimethylformamide (10 ml) (previously cooled to −30°), and triethylamine (0.14 ml, 1 mmole) were added to a solution of 2,2,2-trichloroethyl 3-bromomethyl-7β-[D-2-phenyl-2-(2,2,2-trichloroethoxycarbonylamino)acetamido]ceph-3-em-4-carboxylate 1β-oxide (0.75g, 1 mmole) in dimethylformamide (10 ml) cooled to −30°. The reaction mixture was allowed to warm to 20° and then stirred at this temperature for 1½ hours, when dilution of an aliquot with ethanol gave a solution with $\lambda_{max.}$ 272 nm. Nitrogen was passed through the solution for 30 minutes to remove the excess of thiol, and potassium iodide (1.0g) and acetyl chloride (3.0 ml) were added. The reaction mixture was stirred for 1½ hours, diluted with water (100 ml) and methylene chloride (100 ml) and sodium metabisulphite was added to destroy the iodine. The aqueous phase was reextracted with methylene chloride (2 × 50 ml) and the combined organic extract was washed with water (4 × 100 ml), dried and evaporated to give the title compound as a yellow foam (0.71 g, 101%), $\lambda_{max.}$ 266 nm ($E_{1cm}^{1\%}$ 103), τ 2.04, 7.08, 7.15 (0.5M Me$_2$N-CHO).

(b) 7β-(D-2-Amino-2-phenylacetamido)-3-methylthiomethylceph-3-em-4-carboxylic acid The product (36 mg, 0.05 mmole) from (a) was dissolved in 98–100% formic acid and treated with zinc dust (0.2g; activated by washing with 2N-hydrochloric acid, water and formic acid). After 12 minutes, electrophoresis at pH 2.2 showed the formation of a new spot giving the same mauve colour on spraying the ninhydrin solution (0.5% W/V in ethanol) and having the same mobility as an authentic sample of 7β-(D-2-amino-2-phenylacetamido)-3-methylthiomethylceph-3-em-4-carboxylic acid.

EXAMPLE D23

2,2,2-Trichloroethyl 3-Benzoylthiomethyl-7β-phenylacetamidoceph-3-em-4-carboxylate, 1β-Oxide.

A solution of 2,2,2-trichloroethyl 3-bromomethyl-7β-phenylacetamidoceph-3-em-4-carboxylate 1βoxide (56 mg, 0.1 mmole) in N,N-dimethylformamide (3 ml.) was stirred with sodium thiobenzoate (160 mg, 1 mmole) for 15 minutes. The mixture was diluted with ethyl acetate and brine (30 ml of each), and the organic phase was washed with brine (3 × 30 ml) and evaporated to a yellow oil. This oil was purified by preparative layer chromatography on Kieselgel G using acetone-methylene chloride (1:9) as eluant to give the title ester 1β-oxide (46 mg, 75%), $\lambda_{max}$ 239.5 nm ($\epsilon$ 13,700) and 278 nm ($\epsilon$ 15,600), τ (CDCl$_3$) 2.1 to 2.7 (5H, m; SCOC$_6$H$_5$), 3.33 (1H,d, J 10 Hz; NH), 4.00 (1H,dd, J 10,4.5 Hz; C$_7$-H) 4.96, 5.20 (2H, AB-q J 12 Hz; CH$_2$CCl$_3$), 5.50, 6.09 (2H, AB-q J 14 Hz; C$_3$-CH$_2$SCO), 5.56 (1H,d, J 4.5 Hz; C$_6$-H), 6.22, 6.70 (2H, AB-q, J 18 Hz; C$_2$-H$_2$) 6.43 (2H,s; C$_6$H$_5$CH$_2$).

EXAMPLE D24

2,2,2-Trichloroethyl 7β-Formamido-3-[2-(5-methyl-1,3,4-thiadiazolyl-thiomethyl)]ceph-3-em-4-carboxylate 1β-oxide.

A solution of 2,2,2-trichloroethyl 3-bromomethyl-7β-formamidoceph-3-em-4-carboxylate 1β-oxide (2.34 g., 5 mmole) and triethylamine (0.70 ml., 5 mmole) in N,N-dimethylformamide (30 ml.) was treated with 2-mercapto-5-methyl-1,3,4- thiadiazole (0.66 g., 5 mmole) for 45 minutes at 25°, when dilution of an aliquot with ethanol gave a solution with $\lambda_{max}$ 275 nm. The solution was diluted with water (75 ml.) and extracted with chloroform (1 × 75 ml., 1 × 50 ml.). The combined extracts were washed with 2N-hydrochloric acid (100 ml.), water (3×100 ml.), dried and evaporated. The residual orange solid was dissolved in chloroform (25 ml.) and the solution diluted with ether (25 ml.) to give a pale-orange solid, which was filtered off, washed with chloroform-ether (1:1) and dried to give the title ester 1β-oxide (2.27 g., 87%), m.p. 127° to 128°, [α]$_D$ − 58°, $\lambda_{max}$ 275 nm ($\epsilon$ 11,800), $v_{max}$ 3300 (NH), 1787 (azetidin-2-one), 1732 (CO$_2$R), 1673 and 1510 (CONH), 1630 (C=N) and 1030 cm.$^{-1}$ (S→0), τ 1.56 (1H, d, J 10 Hz; NH), 1.80 (1H, s; CHO), 3.98 (1H, dd, J 10 Hz and 5 Hz; C$_7$-H), 4.78 and 4.95 (2H, AB-q, J 12 Hz; CH$_2$CCl$_3$), 4.98 (1H, d, J 5 Hz; C$_6$-H), 5.11 and 5.83 (2H, AB-q, J 14 Hz; C$_3$-CH$_2$S), 5.84 and 6.13 (2H, AB-q, J 18 Hz; C$_2$CH$_2$), 7.32 (3H, s; -CH$_3$) (Found: C, 31.6; H, 2.6; Cl, 21.3; 21.4; N, 10.5; S, 17.6; 18.0. C$_{14}$H$_{13}$Cl$_3$N$_4$O$_5$S$_3$ (519.8) requires C, 32.3; H, 2.5; Cl, 20.5; N, 10.8; S, 18.5%).

REACTIONS INVOLVING ALKANOL NUCLEOPHILES

EXAMPLE D25

2,2,2-Trichloroethyl 3-Methoxymethyl-7β-phenylacetamido ceph-3-em-4-carboxylate, 1β-oxide Triethylamine (1 drop) was added to a refluxing solution of 2,2,2-trichloroethyl 3-bromomethyl-7β-phenylacetamidoceph-3-em-4-carboxylate, 1β-oxide (56 mg, 0.1 mmole) in methanol (5 ml). Refluxing was continued for 4 hours. The methanol was evaporated and the residue was purified by preparative layer chromatography using acetone - methylene chloride (1:9) as eluant to give the title ester 1β-oxide as a yellow oil (17 mg, 35%), τ (CDCl$_3$) 2.75 (5H,s; C$_6$H$_5$), 3.24 (1H,d, J 10 Hz; NH), 3.99 (1H,dd, J 10,5 Hz; C$_7$-H), 5.04, 5.24 (2H, AB-q, J 12 Hz; CH$_2$CCl$_3$), 5.53, 5.80 (2H, AB-q, J 12 Hz; C$_3$—CH$_2$OCH$_3$), 5.56 (1H,d, J 5 Hz; C$_6$—H), 6.08, 6.43 (2H, AB-q, J 18 Hz; C$_2$-H$_2$), 6.42 (2H,s; C$_6$H$_5$CH$_2$), 6.71 (3H,s; OCH$_3$).

EXAMPLE D 26

2,2,2-Trichloroethyl 7β-Formamido-3-methoxymethylceph-3-em-4-carboxylate, 1β-Oxide A solution of mercuric perchlorate (400 mg, 1 mmole) in dry methanol (8 ml) was added to a suspension of 2,2,2-trichloroethyl 3-bromomethyl-7β-formamidoceph-3-em-4-carboxylte, 1β-oxide (469 mg, 1 mmole) in dry methanol (12 ml) when the starting material went into solution. After stirring for 5 minutes, the solution was poured into water (50 ml) and extracted with ethyl acetate (1 × 50 and 1 × 30 ml). The combined ethyl acetate extract was dried and evaporated. The residue was crystallised from ethanol to give the title ester 1β-oxide (134 mg, 32%), m.p. 176°, [α]$_D$ + 92° $\lambda_{max}$ 269.5 nm ($\epsilon$ 7,250), $v_{max}$ 3280 (NH), 1778 (azetidin-2-one), 1740 (CO$_2$R), 1660 and 1527 (CONH) and 1039 cm$^{-1}$ (S→0), τ 1.57 (1H,d, J 10 Hz; NH), 1.82 (1H,s; CHO), 3.99 (1H,dd, J 10.5 Hz; C$_7$-H), 4.78, 4.96 (2H, AB-q, J 12 Hz; CH$_2$CCl$_3$), 4.96 (1H,d, J 5 Hz; C$_6$-H), 5.61, 5.79 (2H, AB-q, J 13.5 Hz; C$_3$-CH$_2$-OCH$_3$), 5.95, 6.35 (2H, AB-q, J 18 Hz; C$_2$-H$_2$), 6.79 (3H,s, 0 CH$_3$) (Found: C, 33.1; H, 3.0; Cl, 23.55; N, 6.6; S, 7.6. C$_{12}$H$_{13}$Cl$_3$N$_2$O$_6$S (419.7) requies C, 34.3; H, 3.1; Cl, 25.3; N, 6.7; S, 7.6%).

EXAMPLE D27 t-Butyl 3-Methoxymethyl-7β-phenoxyacetamidoceph-3-em-4-carboxylate, 1β-Oxide

A solution of mercuric perchlorate (400 mg, 1 mmole) in dry methanol (8 ml) was added to a suspension of t-butyl 3-bromomethyl-7β-phenoxyacetamidoceph-3-em-4-carboxylate, 1β-oxide (500 mg, 1 mmole) in dry methanol (12 ml) when the starting material went into solution. The solution was stirred for 5 minutes, and a stream of hydrogen sulphide was passed in giving a yellow, and then black, precipitate. The mixture was filtered through Celite, and the filtrate was diluted with ethyl acetate and water. The aqueous phase was re-extracted with ethyl acetate (25 ml), and the combined organic phases were washed with water and saturated brine (25 ml of each), dried and evaporated. Trituration with light petroleum gave the title ester 1β-oxide (349 mg, 77%), m.p. 67° to 69°, [α]$_D$ + 36° $\lambda_{max}$ 264 nm ($\epsilon$ 7,650), 268 nm ($\epsilon$ 7,850) and 273 nm ($\epsilon$ 6,500), $v_{max}$ 3370 (NH), 1783 (azetidin-2-one),1720 (CO$_2$R), 1692 and 1530 (CONH) and broad 1040 cm$^{-1}$ (S→ 0), 96 1.85 (1H,d, J 10 Hz; NH), 2.5 to 3.1 (5H,m; C$_6$H$_5$OCH$_2$), 3.97 (1H,dd, J 10,5 Hz; C$_7$-H), 5.02 (1H,d, J 5 Hz; C$_6$-H), 5.32 (2H,s; C$_6$H$_5$OCH$_2$), 5.70, 5.90 (2H, AB-q, J 13 Hz; C$_3$-CH$_2$OCH$_3$), 6.05, 6.46 (2H, AB-q, J 18 Hz; C$_2$-H$_2$), 6.79 (3H,s; OCH$_3$), 8.49 (9H,s; CO$_2$C(CH$_3$)$_3$).

We claim:

1. A process which comprises reacting in the presence of irradiation by ultraviolet, visible light or γ-rays a compound of the formula

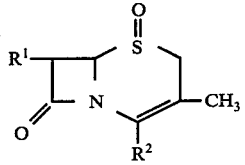

(I)

wherein $R^1$ is phenylacetamido or phenoxyacetamido and $R^2$ is carboxy or blocked carboxy with a brominating agent to produce a compound of the formula

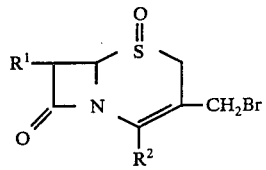

(II)

wherein $R^1$ and $R^2$ are as defined for formula (I).

2. A process as defined in claim 1 in which said brominating agent is bromine, an N-bromoamide, an N-bromoimide or 1,3,5-tribromo-1,2,4-triazole.

3. A process as defined in claim 1 in which said brominating agent is 1,3-dibromo-5,5-dimethylhydantoin, 1,3-dibromo-5-ethyl-5-methylhydantoin, 1,3-dibromo-5-isopropyl-5-methylhydantoin, N-bromosuccinimide, N-bromoacetamide, N-bromophthalimide or N-bromocaprolactam.

4. A process as defined in claim 1 wherein $R^2$ is 2,2,2-trichloroethoxycarbonyl or t-butoxycarbonyl.

* * * * *